US011090376B2

(12) United States Patent
Calvert et al.

(10) Patent No.: US 11,090,376 B2

(45) Date of Patent: Aug. 17, 2021

(54) EFFECTIVE VACCINATION AGAINST EUROPEAN STRAINS OF PORCINE REPRODUCTIVE AND RESPIRATORY SYNDROME (PRRS) VIRUS PRIOR TO WEANING

(71) Applicant: Zoetis Services LLC, Parsippany, NJ (US)

(72) Inventors: Jay Gregory Calvert, Otsego, MI (US); Monica Balasch, Olot (ES); Maria Fort, Olot (ES); Douglas S. Pearce, Kalamazoo, MI (US); Marcia L. Keith, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 136 days.

(21) Appl. No.: 16/469,321

(22) PCT Filed: Dec. 14, 2017

(86) PCT No.: PCT/US2017/066347

§ 371 (c)(1),
(2) Date: Jun. 13, 2019

(87) PCT Pub. No.: WO2018/112169

PCT Pub. Date: Jun. 21, 2018

(65) Prior Publication Data

US 2019/0365881 A1 Dec. 5, 2019

Related U.S. Application Data

(60) Provisional application No. 62/434,144, filed on Dec. 14, 2016.

(51) Int. Cl.

*A61K 39/12* (2006.01)
*C12N 7/00* (2006.01)
*A61K 39/00* (2006.01)

(52) U.S. Cl.

CPC ................ *A61K 39/12* (2013.01); *C12N 7/00* (2013.01); *A61K 2039/5254* (2013.01); *A61K 2039/552* (2013.01); *C12N 2770/10034* (2013.01); *C12N 2770/10064* (2013.01)

(58) Field of Classification Search

None
See application file for complete search history.

(56) References Cited

U.S. PATENT DOCUMENTS 3,137,631 A 6/1964 Soloway
3,519,710 A 7/1970 Bass
3,959,457 A 5/1976 Speaker et al.
4,016,100 A 4/1977 Suzuki et al.
4,205,060 A 5/1980 Monsimer et al.
4,452,747 A 6/1984 Gersonde et al.
4,606,940 A 8/1986 Frank et al.
4,744,933 A 5/1988 Rha et al.
4,921,706 A 5/1990 Roberts et al.
4,927,637 A 5/1990 Morano et al.
4,944,948 A 7/1990 Uster et al.
5,008,050 A 4/1991 Cullis et al.
5,009,956 A 4/1991 Baumann
5,132,117 A 7/1992 Speaker et al.
5,476,778 A 12/1995 Chladek et al.
5,620,691 A 4/1997 Wensvoort et al.
5,789,543 A 8/1998 Ingham et al.
5,840,563 A 11/1998 Chladek et al.
5,866,401 A 2/1999 Hesse
5,951,977 A 9/1999 Nisbet et al.
5,998,601 A 12/1999 Murtaugh et al.
6,015,686 A 1/2000 Dubensky, Jr. et al.
6,033,886 A 3/2000 Conzelmann
6,042,830 A 3/2000 Chladel et al.
6,197,310 B1 3/2001 Wensvoort et al.
6,268,199 B1 7/2001 Meulenberg et al.
6,500,662 B1 12/2002 Calvert et al.
6,943,152 B1 9/2005 Audonnet et al.
7,132,106 B2 11/2006 Calvert et al.
7,232,680 B2 6/2007 Calvert et al.
7,473,428 B2 1/2009 Johnson et al.
7,618,797 B2 11/2009 Calvert et al.
7,691,389 B2 4/2010 Calvert et al.
7,754,464 B2 7/2010 Calvert et al.
8,058,050 B2 11/2011 Calvert et al.

(Continued)

FOREIGN PATENT DOCUMENTS

EP 0839912 A1 5/1998
JP 9313188 12/1997

(Continued)

OTHER PUBLICATIONS

Sequence alignment of instant SEQ ID No. 5 with Geneseq db access No. AEN69132 Mar. 2007 by Faaberg et al.*

SEQ ID No. 6 sequence alignment with Genseq AFR07575, Jun. 2007.

GenEmbl ID GP721394 sequence alignment with SEQ ID No. 6, Dec. 2009.

Colson et al., Applied Animal Behavior Science, 2006, vol. 98, pp. 70-88.

O'Neill et al., Clinical and Vaccine Immunology, Nov. 2011, vol. 18, pp. 1865-1871.

(Continued)

*Primary Examiner* — Shanon A. Foley
(74) *Attorney, Agent, or Firm* — Vyacheslav Vasilyev

(57) ABSTRACT

The present invention provides modified live European PRRS viruses (whether or not recombinant) that have been at all times cultured, maintained, and/or attenuated on non-simian cells, typically porcine cells, wherein such cells express a porcine CD163 receptor, and whereinby vaccines prepared from such viruses are safe and efficacious, and permit the pre-weaning single dose vaccination of swine, typically as early as Day 1 of life.

7 Claims, 10 Drawing Sheets

Specification includes a Sequence Listing.

(56) References Cited

U.S. PATENT DOCUMENTS

| | | | | |
|---|---|---|---|---|
| 8,110,390 | B2 | 2/2012 | Faaberg et al. | |
| 8,420,373 | B2 | 4/2013 | Delputte et al. | |
| 8,481,705 | B2 | 7/2013 | Calvert et al. | |
| 8,492,132 | B2 | 7/2013 | Calvert et al. | |
| 8,609,827 | B2 | 12/2013 | Calvert et al. | |
| 9,102,912 | B2 | 8/2015 | Calvert et al. | |
| 9,566,324 | B2 | 2/2017 | Calvert et al. | |
| 10,383,934 | B2 * | 8/2019 | Calvert | A61P 43/00 |
| 10,610,581 | B2 * | 4/2020 | Calvert | C12N 7/00 |
| 2004/0087521 | A1 | 5/2004 | Donnelly et al. | |
| 2011/0177118 | A1 | 7/2011 | Zuckermann | |
| 2012/0213810 | A1 | 8/2012 | Burgard | |
| 2013/0309263 | A1 | 11/2013 | Calvert et al. | |
| 2014/0186395 | A1 | 7/2014 | Delputte et al. | |
| 2017/0136117 | A1 | 5/2017 | Calvert et al. | |
| 2019/0365881 | A1 * | 12/2019 | Calvert | A61K 39/12 |

FOREIGN PATENT DOCUMENTS

| | | |
|---|---|---|
| WO | WO 92/21375 | 12/1992 |
| WO | WO 93/03760 | 3/1993 |
| WO | WO 96/04010 A1 | 2/1996 |
| WO | WO 96/06619 | 3/1996 |
| WO | WO 95/28227 | 10/1996 |
| WO | WO 96/40932 | 12/1996 |
| WO | WO 98/55626 | 12/1998 |
| WO | WO 2007/002321 A2 | 1/2007 |
| WO | WO 2012/063212 A1 | 5/2012 |
| WO | WO 2013/173443 A1 | 11/2013 |

OTHER PUBLICATIONS

Reynolds et al., The Veterinary Journal, 2009, vol. 181, pp. 312-320.

Murtaugh et al., Virus Research, 2010, vol. 154, pp. 18-30.

Savard et al., Canadian Journal of Veterinary Research, 2016, vol. 80, pp. 1-11.

Han et al., Veterinary Microbiology, 2017, vol. 209, pp. 30-47.

Jeong et al., Veterinary Microbiology, 2018, vol. 214, pp. 113-124.

O'Brien et al., "Fostera PRRS Vaccine for One-Day-Old Piglets: Respiratory Efficacy, Duration of Immunity, and Safety Research", Dec. 2014, vol. 1-8, retrieved on internet at: https://www.Zoetisus.com/products/pork/fosteraprrs/documents/tech-update-fostera-prrs-1-day-of-age.pdf.

Zhou et al., Veterinary Microbiology, 2017, vol. 207, pp. 108-116.

Balasch, M. et al., 2018, "Vaccination of 1-day-old pigs with a porcine reproductive and respiratory syndrome virus (PRRSV) modified live attenuated virus vaccine is able to overcome maternal immunity", Porcine Health Management, vol. 4, pp. 1-11.

Pearce, D. S. et al., 2014, "Live virus determination of PRRSV vaccines on primary porcine alveolar macrophages", Proceedings 23rd International Pig Veterinary Society, p. 162, Jun. 8-11, 2014. Cancun, Mexico.

Xiangju Wu et al., "Establishment and Characterization of a High and Stable Porcine CD163-Expressing MARC-145 Cell Line", BioMed Research International, Article ID 4315861, 9 pages, Hindawi Publishers, 2018, https://doi.org/10.1155/2018/4315861.

Sornsen, S. A. et al., "Effect of various stocking methods and extra-label PRRS vaccination on average daily gain", Swine Health and Production, 1998, vol. 6, pp. 7-11.

Balasch, M., et al., 2019. "Immune response development after vaccination of 1-day-old naive pigs with a Porcine Reproductive and Respiratory Syndrome 1-based modified live virus vaccine", Porcine Health Management, 5: 2.

Balka, G., et al., 2018. "Genetic diversity of PRRSV 1 in Central Eastern Europe in 1994-2014: origin and evolution of the virus in the region", Scientific Reports, 8: 7811.

Bordet, E., et al., 2018. "Porcine Reproductive and Respiratory Syndrome Virus Type 1.3 Lena Triggers Conventional Dendritic Cells 1 Activation and T Helper 1 Immune Response Without Infecting Dendritic Cells", Frontiers in Immunology, 9: 2299.

Canelli, E., et al., 2018. "Efficacy of a modified-live virus vaccine in pigs experimentally infected with a highly pathogenic porcine reproductive and respiratory syndrome virus type 1 (HP-PRRSV-1)", Veterinary Microbiology, 226: 89-96.

Charerntantanakul, W., et al., 2018. "Co-administration of saponin quil A and PRRSV-1 modified-live virus vaccine up-regulates gene expression of type I interferon-regulated gene, type I and II interferon, and inflammatory cytokines and reduces viremia in response to PRRSV-2 challenge", Veterinary Immunology and Immunopathology, 205: 24-34.

Cortey, M., et al. 2018. "Bottlenecks in the transmission of porcine reproductive and respiratory syndrome virus (PRRSV1) to naive pigs and the quasi-species variation of the virus during infection in vaccinated pigs", Veterinary Research, 49: 107.

Dortmans, J.C.F.M., et al., 2019. "Molecular characterization of type 1 porcine reproductive and respiratory syndrome viruses (PRRSV) isolated in the Netherlands from 2014 to 2016", PLoS One [Electronic Resource], 14: e0218481.

Eclercy, J., et al., 2019. "A Field Recombinant Strain Derived from Two Type 1 Porcine Reproductive and Respiratory Syndrome Virus (PRRSV-1) Modified Live Vaccines Shows Increased Viremia and Transmission in SPF Pigs", Viruses, 11: 23.

Ferrari, L., et al., 2018. "A highly pathogenic porcine reproductive and respiratory syndrome virus type 1 (PRRSV-1) strongly modulates cellular innate and adaptive immune subsets upon experimental infection", Veterinary Microbiology, 216: 85-92.

Guo, Z., et al., 2018. "The prevalent status and genetic diversity of porcine reproductive and respiratory syndrome virus in China: a molecular epidemiological perspective", Virology Journal, 15: 2.

Jeong, J., et al., 2018. "A modified-live porcine reproductive and respiratory syndrome virus (PRRSV)-1 vaccine protects late-term pregnancy gilts against heterologous PRRSV-1 but not PRRSV-2 challenge", Transboundary & Emerging Diseases, 65: 1227-34.

Kang, H., et al., 2018. "Geographic distribution and molecular analysis of porcine reproductive and respiratory syndrome viruses circulating in swine farms in the Republic of Korea between 2013 and 2016", BMC Veterinary Research [Electronic Resource], 14: 160.

Kroll, J., et al., 2018. "Initial vaccination and revaccination with Type I PRRS 94881 MLV reduces viral load and infection with porcine reproductive and respiratory syndrome virus", Porcine Health Management, 4: 23.

Kwon, T., et al., 2019. "Differential evolution of antigenic regions of porcine reproductive and respiratory syndrome virus 1 before and after vaccine introduction", Virus Research, 260: 12-19.

Li, Y. L., et al., 2018. "Characterization of the attachment and infection by Porcine reproductive and respiratory syndrome virus 1 isolates in bone marrow-derived dendritic cells", Veterinary Microbiology, 223: 181-88.

Oh, T., et al., 2019. "Comparison of four commercial PRRSV MLV vaccines in herds with co-circulation of PRRSV-1 and PRRSV-2", Comparative Immunology, Microbiology and Infectious Diseases, 63: 66-73.

Renson, P., et al., 2019. "Maternally-derived neutralizing antibodies reduce vaccine efficacy against porcine reproductive and respiratory syndrome virus infection", Vaccine, 37: 4318-24.

Rodriguez-Gomez, I. M., et al., 2019. "Virulent Lena strain induced an earlier and stronger downregulation of CD163 in bronchoalveolar lavage cells", Veterinary Microbiology, 235: 101-09.

Sanchez-Carvajal, J. M., et al., 2019. "Kinetics of the expression of CD163 and CD107a in the lung and tonsil of pigs after infection with PRRSV-1 strains of different virulence", Veterinary Research Communications, 43: 187-95.

Singleton, H., et al., 2018. "Infection of monocytes with European porcine reproductive and respiratory syndrome virus (PRRSV-1) strain Lena is significantly enhanced by dexamethasone and IL-10", Virology, 517: 199-207.

Smith, N., et al., 2018. "Phylogenetic analysis of porcine reproductive and respiratory syndrome virus isolates from Northern Ireland", Archives of Virology, 163: 2799-804.

Xie, J., et al., 2019. "A Triple Amino Acid Substitution at Position 88/94/95 in Glycoprotein GP2a of Type 1 Porcine Reproductive and

(56) References Cited

OTHER PUBLICATIONS

Respiratory Syndrome Virus (PRRSV1) Is Responsible for Adaptation to MARC-145 Cells", Viruses, 11: 08.
Yuzhakov, A. G., et al., 2017. "Genetic and pathogenic characterization of a Russian subtype 2 PRRSV-1 isolate", Veterinary Microbiology, 211: 22-28.
Zhai, S. L., et al., 2018. "Phylogeographic analysis of porcine reproductive and respiratory syndrome virus 1 in Guangdong province, Southern China", Archives of Virology, 163: 2443-49.
Calzada-Nova, G., et al., 2010. "Characterization of the cytokine and maturation responses of pure populations of porcine plasmacytoid dendritic cells to porcine viruses and toll-like receptor agonists", Veterinary Immunology and Immunopathology, 135: 20-33.
Shi, M., et al., 2010. "Molecular epidemiology of PRRSV: A phylogenetic perspective", Virus Research, 154: 7-17.
Karniychuk, U.U., et al., 2010. "Pathogenesis and antigenic characterization of a new East European subtype 3 porcine reproductive and respiratory syndrome virus isolate", 6: 30.
U.S. Appl. No. 60/694,021, Han et al., filed Jun. 24, 2005.
Ishizeki, S. et al, Jul. 18-21, 2010, "Evaluation of the efficacy of PRRSV modified live vaccine in one-day old piglets," Poster Presentations, p. 232, Proceedings of the 21st IPVS Congress, Vancouver, Canada.
Markowska-Daniel, I. et al., 2011, "The influence of age and maternal antibodies on the postvaccinal response against swine influenza viruses in pigs," Veterinary Immunology and Immunopathology, 142:81-86.
O'Neill, K. et al., 2012, "Use of commercial subunit and chimeric vaccines in 5-day-old piglets is effective in protecting from PCV2 viremia and PCVAD in a PCV2, PPV and PRRSV triple challenge model," American Association of Swine Veterinarians Annual Meeting, p. 43.
Rossow, K. D., 1998, "Porcine reproductive and respiratory syndrome," Veterinary Pathology, 35: 1-20.
Butler, J. E., D. H. Francis, J. Freeling, P. Weber and A. M. Krieg (2005). "Antibody repertoire development in fetal and neonatal piglets. IX. Three pathogen-associated molecular patterns act synergistically to allow germfree piglets to respond to type 2 thymus-independent and thymus-dependent antigens." Journal of Immunology (Baltimore, Md.: 1950) 175: 6772-6785.
Butler, J. E. and M. E. Kehrle (2005). Immunoglobulins and immunocytes in the mammary gland and its secretions. Mucosal Immunology. J. Mestecky, M. E. Lamm, W. Strober et al., Academic Press. 2: 1763-1793.
Butler, J. E., M. Sinkora, N. Wertz, W. Holtmeier and C. D. Lemke (2006). "Development of the neonatal B and T cell repertoire in swine: implications for comparative and veterinary immunology." Veterinary Research 37: 417-441.
Hammerberg, C., G. G. Schurig and D. L. Ochs (1989). "Immunodeficiency in young pigs." American journal of veterinary research (USA)(6): 868.
Hurley, D. J. (2004). Neonatal immune development in swine management. American Association of Swine Veterinarians, Des Moines, Iowa.
Kumar, A., A. N. Vlasova, Z. Liu, K. S. Chattha, S. Kandasamy, M. Esseili, X. L. Zhang, G. Rajashekara and L. J. Saif (2014). "In vivo gut transcriptome responses to Lactobacillus rhamnosus GG and Lactobacillus acidophilus in neonatal gnotobiotic piglets." Gut Microbes, 5: 152-164.
Lemke, C. D., J. S. Haynes, R. Spaete, D. Adolphson, A. Vorwald, K. Lager and J. E. Butler (2004). "Lymphoid hyperplasia resulting in immune dysregulation is caused by porcine reproductive and respiratory syndrome virus infection in neonatal pigs." Journal Of Immunology (Baltimore, Md.: 1950) 172: 1916-1925.
Roth, J. A. (1999). The immune system. Diseases of Swine. B. E. Straw, S. D'Allaire, W. L. Mengeling and D. J. Taylor. Ames, Iowa, Iowa State Press: 799-820.
Sun, X. Z., N. Wertz, K. L. Lager, G. Tobin and J. E. Butler (2012). "Antibody repertoire development in fetal and neonatal piglets. XXIII: fetal piglets infected with a vaccine strain of PRRS virus display the same immune dysregulation seen in isolator piglets." Vaccine, 30: 3646-3652.
Zeidler, R. B. and H. D. Kim (1985). "Phagocytosis, chemiluminescence, and cell volume of alveolar macrophages from neonatal and adult pigs." Journal of Leukocyte Biology, 37: 29-43.
Ausubel, et al., "Current Protocols in Molecular Biology," Greene Publishing Associates & Wiley Interscience, NY (1989).
Allende, R ,et al., EMBL online database, AF046869 PRRS virus 16244B, complete genome Oct. 21, 1998.
Chasin, M., et al., "Biodegradable Polymers as Drug Delivery Systems," *Drugs and the Pharmaceutical Sciences*, vol. 45 (1990).
Coligan, JE., et al, Current Protocols in Immunology John Wiley & Sons, Inc. (1998).
Collins, J.E., et al., "Isolation of swine infertility and respiratory syndrome virus (isolate ATCC VR.23 2) in North America and experimental reproduction of the disease in gnotobiotic pigs," *J. Vet. Diagn. Invest.*, 4:117-126 (1992).
Den Boon JA, et al., *J. Virol*, 65(6):2910-2920 (1991).
Domb, A., et al., "Polymers for Advanced Technologies," 3:279-292(1992).
Erlich, "PCR Technology," Academic Press, Inc. 1992.
Enjuanes et al., *Journal of Biotechnology* 88:183-203, 2001.
Innis, et al., "PCR Strategies", Academic Press, Inc. (1995).
Kim, H.S,, et al., "Enhanced replication of porcine reproductive and respiratory syndrome (PRRS) virus in a homogeneous subpopulation of MA-104 cell line," *Arch Virol.*, 133:477-483 (1993).
Kwang, J., et al., "Cloning, expression, and sequence analysis of the ORF4 gene of the porcine reproductive and respiratory syndrome virus MN-Ib" Journal Bet. Diagn. Invest. 6:293-296_(1994).
Kreutz, LC. "Cellular membrance factors are the major determinants of porcine reproductive and respiratory syndrome virus tropism," Virus Research 53:121-128, 1998.
Mardassi, H., 1995., Arch. Virol. 140: 1405-1418.
Meulenberg, J.J.M. et al., "Lelystad Virus, the Causative Agent of Porcine Epidemic Abortion and Respiratory Syndrome (PEARS), is Related to LdV and EAV," *Virology*, 192:62-72(1993).
Murtaugh, MP et al., "Comparison of the structural protein coding sequences of the VR-2332 and Lelystad virus strains of the PRRS virus," *Arch Virol* 40:1 pp. 1451-1460 (1995).
Meng. X.J. et al., "Molecular cloning and nucleotide sequencing of the 3'-terminal genomic RNA of the porcine reproductive and respiratory syndrome virus," *J. Gen. Virol.*, 1795-1801(1994).
Meulenberg, J.J.M. et al., *Journal of Virology* 72, 380-387 (1988).
Murtaugh, EMBL online database, U87392. PRRS virus strain VR-2332 complete genome, Jan. 8, 1998.
Nelson, CJ, et al, GenBank, AF066183, Porcine reproductive and respiratory syndrome virus Resp PRRS MLV, complete genome, May 15, 1998.
Remington, "Pharmaceutical Science," 18th ed. Mack Publishing (1990).
Sambrook, et al., "Molecular Cloning: A Laboratory manual," 2ed., Cold Spring Harbor Laboratory Press, Cold Spring Harbor NY (1989).
Snijder, E.J. et al., "The molecula biology of arteriviruses," *Journal of General Virology*, 79:961-979 (1998).
Suarez, P. et al., "Phylogenetic relationships of European strains of porcine reproductive and respiratory syndrome virus (PRRSV) inferred from DNA sequences of putative ORF-5 and ORF-7 genes," *Virus Research*, 42:159-165(1996).
Terpstra, C. et al., Experimental reproduction of porcine epidemic abortion and respiratory syndrome (mystery swine disease) by infection with Lelystad virus: Koch's postulates fulfilled, Vet. Quart., 13:131-136 (1991).
Van Dinten LC., et al., An infectious arterivirus cDNA clone: identification of a replicase point mutation, which abolishes discontinuous mRNA transcription. Proceedings of the National Academy of Science USA 94: 991-996, (1997).
Wensvoort, G et al., Mystery swine disease in the Netherlands: the isolation of Lelystad virus, *Vet Quart.*, 13:121-130(1991).
Yang SX et al., Comparative sequence analysis of open reading frames 2 to 7 of the modified live vaccine virus and other North

(56) References Cited

OTHER PUBLICATIONS

American isolates of the porcine reproductive and respiratory syndrome virus, Archives ofVirology, NewYork, NY, US vol. 143, No. 3, 1998, pp. 601-612.
Murtaugh, et al., EMBL Online Database, U87392, PRRS virus strain VR-2332 complete genome, Nov. 19, 1998 last update Version 4.
Choi et al., Journal of Virology, 80: 723-736, 2006.
Nelsen et al., Journal of Virology, 73: 270-280, 1999.
Nielsen et al., Journal of Virology, 77: 3702-3711, 2003.
Tan et al., Virus Genes, 22: 209-217, 2001.
Abstract 176 from the CRWAD 82nd Annual Meeting, Nov. 2001.
Abstract p. 6.6 from the IXth International Symposium on Nidoviruses, May 2003.
Han et al., Journal of Virology, 83: 9449-9463, 2009.
Posthuma et al., Journal of Virology, 82: 4480-4491, 2008.
Pei et al., Virology, 389: 91-99, 2009.
Kapur et al., Journal of General Virology, 77: 1271-1276, 1996.
Chen, Z., X. Zhou, et al. (2010). "Immunodominant epitopes in nsp2 of porcine reproductive and respiratory syndrome virus are dispensable for replication, but play an important role in modulation of the host immune response." Journal of General Virology, 91: 1047-1057.
Faaberg, K. S., M. E. Kehrli, et al. (2010). "In vivo growth of porcine reproductive and respiratory syndrome virus engineered nsp2 deletion mutants." Virus Research, 154: 77-85.
Guo, B., A. C. Vorwald, et al. (2011). "Large scale parallel pyrosequencing technology: PRRSV strain VR-2332 nsp2 deletion mutant stability in swine." Virus Research, 161: 162-169.
Vandeputte et al., American Journal of Veterinary Research, 2001; 62: 1805-1811.
Murtaugh et al., Vaccine. 2011; 29: 8192-8204.
Issued Patents_NA database sequence alignment of U.S. Pat. No. 6,500,662 SEQ ID No. Dec. 1, 2002 with SEQ ID No. 6.
Issued Patents_NA database sequence alignment of U.S. Pat. No. 7,132,106 SEQ ID No. Nov. 1, 2006 with SEQ ID No. 6.
Issued Patents_NA database sequence alignment of U.S. Pat. No. 7,232,680 SEQ ID No. Jun. 1, 2007 with SEQ ID No. 6.
Issued Patents_NA database sequence alignment of U.S. Pat. No. 7,618,797 Nov. 2009 SEQ ID No. 1 with SEQ ID No. 6.
Issued Patents_NA database sequence alignment of U.S. Pat. No. 7,691,389 Apr. 2010 SEQ ID No. 1 with SEQ ID No. 6.
Issued Patents_NA database sequence alignment of U.S. Pat. No. 8,481,705 Jul. 2013 SEQ ID No. 1 with SEQ ID No. 6.
Issued Patents_NA database sequence alignment of U.S. Pat. No. 8,492,132 Jul. 2013 SEQ ID No. 1 with SEQ ID No. 6.
Published_Applications_NA_Main database sequence alignment of U.S. Appl. No. 12/615,504, now U.S. Pat. No. 8,609,827 Dec. 2013 SEQ ID No. 1 with SEQ ID No. 6.
Published_Applications_NA_Main database sequence alignment of U.S. Appl. No. 12/608,305 SEQ ID No. 1 with SEQ ID No. 6.
Christian Savard, et al., "Efficacy of Fostera PRRS modified live virus vaccine against a Canadian heterologous virulent field strain of porcine reproductive and respiratory syndrome virus," The Canadian Journal of Veterinary Research, pp. -11, 2016.
Ivan Trus, et al., "Efficacy of an attenuated European subtype 1 porcine reproductive and respiratory syndrome virus (PRRSV) vaccine in pigs upon challenge with the East European subtype 3 PRRSV strain Lena," Vaccine 32 (2014) pp. 2995-3003.
Debin Tian, et al., Chimeric porcine reproductive and respiratory syndrome virus containing shuffled multiple envelope genes confers cross-protection in pigs, Virology 485 (2015) pp. 402-413.
Unknown, "PRRSV-1 modified-live virus vaccine cross-protects against three major PRRSV subtypes prevalent in Europe", Posted on Sep. 8, 2020, https://pighealthtoday.com/mobile/article/?id=8104.

* cited by examiner complete genome sequence for SEQ ID NO:5

>96V198c1p49 complete genome passage 49 (SEQ ID NO:5)

ATGATGTGTAGGGTATTCCCCCTACATACACGACACTTCTAGTGTTTGTG
TGCCTTGGAGGCGTGGGTATAGCCCCGCCCCACCTCTTGGCCCCTGTTCT
AGCCCAACAGGTATCCTTCTCTCTCGGGGCGAGCGCGCCGCCTGCTGCTC
CCTTGCAGCAGGAAGGACCTCCCGAGTATTTCCGGAGAGCACCTGCTTTA
CGGGATCTCCACCCTTTAACCATGTCTGGGACGTTCTCCCGGTGCATGTG
CACCCCGGCTGCCCGGGTATTTTGGAGCGCCGGCCAAGTCTATTGCACAC
GGTGTCTCAGTGCACGGTCTCTTCTCTCTCCGGAGCTTCAGGACACTGAC
CTCGCTGCAATTGGCTTGTTTTACAAGCCTAAAGACAAGCTTCACTGGAA
AGTCCCTATCGGCATCCCTCAGGTGGAGTGTACTCCGTCCGGGTGCTGTT
GGCTCTCAGCCATCTTCCCCTTGGCGCGCATGACCTCCGGCAATCACAAC
TTTCTCCAACGACTTGTGAAGGTTGCTGATGTTTTGTACCGTGACGGCTG
CTTGGCACCTCGACACCTTCGCGAACTCCAAGTTTACGAGCGCGGCTGCA
ACTGGTACCCGATCACGGGGCCCGTGCCCGGGATGGGTTTGTACGCGAAC
TCCATGCACGTGTCCGACCAACCGTTCCCTGGTGCCGCTTATGTGTTAAC
GAACTCACCTCTGCCTCAGCAGGCTTGTCGACAGCCGTTTTGTCCATTTG
AGGAGGTTCATTCCGACGTATACAGGTGGAAGAAATTCGTGATTTTTGTG
GATTCCTCTTCTGACGGCCGATCTCGCATGATGTGGACACCAGGATCCGA
CGACTCGGCTGCCTTAGAAGTATTGCCACCTGAACTAGAATGTCGAGTCG
AAATCCTCGTTCGGAGTTTTCCTGCCCACCACCCTGTCGACATCACCAAC
TGGGAGCTCACTGAGTCCCCTGAGCACGGTTTTTCCTTCAGCACGTCTCA
TTCTTGTGGTTACCTTGCCCAAGACCCTGACGTGTTTGATGGTAAGTGTT
GGCTTTCTTGCTTTTTGGGCCTGCCGACCGAAGTGTGGCGTCATGAGGAG
CATCTAGCTAACGCCTTCGGTTACCAAACCAAGTGGGGCGTGCATGGTAA
GTACCTCCAGCGCAGGCTTCAGGTCCGCGGCATGCGTGCTGTAGTTGATC
CTGATGGTCCCATCCACGTTGAAGCGCTGTCTTGCCCCCAGTCTTGGATC
AGGCACCTGACTCTAAATGATGACGTCACCCCAGGATTTGTTCGCCTAAC
ATCCCTTCGCATTGAGCCGAACACAGAGCCTACTACTTTCCGGATCTTTC
GGTTTGGAGCGCATAAGTGGTATGGCGCTGCCGGCAAACGGGCTCGTGCT
AAGCGTGCCGCTAAAGGTGAGAAGAATTCAGCTCCCACCCCCAAGGTCGC
CCTGCCGGTCCCCACCTATGGAATTACCACCTACTCTCCACCGACAGACG
GGTCTTGTGGTTGGCATGTCCTTGCCGCCATAATGAACCGGATGATAAAT
GGTGACTTCACGTCCCCTCTGACTCCGTACAACAGACCAGAGGATGATTG
GGCTTCTGATTATGATCTTGCTCAGGCAATCCAATGTCTACAACTGCCTG

FIG. 1A complete genome sequence for SEQ ID NO:5

>96V198c1p49 complete genome passage 49 (SEQ ID NO:5)

CTACCGTGGTCCGGAGTCGCGCCTGTCCCAACGCCAAGTACCTCATAAAA
CTCAACGGAGTCCACTGGGAGGTAGAGGTGAGGTCAGGAATGGCTCCTCG
CTCTCTTTCTCGTGAATGTGTGGTTGGCGTTTGCTCTGAAGGTTGTGTTG
CACCGCCTTATCCAGCAGACGGGCTACCAGAACGAGCACTCGAGGCCTTG
GCGTCTGCTTACAGGTTACCCTCTGATTGTGTTAGCTCTGGCATTGCTGA
CTTTCTTGCTAACCCACCTCCTCAGGAATTCTGGACCCTCGACAAAATGT
TGACCTCCCCGTCACCAGAGCGGTCCGGCTTCTCTAGTTTGTATAAATTA
CTATTAGAGGTTGTTCCGCAAAAATGCGGTGCCACGGAAGGGGCTTTCGT
CTATGCTGTTGAGAGAATGTTGAAGGATTGTCCGAGCTCCAAACAGGCCA
TGGCCCTTCTGGCAAAAATTAAAGTTCCATCCTCAAAGGCCCCGTCTGTG
TCCCTTGACGAGTGTTTCCCTACGGATGTTTCAGCCGACTTCGAGCCAGC
ATCTCAGGAAAGGCCCCAAAGTTCCGGTGCTGCTGTTGTCCTGTGTTCAC
CGGAAGTAAAAGAGTTCGAAGAAGCAGCCCCAGAAGAAGTTCAAGAGAGT
GGCCATAAGGTCGCCCGCTCTGCATTTGTTGCCGAGGGTCCTAACAATGA
ACAGGTACCGATGGCTGCCGGCGAGCAACTGAAGCCCGGTGGTCGCGTTT
TGGCGGTCGGGAATGCTCATGAAGGTGTTCTGGCCTCAACTAGTTCGACC
AACCTGATAGGCGGGAACTTCCCCCCTTCAGACTCCATGAAAGAGAGCAT
GCTCAATAGCTGGGAAGACGAACCACTGGATTTGTCCCAACCGGCACCAG
CTGTTACAATGACCCTTGTGAGAGAGCAAACACCCGACAACCTGGGTCCT
GATGCCGGTGCCTTCCCCGTCACCGTTCGAAAATTTGTCCCGACAGGGCC
TACACTCCGTCATGTTGAGCACTGCGGCACGGAGTCAGGCGACAGCAGTT
CGCCCTTGGATCTGTCTTATGCGCAAACCCTGGACCAGCCTTTAAATCTA
TCCTTGGCCGCTTGGCCAGTGAGGGCCACCGCGTCTGACCCTGGCTGGGT
CCACGGTAGGCGTGAGCCTATCTTTGTGAAGCCTCGAGATGCTTTCTCTG
ACGGCGATTCAGCCCTTCAGCTCGGGGAGCTGTCTGAATCCGGCTCCGTC
ATCGAGTTTGACCGGACAAGAAATGCTCCGGCGGTCGACGCCCCTGTTGA
CTTGACGGCTTCGAACAAGGCCCTCTCTGTGGTTGATCCTTTCGAATTTG
CCGAACTCAAGCGCCCGCGTTTTTCCGCACAAGCCTTAATTGACCGAGGC
GGTCCACTTGCCGACGTCCATGCAAAAATAAAGAACCGGGTATATGAACA
GTGCCTCCAGGCTTGTGAGCCTGGCAGTCGCGCAACCCCAGCCACCAAGA
AGTGGCTCGATAAAATGTGGGATAGGGTGGACATGAAGACTTGGCGCTGT
ACCTCGCAGTTCCAAGCTGGTCGCATTCTTGCGTCCCTTAAATTCCTCCC

FIG. 1B complete genome sequence for SEQ ID NO:5

>96V198c1p49 complete genome passage 49 (SEQ ID NO:5)

TGACATGATTCAGGACACACCACCTCCTGTTCCTAGGAAGAATCGGGCTA
GTGATAATGCCGGCCTGAAGCGACTGGTGGCGCAGTGGGACAGAAAATTG
AGTGCAACCCCCCCTTCAAAACCGGTTGGACCAACACTTGACCAAATTGT
CCCTTCGCCCACGGGTACCCAGCAAGAAGATGTCACTTCCTCCGATGGGC
CATCTCATGCGCCGGATCCTCCTAGTCGAATGAGCACGAGTGGGAGTTGG
AAGGGCCTTGTGCTCTCTGGTACCCGTCTCGCGGGGTCCATTAGTCAGCA
TTTCATGACATGGGTTTTTGAGGTTTTCTCCCATCTCCCAGCTTTTGCAC
TCACACTTTTCTCGCCGAGGGGCTCTATGGCTTCAGGTGATTGGATGTTT
GCAGGTGTTGTTTTACTTGCTCTCCTGCTCTGTCGTTCTTACCCAGTATT
CGGGTGCCTTCCCTTATTGGGTGTCCTTTCTGGCTCTGTGCGGCGCGTTC
GTCTGGGGGTTTTTGGTTCTTGGATGGCTTTCGCTGTATTTTTATTCTCG
ACTCCATCCAACCCAGTCGGTTCTTCTTGTGACCACGATTCGCCGGAGTG
TCATGCTGAGCTTTTGGCTCTTGAGCAGCGCCAACTTTGGGAACCTGTGC
GCGGCCTTGTGGTCGGCCCCTCGGGCCTCTTATGTGTCATTCTTGGCAAG
CTACTCGGTGGGTCACGTTATCTCTGGCATGTTTTCTTACGTTTATGCAT
GCTTGCAGATTTGGCCCTTTCTCTTGTTTATGTGGTGTCCCAGGGGCGTT
GTCACAAGTGTTGGGGAAAGTGTATAAGAACAGCTCCGGCGGAGGTGGCT
CTCAATGTGTTCCCTTTCTCGCGCGCTACCCGTAGCTCTCTTGTGTCCTT
GTGCGATCGGTTCCAAGCGCCAAAAGGGGTTGATCCTGTGTACTTGGCAA
CGGGTTGGCGCGGGTGTTGGTGTGGTGAGAGTCCCATTCATCAACCGCAC
CAAAAACCCATAGCTTATGCTAATCTGGATGAAAAGAAAATATCTGCCCA
AACGGTGGTTGCTGTCCCACACGATCCCAGTCAGGCCATCAAGTGCCTGA
AAGTTTTGCAGGCGGGAGGAGCCATCGTGGACCAGCCCACACCTGAGGTC
GTCCGTGTATCCGAAATCCCCTTCTCAGCCCCATTTTTCCCAAAAGTTCC
AGTCAACCCAGATTGTAAGGTTGTGGTGGATTCGGACACTTTTGTGGCTG
CGGTTCGCTGCGGCTACTCGACAGCACAACTGGTCTTAGGCCAGGGCAAC
TTTGCCAAGTTAAATCAGATTCCCCTCAGGAGCTCTATCTCCACCAAAGC
GATTGGCGGGGCCTCTTACACCCTTGCTGTGGCTCAAGTTTCTGTGTGGA
CTCTTGTTCACTTCATCCTCGGTCTTTGGTTCACGTCACCCCAAGTGTGT
GGCCGAGGAACCTCTGACTCATGGTGTTCAAATCCTTTTTCATACCCTAC
CTATGGCCCCGGGGTTGTGTGCTCCTCTCGACTTTGTGTGTCTGCCGACG
GGGTCACTCTACCATTGTTCTCAGCCGTGGCTCAACTCTCCGGTAGAGAG

FIG. 1C complete genome sequence for SEQ ID NO:5

>96V198c1p49 complete genome passage 49 (SEQ ID NO:5)

GTGGGGATTTTTATTTTGGTACTCGTCTCCTTGATGGCTTTGGCCCACCG
CATGGCCCTTAAGGCAGACATGTTGATGGTCTTTCTGGCTTTTTGTGCTT
ACGCCTGGCCCATGAGCTCCTGGTTGATTTGCTTCTTTCCTACACTCTTG
AAGTGGGTTACCCTCCACCCTCTTACTATGCTTTGGGTGCACTCATTCTT
GGTGTTTTGTCTGCCAGCAGCCGGCATCCTCTCACTAGGGATAACTGGCC
TTCTTTGGGCGGTTGGCCGCTTTACTCAGGTTGCCGGAATTATTACACCT
TATGACATCCACCAGTACACCTCTGGGCCACGTGGCGCTGCAGCTGTGGC
CACAGCCCCAGAAGGCACTTATATGGCCGCCGTCCGGAGAGCTGCTTTAA
CTGGGCGAACTTTAATCTTCACCCCGTCTGCAGTTGGATCCCTTCTCGAA
GGAGCTTTCAGGACTCATAAACCTTGTCTTAACACCGTAAATGTTGTAGG
CTCTTCCCTTGGTTCCGGCGGGGTTTTCACTATTGACGGCAGAAAAATTG
TTGTCACTGCTGCCCATGTGTTGAACGGCGACACAGCTAGAGTCACCGGC
GACTCCTACAACCGCATGCATACTTTCAAGACCAATGGTGATTATGCCTG
GTCCCATGCTGATGACTGGCGGGGCGTTGCCCCTGCGGTCAAGGTTGCGA
AGGGGTACCGCGGTCGTGCCTACTGGCAAACATCAACTGGCGTCGAACCC
GGTGTTATTGGGGAAGGGTTCGCCTTCTGTTTCACCACCTGTGGCGATTC
GGGGTCACCCGTCATCTCAGAATCCGGTGATCTCATTGGAATCCATACCG
GTTCAAATAAACTTGGTTCTGGTCTTGTGACAACCCCTGAAGGGGAGACA
TGTACCATCAAAGAAACCAAGCTCTCTGACCTCTCCAGACATTTCGCAGG
CCCAAGCGTTCCTCTTGGGGATATTAAATTGAGTCCAGCCATCATCCCTG
ATATAACATCCATTCCGAGTGACTTGGCATCGCTCCTATCCTCCGTCCCT
GTAGTGGAAGGCGGCCTCTCGACCGTTCAACTTTTGTGTGTCTTTTTCCT
ACTTTGGCGCATGATGGGCCATGCCTGGACTCCCATTGTTGCCGTGGGTT
TCTTTTTACTGAATGAAATTCTTCCAGCAGTTTTGGTCCGAGCCGTGTTT
TCTTTTGCACTTTTTGTGCTTGCATGGGCCACCCCCTGGTCTGCACAGGT
GTTGATGATTAGACTCCTCACGGCATCTCTCAACCGCAATAAGCTTTCTC
TGGCGTTCTACGCACTCGGGGGGGTCGTCGGTTTGGCCGCTGAAATCGGG
ACTTTTGCTGGCAAATTGCCTGAATTGTCTCAAACCCTTTCGACATACTG
CTTCTTACCTAGGGTCCTTGCTATGACCAGTTGTGTTCCCACCATCATCA
TTGGTGGACTCCATGCCCTCGGTGTAATTCTGTGGTTGTTCAAATACCGG
TGCCTCCACAACATGCTCGTTGGTGATGGGAGTTTTTCAAGCGCCTTCTT

FIG. 1D complete genome sequence for SEQ ID NO:5

>96V198c1p49 complete genome passage 49 (SEQ ID NO:5)

CCTACGGTATTTTGCAGAGGGTAATCTCAGAAAAGGTGTTTCGCAGTCCT
GTGGCATGAATAACGAGTCCCTGACGGCTGCTTTGGCTTGCAAGTTGTCA
CGGGCTGACCTTGATTTTTTGTCCAGCTTAACGAACTTCAAGTGCTTTGT
ATCTGCTTCGAATATGAAAAATGCTGCCGGCCAGTACATTGAAGCGGCGT
ATGCCAAGGCCCTGCGCCAAGAGTTGGCGTCTCTAGTTCAGATTGACAAA
ATGAAAGGAGTTTTGTCCAAACTCGAGGCCTTTGCTGAAACAGCTACTCC
GTCCCTTGACATAGGTGACGTGATTGTTCTGCTTGGGCAACATCCACACG
GATCTATCCTTGATATTAATGTGGGGACTGAGAGGAAAACTGTGTCCGTG
CAAGAGACCCGGAGCCTAGGCGGTTCCAAATTCAGTGTTTGTACTGTCGT
GTCTAACACACCCGTGGACGCCTTAACCGGCATCCCACTCCAGACACCAA
CCCCTCTTTTTGAGAATGGTCCGCGTCATCGCAGCGAAGAAGACGATCTT
AAAGTCGAGAGGATGAAGAAACACTGTGTGCCCCTCGGCTTCCACAACAT
CAATGGCAAAGTTTACTGCAAGATTTGGGACAAGTCCACCGGTGACACCT
TTTACACGGATGATTCCCGGTATACCCACGACCATGCTCTTCAGGACAGG
TCAGCCGACTACAGAGACAGGGACTATGAGGGTGTGCAAACCGCCCCCCA
ACAGGGATTTGATCCAAAGTCTGAAACCCCTGTCGGCACTGTTGTGATCG
GCGGTATTACGTATAACAGGTATCTGACTAAGGGTAAGGAGGTTCTGGTT
CCCAAGCCCGACAATTGCCTTGAAGCTGCCAAGCTGTCTCTTGAGCAAGC
TCTCGCTGGGATGGGCCAAACTTGCGACCTTACAGCTGCCGAGGTGGAAA
AGTTAAAGCGCATCATCAGTCAACTCCAAGGTTTGACCACTGAACAGGCT
TTAAACTGCTAGCCGCTAGCGGCTTGACCCGCTGTGGCCGCGGCGGCTTA
GTTGTTACTGAAACGGCGGTAAAAATTGTAAGATACCACAGCAGAACTTT
CACCTTGGGCCCTTTGGACCTAAAAGTCGCTTCTGAGGTGGAGGTGAAGA
GATCAACTGAGCAGGGCCACGCTGTTGTGGCAAACCTATGTTCTGGTGTT
GTATTGATGAGACCTCACCCACCGTCCCTTGTTGACGTTCTTCTGAAACC
CGGACTTGACACAACACCCGGCATTCAACCGGGGCATGGGGCCGGGAATA
TGGGCGTGGACGGTTCCATTTGGGATTTTGAAACCGCACCCACAAAGGCA
GAGCTCGAGTTGTCCAGGCAAATAATCCAAGCATGTGAAGTCAGGCGCGG
GGATGCCCCGAACCTCCAACTCCCTTACAAGCTCTGTCCAGTTAGGGGGG
ATCCTGAGCGGCATAAAGGCCGCCTTATCAATACCAGGTTTGGAGATTTG
CCTTACAAGACTCCTCAAGACACCAAGTCCGCAATCCACGCGGCTTGTTG
CCTGCACCCCAACGGGGCTCCCGTGTCTGATGGTAAATCCACATTAGGCA

FIG. 1E complete genome sequence for SEQ ID NO:5

>96V198c1p49 complete genome passage 49 (SEQ ID NO:5)

CCACTCTTCAACACGGTTTCGAGCTTTATGTCCCTACTGTGCCCTATAGT
GTCATGGAGTACCTTGATTCACGCCCTGACACCCCCTTTATGTGTACCAA
ACATGGTACCCCCGAGGCTGCTGCAGAGGACCTTCGAAAATATGACTTAT
CCACCCAAGGGTTTGTCCTGCCTGGGGTCCTACGTCTAGTACGCAGATTC
ATCTTTGGCCATATTGGTAAGGCACCGCCACTGTTCCTCCCATCAACTTA
TCCCGCCAAGAACTCTATGGCAGGGATCAATGGCCAGAGGTTCCCAACAA
AAGACGTTCAGAGCATACCTGAAATTGATGAAATGTGTGCCCGCGCTGTC
AAAGAGAATTGGCAAACTGTGACGCCTTGCACCCTCAAAAAACAGTATTG
TTCCAAGCCTAAAACCAGGACCATCCTTGGTACCAACAACTTCATTGCCT
TGGCTCACAGGTCGGCACTCAGCGGTGTCACTCAGGCGTTCATGAAAAAA
GCCTGGAAGTCCCCGATCGCCTTGGGGAAAAACAAATTTAAGGAGTTGCA
CTGCACTGTCGCCGGTAGGTGCCTCGAGGCCGACTTGGCCTCTTGTGATC
GCAGCACCCCGGCCATCGTGAGGTGGTTTGTTGCCAACCTCCTGTACGAA
CTTGCGGGTTGTGAAGAGTACTTGCCAAGCTATGTGCTCAATTGTTGCCA
TGACCTGGTGGCAACGCAAAATGGCGCCTTCACAAAACGTGGTGGCCTGT
CATCTGGAGACCCCGTTACCAGTGTGTCCAACACAGTGTATTCACTGGTG
ATTTATGCTCAGCACATGGTGCTGTCGGCTTTGAAGATGGGTCATGAAAT
CGGCCTCAAGTTCCTCGAGGAACAGCTTAAGTTCGAGGACCTTCTCGAAA
TCCAGCCTATGTTGGTATATTCTGATGACCTTGTATTGTATGCTGAAAGA
CCCACCTTCCCCAATTACCATTGGTGGGTTGAGCACCTTGACCTGATGCT
GGGTTTTAAGACAGACCCAAAAAAGACTGTCATAACTGACAAACCCAGCT
TTCTTGGCTGTAGAATCGAAGCGGGGCGACAACTGGTTCCCAGTCGCGAC
CGCATTCTGGCTGCTCTTGCATATCACATGAAGGCGCAGAACGCCTCAGA
GTATTATGCGTCTGCTGCCGCGATTCTGATGGACTCGTGTGCTTGCATTG
ACCACGATCCTGAGTGGTATGAGGACCTCATCTGCGGCATTGCTCGATGC
GCCCGCCAGGATGGCTACAGTTTCCCAGGCCCGCCGTTCTTCATGTCCAT
GTGGGAGAAGCTGAAAAGTCACAATGAAGGCAAGAAATTCCGCCACTGTG
GCATTTGTGACGCCAAGGCCGATCATGCGTCCGCCTGTGGGCTTGATTTA
TGTCTGTTCCACTCGCACTTTCATCAACACTGCCCTGTTACTCTGAGCTG
CGGCCATCATGCCGGTTCAAAAGAATGCCCACAGTGTCAGTCACCTGTTG
GAGCTGGTAAATCCCCCCTTGATGCAGTGCTGAAACAAATCCCGTACAAA
CCCCCTCGTCCTGTCATCATGAAGGTGGACAATAAAACAACGACCCTTGA

FIG. 1F complete genome sequence for SEQ ID NO:5

>96V198c1p49 complete genome passage 49 (SEQ ID NO:5)

CCCGGGAAGGTATCAGTCCCGTCGAGGTCTTGTTGCTGTCAAGAGGGGTA
TTGCAGGCAATGAGGTTGATCTCGCTGATGGAGACTATCAGGTGGTGCCC
CTTTTGCCAACCTGCAAAGACATAAACATGGTGAAGGTGGCTGTCAATGT
GCTACTCAGCAAGTTCATAGTGGGGCCGCCAGGTTCCGGCAAGACGACCT
GGCTACTGAGTCAAGTTCAGGATGATGATGTCATCTATACACCTACCCAT
CAGACCATGTTCGACATAGTCAATGCCCTCAAAGTCTGTAGGTATTCCAT
CCCAGTGGCTTCAGGGCTCCCTTTCCCACCGCCCGCCagatctggaCCGT
GGGTTAGGCTCGTTGCTAGCGGGCACATCCCTGGCCGAATATCATACCTT
GACGAGGCCGGATATTGCAATCATCTGGATATTCTCAGACTGCTTTCTAA
GACACCTCTTGTGTGTTTGGGTGACCTTCAGCAACTTCACCCTGTCGGCT
TTGACTCTTACTGTTATGTTTTTGATCACATGCCTCATAAGCAGCTGACC
ACTATTTATAGATTTGGCCCCAATATCTGTTCTGCCATTCAACCTTGTTA
CAGGGAAAAACTCGAATCTAAGGCCAGGAACACTAGGGTGGTTTTTACTG
CCCGGCCCGTGGCTTTTGGTCAGGTGTTGACGCCATATCATAAAGACCGC
ACCGGCTCAGCTATAACCATAGATTCATCCCAGGGAGCCACCTTTGATGT
TGTGACGCTGCATTTGCCGTCGCCAGATTCCCTGAACAAATCCCGGGCTC
TTGTAGCTATCACTCGGGCAAGGCATGGGTTGTTCATCTATGACCCTCAT
AACCAACTCCGGAAGTTTTTCAACTTAACACCTGAGCGCACTGATTGCAA
CCTCGTGTTCAACCGCGGGGACGAGTTGGTAGTTTTGAATGCAGATAATG
CAGTCACGACTGTGGCTAAGGTTCTGGAGGCGGGCCCGTCTCGGTTTCGA
GTATCAGATCCAAGGTGCAAGTCTCTTTTAGCCGCTTGCTCGGCCAGTCT
GGAAGGAGGCTGCATGCCACTGCCGCAAGTGGCACATAATCTGGGGTTTT
ACTTCTCTCCAGATAGTCCAGCATTTGCACCTCTGCCAAAAGAGCTGGCA
CCACATTGGCCGGTTGTTACTAGTCAGAACAACCAGGCATGGCCCGACCG
ACTTGTCGCTAGTATGCGGCCAGTTGATGCCCGCTACAGCAAGCCTATGG
TCGGTGCAGGGTATGTGGTTGGGCCATCCACTTTCCTTGGCACTCCTGGT
GTGGTGTCATACTATCTCACGCTGTACATCAGGGGTGAGCCCCAGGCCTT
GCCGGAGACACTCGTCTCAACGGGACGTATAGCTACTGATTGTCGAGAGT
ATCTCGACGCAGCTGAGGAAGAAGCAGCTAAAGAACTCCCTCACGCATTC
ATTGGCGATGTCAAAGGTACTACAGTGGGGGGGTGTCACCACATTACGTC
AAAATACCTTCCCAGGTCCTTGCCCAAGGACTCCGTTGCCGTGGTCGGAG
TGAGTTCGCCCGGCAAGGCTGCCAAAGCCGTGTGTACTCTCACCGATGTG

FIG. 1G complete genome sequence for SEQ ID NO:5

>96V198c1p49 complete genome passage 49 (SEQ ID NO:5)

TATCTTCCCGAGCTCCGGCCATATTTGCAACCGGAAACAGCATCGAAATG
CTGGAAACTTAAACTAGACTTCAGGGATGTCAGACTGATGGTCTGGAAAG
GAGCCACCGCATATTTCCAACTGGAGGGGCTCACATGGTCAGCGCTGCCC
GACTATGCCAGGTTCATTCAGCTACCAAAAGATGCCGTTGTGTACATTGA
TCCGTGCATAGGACCGGCAACAGCCAACCGTAAGGTTGTGAGAACTACAG
ATTGGCGAGCTGACCTGGCAGTGACACCGTACGACTACGGTGCTCAGAGC
ATTTTGACTACAGCCTGGTTCGAGGACCTTGGGCCGCAGTGGAAGATTTT
AGGGTTGCAACCCTTCAAGCGGGCATTTGGCTTTGAAAACACTGAGGATT
GGGCGATCCTTGCACGTCGCATGAACGACGGCAAGGACTACACTGACTAT
AACTGGAATTGTGTTCGACAACGCCCACATGCCATCTACGGACGTGCCCG
TGACCATACGTATCACTTTGCCCCTGGCACTGAACTGCAAGTAGAGCTAG
GTAAACCTCGGCTACCGCCTGAGCAAGTACCGTGAATCTAGAGTGATGCA
ATGGGGTCACTGTGGAGTAAAATCAGTCAACTGTTCGTGGATGCCTTCAC
TGAGTTCCTTGTTAGTGTGGTTGATATTGTCATCTTCCTTGCCATACTGT
TTGGGTTCACCGTTGCAGGGTGGTTACTGGTCTTTTTTCTCAGAGTGGTT
TGCTCCGCGCTTCTCCGTTCGCGCTCTGCCATTCACTCTTCCGAACTATC
GAAGGTCCTATGAGGGCTTGCTACCTAATTGCAGACCGGATGTTCCACAA
TTCGCATTCAAGCACCCATTGGGTATGTTTTGGCACATGCGAGTTTCCCA
CTTAATTGACGAAATGGTCTCTCGCCGCATTTATCAGACCATGGAACATT
CAGGTCAAGCGGCCTGGAAGCAGGTGGTTAGTGAAGCTACTCTCACAAGA
CTGTCAAAGCTCGACATAGTTCTCCACTTCCAACACCTGGCCGCAATAGA
GGCGGATTCTTGCCGCTTCCTCAGCTCACGACTTGTGATGCTGAAAAATC
TTGCTGTTGGCAATATGAGCCTACAGTACAACACCACGTTGGACCGCGTT
GAGCTCATCTTCCCAACACCAGGTACGAGGCCCAAATTGACCGATTTTAG
ACAATGGCTCGTCAGTGTGCACGCTTCTATTTTTTCCTCTGTGGCCTCAT
CAGTTACCTTGTTCATAGTGCTTTGGCTTCGAATTCCAGCTCTACGCTAT
GTTTTTGGTTTCCATTGGCCCACGGCAACACATCATTCGAGCTAACCATC
AATTACTCTATATGTAAGCCCTGTCTCACCAGTCAAGCGGCTCGACAAAG
GCTCGAACCCGGTCGCAACATGTGGTGCAAAATAGGGCACACCACGTGTG
AGGAGCGTGACCATGATGAGTTGTCAATGACCATTCCGTCCGGGTACGAT
AACCTCAAACTTGAGGGTTATTACGCTTGGCTGGCTTTTTTGTCCTTTTC
TTACGCAGCCCAATTTCATCCAGAGTTGTTCGGAATAGGGAATGTGTCAC

FIG. 1H complete genome sequence for SEQ ID NO:5

>96V198c1p49 complete genome passage 49 (SEQ ID NO:5)

GCGTCTTCGTGGATAAACGGCACCAGTTCATCTGTGCCGAGCACGACGGA
CAAAATTCAACCGTATCCACCGAACATAATATTTCCGCATTGTATGCGGC
GTACTACCACCACCAGGTAGACGGGGGCAATTGGTTCCACCTGGAATGGC
TGCGGCCTTTCTTTTCCTCCTGGCTAGTACTCAATATTTCATGGTTTCTG
AGGCGTTCGCCTGCAAGCCCTGTTTCTCGACGCATTTATCAGATATTGAG
ACCAACACGACCGCGGCTGCCGGTTTCATGGTCCTTCAGGACATCAACTG
TTTCCACAGTGGCTCAGAGGCACAAACGACTGGTCCCATCAGAAAGTCGT
CCCAATGCCGTGAAGCCGTCGGCACTCCCCAGTACATCAAGATAACGGCC
AATCTGACCGACGAATCATACTTGTACAACGCGGACTTGCTGATGCTTTC
TGCGTGCCTTTTCTACGCCTCAGAGATGAGCGAGAAAGGCTTTAAAGTCA
TTTTTGGGAATGTCTCTGGCGTTGTCTCCGCTTGTGTCAATTTTACAGAT
TATGTGGCCCATCTGACCCAACATACCCAGCAGCATCATTTGGTAACCAA
TCACATTCGGTTGCTACATTTCCTGACACCATCAGCGATGAGGTGGGCTA
CAACCATTGCTTGTTTGTTCGCCATTCTCTTGGCGATATGAGATGTTCTC
ACAAATCGGGGTGTTTCTTGACTCCGCACTCTTGCTTTTGGTGGTTTTTT
TTGCTGTGTACCGGCTTGTCCTGGTCCTTTGCCGATGGCAACGGCGACAG
CTCGACATACCAATATATATATAACTTGACGATATGCGAGCTGAATGGGA
CCGAATGGCTGTCTGACCATTTTAATTGGGCAGTCGAGACTTTTGTGCTC
TACCCAGTGGCGACTCATATCCTCTCACTGGGTTTCCTCACGACAAGTCA
TTTCCTTGATGCGTTCGGTCTTGGAGCTGTGTCAATTACAGGGTTTTGTG
GCGGGCGGTACGTGCTCAGCAGCGTGTACGGCGCTTGTGCACTAGCAGCG
CTCGTATGTTTTGTTATCCGTGCTGCCAAAAATTGTATGGCTTGCCGCTA
TGCTCGTACCCGGTTTACCAACTTCATTGTGGATGACCGGGGGAGAATCC
ATCGGTGGAGGTCTCCAATAGTGGTGGAAAAATTAGGTAAAGCTGACGTC
GGCGGCGACCTTGTCACCATCAAACATGTCATCCTCGAAGGAGTCAAAGC
TCAACCCTTGACGAGGACTTCGGCCGAGCAATGGGAGGCCTAGATAATTT
CTGCAACGATCCCACCGCCGCACAAAAGCTTGTGCTAGCCTTTAGCATCA
CGTATACACCCATCATGATATACGCCCTTAAGGTGTCACGCGGCCGACTC
TTGGGGTTGTTGCACATCTTGATATTTCTGAACTGTTCTTTCACGTTCGG
ATACATGACATATATGCATTTTGAATCCACCAACCGTGTCGCGCTTACCA
TGGGGGGCGTTGTCGCCCTTCTGTGGGGCGTTTATAGTTTCATAGAGTCA
TGGAAGTTTATCACTTCCAGATGCAGATTGTGTTGCCTAGGCCGGCGATA

FIG. 1I complete genome sequence for SEQ ID NO:5

>96V198c1p49 complete genome passage 49 (SEQ ID NO:5)

```
CATTCTGGCCCCTGCCCACCACGTAGAAAGTGCTGCAGGCCTCCATCCGA
TCCCAGCGTCTGGTAACCAAGCATACGCTGTGAGAAAGCCCGGACTAACA
TCAGTGAACGGCACTCTGGTACCAGGACTTCGAGGCCTCGTGCTGGGCGG
CAAACGAGCTGTTAAACGAGGAGTGGTTAACCTCGTCAAGTATGGCCGGT
AAAAACCAGAGCCAGAAGAAAAAGAAAAATCCAGCTCCAATGGGGAATGG
CCAGTCAGTCAATCAACTGTGCCAGCTGCTGGGCACAATGATAAAGTCCC
AGCGCCAGCGACCCAGGGGAGGACAGGCTAAAAAGAAAAAGCCTGAGAAG
CCACATTTCCCCCTGGCTGCTGAAGATGACGTCCGGCACCATCTCACCCA
GACCGAGCGCTCCCTTTGCTTGCAATCGATCCAGACGGCTTTTAATCAAG
GCGCAGGAACTGCGTCGCTTTCATCCAGCGGGAAGATCGGTTTTCAGGTT
GAGTTTATGCTACCGGTTGCTCATACAGTGCGCCTGATTCGCGTGACTTC
TACATCCGCCGGTCAGGATGCAAATTAATTTGATAGTCAGGTGAATGGCC
GCGATTGGCGTGTGGCCTCTGAGTCACCTATTCAATTAGGGCGATCACAT
GGGGGTCAGACTTAATTAGGCAGGAACCATGTGACCGAAATT
```

FIG. 1J

SEQUENCE LISTING

<160> NUMBER OF SEQ ID NOS: 8

<210> SEQ ID NO 1
<211> LENGTH: 15092
<212> TYPE: DNA
<213> ORGANISM: Artificial Sequence
<220> FEATURE:
<223> OTHER INFORMATION: PRRS virus isolate 96V198 - passage 0

<400> SEQUENCE: 1

```
atgatgtgta gggtattccc cctacataca cgacacttct agtgtttgtg tgccttggag     60

gcgtgggtac agccccgccc cacctcttgg cccctgttct agcccaacag gtatccttct    120

ctctcggggc gagcgcgccg cctgctgctc ccttgcagca ggaaggacct cccgagtatt    180

tccggagagc acctgcttta cgggatctcc accctttaac catgtctggg acgttctccc    240

ggtgcatgtg caccccggct gcccgggtat tttggaacgc cggccaagtc ttttgcacac    300

ggtgtctcag tgcgcggtct cttctctctc cggagcttca ggacactgac ctcgctgcaa    360

ttggcttgtt ttacaagcct aaagacaagc ttcactggaa agtccctatc ggcatccctc    420

aggtggagtg tactccgtcc gggtgctgtt ggctctcagc catcttcccc ttggcgcgca    480

tgacctccgg caatcacaac tttctccaac gacttgtgaa ggttgctgat gttttgtacc    540

gtgacggctg cttggcacct cgacaccttc gcgaactcca agtttacgag cgcggctgca    600

actggtaccc gatcacgggg cccgtgcccg ggatgggttt gtacgcgaac tccatgcacg    660

tgtccgacca accgtttcct ggtgccactc atgtgttaac gaactcacct ctgcctcagc    720

aggcttgtcg acagccgttt tgtccatttg aggaggttca ttccgacgta tacaggtgga    780

agaaattcgt gatttttgtg gattcctctt ctgacggccg atctcgcatg atgtggacac    840

caggatccga cgactcggct gccttagaag tattgccacc tgaactagaa tgtcgagtcg    900

aaatcctcgt tcggagtttt cctgcccacc accctgtcga catcaccaac tgggagctca    960

ctgagtcccc tgagcacggt tttttccttca gcacgtctca ttcttgtggt taccttgccc   1020

aaaaccctga cgtgtttgat ggtaagtgtt ggctttcttg ctttttgggc ctgccgaccg   1080

aagtgtggcg tcatgaggag tatctagcta acgccttcgg ttaccaaacc aagtggggcg   1140

tgcatggtaa gtacctccag cgcaggcttc aggtccgcgg catgcgtgct gtagttgatc   1200

ctgatggtcc catccacgtt gaagcgctgt cttgcccccca gtcttggatc aggcacctga   1260

ctctaaatga tgacgtcacc ccaggatttg ttcgcctaac atcccttcgc attgagccga   1320

acacagagcc tactactttc cggatctttc ggtttggagc gcataagtgg tatggcgctg   1380

ccggcaaacg ggctcgtgct aagcgtgccg ctaaaggtga gaagaattca gctcccaccc   1440

ccaaggtcgc cctgccggtc cccacctgtg gaattaccac ctactctcca ccgacagacg   1500

ggtcttgtgg ttggcatgtc cttgccgcca taatgaaccg gatgataaat ggtgacttca   1560

cgtcccctct gactccgtac aacagaccag aggatgattg ggcttctgat tatgatcttg   1620

ctcaggcaat ccaatgtcta caactgcctg ctaccgtggt ccggagtcgc gcctgtccta   1680

acgccaagta cctcataaaa ctcaacggag tccactggga ggtagaggtg aggtcaggaa   1740

tggctcctcg ctctctttct cgtgaatgtg tggttggcgt ttgctctgaa ggttgtgttg   1800

caccgcctta tccagcagac gggctaccag aacgagcact cgaggccttg gcgtctgctt   1860

acaggttacc ctctgattgt gttagctctg gcattgctga ctttcttgct aacccacctc   1920

ctcaggaatt ctggaccctc gacaaaatgt tgacctcccc gtcaccagag cggtccggct   1980

tctctagttt gtataaatta ctattagagg ttgttccgca aaaatgcggt gccacggaag   2040
```

-continued

```
gggctttcgt ctatgctgtt gagagaatgt tgaaggattg tccgagctcc aaacaggcca   2100
tggcccttct ggcaaaaatt aaagttccat cctcaaaggc cccgtctgtg tcccttgacg   2160
agtgtttccc tacggatgtt tcagccgact tcgagccagc atctcaggaa aggccccaaa   2220
gttccggtgc tgctgttgtc ctgtgttcac cggaagtaaa agagttcgaa gaagcagccc   2280
cagaagaagt tcaagagagt ggccacaagg tcgcccgctc tgcatttgtt gccgagggtc   2340
ctaacaatga acaggtaccg atggctgccg gcgagcaact gaagcccggt ggtcgcgttt   2400
tggcggtcgg gaatgctcat gaaggtgttc tggcctcaac tagtccgact aacctgatag   2460
gcgggaactt ccccccttca gactccatga aagagagcat gctcaatagc tgggaagacg   2520
aaccactgga tttgtcccaa ccggcaccag ctgttacaat gacccttgtg agagagcaaa   2580
cacccgacaa cctgggtcct gatgccggtg ccttccccgt caccgttcga aaatttgtcc   2640
cgacagggcc tacactccgt catgttgagc actgcggcac ggagtcaggc gacagcagtt   2700
cgcccttgga tctgtcttat gcgcaaaccc tggaccagcc tttaaatcta tccttggccg   2760
cttggccagt gagggccacc gcgtctgacc ctggctgggt ccacggtagg cgcgagccta   2820
tctttgtaaa gcctcgagat gctttctctg acggcgattc agcccttcag ttcggggagc   2880
tgtctgaatc cggctctgtc atcgagtttg accggacaag aaatgctccg gcggtcgacg   2940
cctctgttga cttgacggct tcgaacgagg ccctctctgt ggttgatcct ttcgaatttg   3000
ccgaactcaa gcgcccgcgt tttccgcac aagccttaat tgaccgaggc ggtccacttg   3060
ccgacgtcca tgcaaaaata aagaaccggg tatatgaaca gtgcctccag gcttgtgagc   3120
ctggcagtcg cgcaacccca gccaccaagg agtggctcga taaaatgtgg gatagggtgg   3180
acatgaagac ttggcgctgt acctcgcagt tccaagctgg tcgcattctt gcgtccctta   3240
aattcctccc tgacatgatt caggacacac cacctcctgt tcctaggaag aatcgggcta   3300
gtgataatgc cggcctgaag cgactggtgg cgcagtggga cagaaaattg agtgcaaccc   3360
cccccttcaaa accggttgga ccaacacttg accaaattgt cccttcgccc acgggtaccc   3420
agcaagaaga tgtcacttcc tccgatgggc catctcatgc gccggatcct cctagtcgaa   3480
tgagcacgag tgggagttgg aagggccttg tgctctctgg tacccgtctc gcggggtcca   3540
ttagtcagca tttcatgaca tgggtttttg aggttttctc ccatctccca gcttttgcac   3600
tcacactttt ctcgccgagg ggctctatgg ctccaggtga ttggatgttt gcaggtgttg   3660
ttttacttgc tctcctgctc tgtcgttctt acccagtact cgggtgcctt cccttattgg   3720
gtgtcctttc tggctctgtg cggcgcgttc gtctgggggt ttttggttct tggatggctt   3780
tcgctgtatt tttattctcg actccatcca acccagtcgg ttcttcttgt gaccacgatt   3840
cgccggagtg tcatgctgag cttttggctc ttgagcagcg ccaactttgg gaacctgtgc   3900
gcggccttgt ggtcggcccc tcgggcctct tatgtgtcat tcttggcaag ctactcggtg   3960
ggtcacgtta tctctggcat gttttcttac gtttatgcat gcttgcagat ttggcccttt   4020
ctcttgttta tgtggtgtcc caggggcgtt gtcacaagtg ttggggaaag tgtataagaa   4080
cagctccggc ggaggtggct ctcaatgtgt tccctttctc gcgcgctacc cgtagctctc   4140
ttgtgtcctt gtgcgatcgg ttccaagcgc caaaaggggt tgatcctgtg tacttggcaa   4200
cgggttggcg cgggtgttgg tgtggtgaga gtcccattca tcaaccgcac caaaaaccca   4260
tagcttatgc taatttggat gaaaagaaaa tatctgccca aacggtggtt gctgtcccac   4320
acgatcccag tcaggccatc aagtgcctga aagttttgca ggcgggagga gccatcgtgg   4380
```

```
accagcccac acctgaggtc gtccgtgtat ccgaaatccc cttctcagcc ccatttttcc   4440
caaaagttcc agtcaaccca gattgtaagg ttgtggtgga ttcggacact tttgtggctg   4500
cggttcgctg cggctactcg acagcacaac tggtcctagg ccagggcaac tttgccaagt   4560
taaatcagat tcccctcagg agctccatct ccaccaaagc gattggcggg gcctcttaca   4620
cccttgctgt ggctcaagtt tctgtgtgga ctcttgttca cttcatcctc ggtctttggt   4680
tcacgtcacc ccaagtgtgt ggccgaggaa cctctgaccc atggtgttca aatccttttt   4740
catacccctac ctatggcccc ggggttgtgt gctcctctcg actttgtgtg tctgccgacg   4800
gggtcactct accattgttc tcagccgtgg ctcaactctc cggtagagag gtggggattt   4860
ttattttggt gctcgtctcc ttgatggctt tggcccaccg catggccctt aaggcagaca   4920
tgttgatggt ctttctggct tttgtgctt acgcctggcc catgagctcc tggttgattt   4980
gcttctttcc tacactcttg aagtgggtta ccctccaccc tcttactatg ctttgggtgc   5040
actcattctt ggtgttttgt ctgccagcag ccggcatcct ctcactaggg ataactggcc   5100
ttctttgggc ggttggccgc tttactcagg ttgccggaat tattacacct tatgacatcc   5160
accagtacac ctctgggcca cgtggcgcag cagccgtggc cacagcccca gaaggcactt   5220
atatggccgc cgtcaggaga gctgctttaa ctgggcgaac tttaatcttc accccgtctg   5280
cagttggatc ccttctcgaa ggagctttca ggactcataa accttgtctt aacaccgtaa   5340
atgttgtagg ctcttccctt ggttccggcg gggttttcac tattgacggc agaaaaattg   5400
ttgtcactgc tgcccatgtg ttgaacggcg acacagctag agtcaccggc gactcctaca   5460
accgcatgca tactttcaag accaatggtg attatgcctg gtcccatgct gatgactggc   5520
ggggcgttgc ccctgcggtc aaggttgcga aggggtaccg cggtcgtgcc tactggcaaa   5580
catcaactgg cgtcgaaccc ggtgttattg ggaagggttt cgccttctgt ttcaccacct   5640
gtggcgattc ggggtcaccc gtcatctcag aatccggtga tctcattgga atccataccg   5700
gttcaaataa acttggttct ggtcttgtga caacccctga aggggagaca tgtaccatca   5760
aagaaaccaa gctctctgac ctttccagac atttcgcagg cccaagcgtt cctcttgggg   5820
atattaaatt gagtccagcc atcatccctg atgtaacatc cattccgagt gacttggcat   5880
cgctcctatc ctccgtccct gtagtggaag gcggcctctc gaccgttcaa cttttgtgtg   5940
tctttttcct actttggcgc atgatgggcc atgcctggac tcccattgtt gccgtgggtt   6000
tctttttact gaatgaaatt cttccagcag ttttggtccg agccgtgttt tcttttgcac   6060
tttttgtgct tgcatgggcc accccctggt ctgcacaggt gttgatgatt agactcctca   6120
cggcatctct caaccgcaac aagctttctc tggcgttcta cgcactcggg ggggtcgtcg   6180
gtttggccgc tgaaatcggg acttttgctg gcaaattgcc tgaattgtct caaacccttt   6240
cgacatactg cttcttacct agggtccttg ctatgaccag ttgtgttccc accatcatca   6300
ttggtggact ccatgccctc ggtgtaattc tgtggttgtt caaataccgg tgcctccaca   6360
acatgctcgt tggtgatggg agtttttcaa gcgccttctt cctacggtat tttgcagagg   6420
gtaatctcag aaaaggtgtt tcgcagtcct gtggcatgaa taacgagtcc ctgacggctg   6480
ctttagcttg caagttgtca caggctgacc ttgatttttt gtccagctta acgaacttca   6540
agtgctttgt atctgcttcg aatatgaaaa atgctgccgg ccagtacatt gaagcggcgt   6600
atgccaaggc cctgcgccaa gagttggcat ctctagttca gattgacaaa atgaaaggag   6660
ttttgtccaa actcgaggcc tttgctgaaa cagctactcc gtcccttgac ataggtgacg   6720
tgattgttct gcttgggcaa catccacacg gatctatcct tgatattaat gtggggactg   6780
```

```
agaggaaaac tgtgtccgtg caagagaccc ggagcctagg cggttccaaa ttcagtgttt   6840
gtactgtcgt gtctaacaca cccgtggacg ccttaaccgg catcccactc cagacaccaa   6900
cccctctttt tgagaatggt ccgcgtcatc gcagcgaaga agacgatctt aaagtcgaga   6960
ggatgaagaa acactgtgtg tccctcggct tccacaacat caatggcaaa gtttactgca   7020
agatttggga caagtccacc ggtgacacct tttacacgga tgattcccgg tatacccacg   7080
accatgcttt tcaggacagg tcagccgact acagagacag ggactatgag ggtgtgcaaa   7140
ccgcccccca acagggattt gatccaaagt ctgaaacccc tgtcggcact gttgtgatcg   7200
gcggtattac gtataacagg tatctgacta agggtaagga ggttctggtt cccaagcccg   7260
acaattgcct tgaagctgcc aagctgtctc ttgagcaagc tctcgctggg atgggccaaa   7320
cttgcgacct tacagctgcc gaggtggaaa agttaaagcg catcatcagt caactccaag   7380
gtttgaccac tgaacaggct ttaaactgct agccgctagc ggcttgaccc gctgtggccg   7440
cggcggctta gttgttactg aaacggcggt aaaaattgta agataccaca gcagaacttt   7500
caccttgggc cctttggacc taaaagtcgc ttctgaggtg gaggtgaaga gatcaactga   7560
gcagggccac gctgttgtgg caaacctatg ttctggtgtt gtattgatga gacctcaccc   7620
accgtccctt gttgacgttc ttctgaaacc cggacttgac acaacacccg gcattcaacc   7680
ggggcatggg gccgggaata tgggcgtgga cggttccatt tgggattttg aaaccgcacc   7740
cacaaaggca gaactcgagt tgtccaagca aataatccaa gcatgtgaag tcaggcgcgg   7800
ggatgccccg aacctccaac tcccttacaa gctctgtcca gttagggggg atcctgagcg   7860
gcataaaggc cgccttatca ataccaggtt tggagatttg ccttacaaga ctcctcaaga   7920
caccaagtcc gcaatccacg cggcttgttg cctgcacccc aacggggctc ccgtgtctga   7980
tggtaaatcc acattaggca ccactcttca acacggtttc gagctttatg tccctactgt   8040
gccctatagt gtcatggagt accttgattc acgccctgac acccccttta tgtgtaccaa   8100
acatggtact cccgaggctg ctgcagagga ccttcgaaaa tatgacttat ccacccaagg   8160
gtttgtcctg cctggggtcc tacgtctagt acgcagattc atctttggcc atattggtaa   8220
ggcaccgcca ctgttcctcc catcaactta tcccgccaag aactctatgg cagggatcaa   8280
tggccagagg ttcccaacaa aagacgttca gagcatacct gaaattgatg aaatgtgtgc   8340
ccgcgctgtc aaagagaatt ggcaaactgt gacgccttgc accctcaaaa aacagtattg   8400
ttccaagcct aaaaccagga ccatccttgg taccaacaac ttcattgcct tggctcacag   8460
gtcggcactc agcggtgtca ctcaggcgtt catgaaaaaa gcctggaagt ccccgatcgc   8520
cttggggaaa aacaaattta aggagttgca ctgcactgtc gccggtaggt gcctcgaggc   8580
cgacttggcc tcttgtgatc gcagcacccc ggccatcgtg aggtggtttg ttgccaacct   8640
cctgtacgaa cttgcgggtt gtgaagagta cttgccaagc tatgtgctca attgttgcca   8700
tgacctggtg gcaacgcaaa atggcgcctt cacaaaacgt ggtggcctgt catctggaga   8760
ccccgttacc agtgtgtcca acacagtgta ttcactggtg atttatgctc agcacatggt   8820
gctgtcggct ttgaagatgg gtcatgaaat cggcctcaag ttcctcgagg aacagcttaa   8880
gttcgaggac cttctcgaaa tccagcctat gttggtatat tctgatgacc ttgtattgta   8940
tgctgaaaga cccaccttcc ccaattacca ttggtgggtt gagcaccttg acctgatgct   9000
gggttttaag acagacccaa aaaagactgt cataactgac aaacccagct ttcttggctg   9060
tagaatcgaa gcggggcgac aactggttcc caatcgcgac cgcattctgg ctgctcttgc   9120
```

```
atatcacatg aaggcgcaga acgcctcaga gtattatgcg tctgctgccg cgattctgat   9180
ggactcgtgt gcttgcattg accacgatcc tgagtggtat gaggacctca tctgcggcat   9240
tgctcgatgc gcccgccagg atggctacag tttcccaggc ccgccgttct tcatgtccat   9300
gtgggagaag ctgaaaagtc acaatgaagg caagaaattc cgccactgtg gcatttgtga   9360
cgccaaggcc gatcatgcgt ccgcctgtgg gcttgattta tgtctgttcc actcgcactt   9420
tcatcaacac tgccctgtta ctctgagctg cggccatcat gccggttcaa aagaatgccc   9480
acagtgtcag tcacctgttg gagctggtaa atcccccctt gatgcagtgc tgaaacaaat   9540
cccgtacaaa ccccctcgtc ctgtcatcat gaaggtggac aataaaacaa cgacccttga   9600
cccgggaagg tatcagtccc gtcgaggtct tgttgctgtc aagaggggta ttgcaggcaa   9660
tgaggttgat ctcgctgatg gagactatca ggtagtgccc cttttgccaa cctgcaaaga   9720
cataaacatg gtgaaggtgg ctgtcaatgt gctactcagc aagttcatag tggggccgcc   9780
aggttccggc aagacgacct ggctactgag tcaagttcag gatgatgatg tcatctatac   9840
acctacccat cagaccatgt tcgacatagt caatgccctc aaagtctgta ggtattccat   9900
cccagtggct tcagggctcc ctttcccacc gcccgccaga tctggaccgt gggttaggct   9960
cgttgctagc gggcacatcc ctggccgaat atcatacctt gacgaggccg gatattgcaa  10020
tcatctggat attctcagac tgctttctaa gacacctctt gtgtgtttgg gtgaccttca  10080
gcaacttcac cctgtcggct ttgactctta ctgttatgtt tttgatcaaa tgcctcataa  10140
gcagctgacc actatttata gatttggccc caatatctgt tctgccattc aaccttgtta  10200
cagggaaaaa ctcgaatcta aggccaggaa cactagggtg gtttttactg cccggcccgt  10260
ggcttttggt caggtgttga cgccatatca taaagaccgc accggctcag ctataaccat  10320
agattcatcc cagggagcca cctttgatgt tgtgacgctg catttgccgt cgccagattc  10380
cctgaacaaa tcccgggctc ttgtagctat tactcgggca aggcatgggt tgttcatcta  10440
tgaccctcat aaccaactcc ggaagttttt caacttaaca cctgagcgca ctgattgcaa  10500
cctcgtgttc aaccgcgggg acgagttggt agttttgaat gcagataatg cagtcacgac  10560
tgtggctaag gttttggagg cgggcccgtc tcggtttcga gtatcagatc caaggtgcaa  10620
gtctctttta gccgcttgct cggccagtct ggaaggaggc tgcatgccac tgccgcaagt  10680
ggcacataat ctggggtttt acttctctcc agatagtcca gcatttgcac ctctgccaaa  10740
agagctggca ccacattggc cggtggttac tagtcagaac aaccaggcat ggcccgaccg  10800
acttgtcgct agtatgcggc cagttgatgc ccgctacagc aagcctatgg tcggtgcagg  10860
gtatgtggtt gggccatcca ctttccttgg cactcctggt gtagtgtcat actatctcac  10920
gctgtacatc aggggtgagc cccaggcctt gccggagaca ctcgtctcaa cgggacgtat  10980
agctactgat tgtcgagagt atctcgacgc agctgaggaa gaagcagcta aagaactccc  11040
tcacgcattc attggcgatg tcaaaggtac tacagtgggg gggtgtcacc acattacgtc  11100
aaaatacctt cccaggtcct tgcccaagga ctccgttgcc gtggtcggag tgagttcgcc  11160
cggcaaggct gccaaagccg tgtgtactct caccgatgtg tatcttcccg agctccggcc  11220
atatttgcaa ccggaaacag catcgaaatg ctggaaactt aaactagact tcagggatgt  11280
cagactgatg gtctggaaag gagccaccgc atatttccaa ctggaggggc tcacatggtc  11340
agcgctgccc gactatgcca ggttcattca gctaccaaaa gatgccgttg tgtacattga  11400
tccgtgcata ggaccggcaa cagccaaccg taaggttgtg agaactacag attggcgagc  11460
tgacctggca gtgacaccgt acgactacgg tgctcagagc attttgacta cagcctggtt  11520
```

```
cgaggacctt gggccgcagt ggaagatttt agggttgcaa cccttcaagc gggcatttgg  11580
ctttgaaaac actgaggatt gggcgatcct tgcacgtcgc atgaacgacg gcaaggacta  11640
cactgactat aactggaatt gtgttcgaca acgcccacat gccatctacg gacgtgcccg  11700
tgaccatacg tatcactttg cccctggcac tgaactgcaa gtagagctag gtaaaccccg  11760
gctaccgcct gagcaagtac cgtgaatcta gagtgatgca atggggtcac tgtggagtaa  11820
aatcagtcaa ctgttcgtgg atgccttcac tgagttcctc gttagtgtgg ttgatattgt  11880
catcttcctt gccatactgt ttgggttcac cgttgcaggg tggttactgg tctttttttt  11940
cagagtggtt tgctccgcgc ttctccgttc gcgctctgcc attcactctt ccgaactatc  12000
gaaggtccta tgagggcttg ctacctaatt gcagaccgga tgttccacaa ttcgcagtca  12060
agcacccatt gggtatactt tggcacatgc gagtttccca cttaattgac gaaatggtct  12120
ctcgccgcat ttaccagacc atggaacatt caggtcaagc ggcctggaag caggtggtta  12180
gtgaagctac tctcacaaga ctgtcaaagc tcgacatagt tctccacttc caacacctgg  12240
ccgcaataga ggcggattct tgccgcttcc tcagctcacg acttgtgatg ctgaaaaatc  12300
ttgccgttgg caatatgagc ctacagtaca acaccacgtt ggaccgcgtt gagctcatct  12360
tcccaacacc aggtacgagg cccaaattga ccgattttag acaatggctc gtcagtgtgc  12420
acgcttctat tttttcctct gtggcctcat cagttacctt gttcatagtg ctttggcttc  12480
gaattccagc tctacgctat gtttttggtt tccattggcc cacggcaaca catcattcga  12540
gctaaccatc aattacacta tatgtaagcc ctgtctcacc agtcaagcgg ctcgacaaag  12600
gctcgaaccc ggtcgcaaca tgtggtgcaa aataggacac accacgtgtg aggagcgtga  12660
ccatgatgag ttgtcaatga ccattccgtc cgggtacgat aacctcaaac ttgagggtta  12720
ttacgcttgg ctggcttttt tgtccttttc ttacgcagcc caatttcatc cagagttgtt  12780
cggaataggg aatgtgtcac gcgtcttcgt ggataaacgg caccagttca tctgtgccga  12840
gcacgacgga caaaattcaa ccgtatccac cgaacataat atttccgcat tgtatgcggc  12900
gtactaccac caccaggtag acgggggcaa ttggttccac ctggaatggc tgcggccttt  12960
cttttcctcc tggctagtac tcaatatttc atggtttctg aggcgttcgc ctgcaagccc  13020
tgtttctcga cgcatttatc agatattgag accaacacga ccgcggctgc cggtttcatg  13080
gtccttcagg acatcaactg tttccacagt ggctcagagg cacaaacgac tggtcccatc  13140
agaaagtcgt cccaatgccg tgaagccgtc ggcactcccc agtacatcaa gataacggcc  13200
aatgtgaccg acgaatcata cttgtacaac gcggacttgc tgatgctttc tgcgtgcctt  13260
ttctacgcct cagagatgag cgagaaaggc tttaaagtca tttttgggaa tgtctctggc  13320
gttgtctccg cttgtgtcaa ttttacagat tatgtggccc atgtgaccca acatacccag  13380
cagcatcatt tggtaatcaa tcacattcgg ttgctacatt tcctgacacc atcagcaatg  13440
aggtgggcta caaccattgc ttgtttgttc gccattctct tggcgatatg agatgttctc  13500
acaaatcggg gtgtttcttg actccgcact cttgcttctg gtggcttttt ttgctgtgta  13560
ccggcttgtc ctggtccttt gccgatggca acggcaacag ctcgacatac caatatatat  13620
ataacttgac gatatgcgag ctgaatggga ccgaatggct gtccgaccat tttaattggg  13680
cagtcgagac ttttgtgctc tacccagtgg cgactcatat cctctcactg ggtttcctca  13740
cgacaagtca tttccttgat gcgttcggtc ttggagctgt gtcagttaca gggttttgtg  13800
gcgggcggta cgtgctcagc agcgtgtacg gcgcttgtgc actagcagcg ctcgtatgtt  13860
```

ttgttatccg tgctgccaaa aattgtatgg cttgccgcta tgctcgtacc cggtttacca 13920
acttcattgt ggatgaccgg gggagaatcc atcggtggag gtctccaata gtggtggaaa 13980
aattaggtaa agctgacgtc ggcggcgacc ttgtcaccat caaacatgtc atcctcgaag 14040
gagtcaaagc tcaacccttg acgaggactt cggccgagca atgggaggcc tagataattt 14100
ctgcaacgat cccaccgccg cacaaaagct tgtgctagcc tttagcatca catatacacc 14160
catcatgata tacgccctta aggtgtcacg cggccgactc ttggggttgt tgcacatctt 14220
gatatttctg aactgttctt tcacgttcgg atacatgaca tatatgcatt ttgaatccac 14280
caaccgtgtc gcgcttacca tggggggcgt tgtcgccctt ctgtggggcg tttatagttt 14340
catagagtca tggaagttta tcacttccag atgcagattg tgttgcctag gccggcgata 14400
cattctggcc cctgcccacc acgtagaaag tgctgcaggc ctccatccga tcccagcgtc 14460
tggtaaccaa gcatacgctg tgagaaagcc cggactaaca tcagtgaacg gcactctggt 14520
accaggactt cgaggcctcg tgctgggcgg caaacgagct gttaaacgag gagtggttaa 14580
cctcgtcaag tatggccggt aaaaaccaga gccagaagaa aaagaaaaat ccagctccaa 14640
tggggaatgg ccagtcagtc aatcaactgt gccagctgct gggcacaatg ataaagtccc 14700
agcgccagcg acccagggga ggacaggcta aaaagaaaaa gcctgagaag ccacatttcc 14760
ccctggctgc tgaagatgac gtccggcacc atctcaccca gaccgagcgc tccctttgct 14820
tgcaatcgat ccagacggct tttaatcaag gcgcaggaac tgcgtcgctt tcatccagcg 14880
ggaagatcgg ttttcaggtt gagtttatgc taccggttgc tcatacagtg cgcctgattc 14940
gcgtgacttc tacatccgcc ggtcaggatg caaattaatt tgatagtcag gtgaatggcc 15000
gcgattggcg tgtggcctct gagtcaccta ttcaattagg gcgatcacat gggggtcaga 15060
cttaattagg caggaaccat gtgaccgaaa tt 15092

<210> SEQ ID NO 2
<211> LENGTH: 15092
<212> TYPE: DNA
<213> ORGANISM: Artificial Sequence
<220> FEATURE:
<223> OTHER INFORMATION: PRRS virus isolate 96V198 - passage 1

<400> SEQUENCE: 2
atgatgtgta gggtattccc cctacataca cgacacttct agtgtttgtg tgccttggag 60
gcgtgggtac agccccgccc cacctcttgg cccctgttct agcccaacag gtatccttct 120
ctctcggggc gagcgcgccg cctgctgctc ccttgcagca ggaaggacct cccgagtatt 180
tccggagagc acctgcttta cgggatctcc accctttaac catgtctggg acgttctccc 240
ggtgcatgtg caccccggct gcccgggtat tttggaacgc cggccaagtc ttttgcacac 300
ggtgtctcag tgcgcggtct cttctctctc cagagcttca ggacactgac ctcgctgcaa 360
tcggcttgtt ttacaagcct aaagacaagc ttcactggaa agtccctatc ggcatccctc 420
aggtggagtg tactccgtcc gggtgctgtt ggctctcagc catcttcgtc ttggcgcgca 480
tgacctccgg caatcacaac tttccccaac gacttgtgaa ggttgctgat gttttgtacc 540
gtgacggctg cttggcacct cgacaccttc gcgaactcca agtttacgag cgcggctgca 600
actggtaccc gatcacgggg cccgtgcccg ggatgggttt atacgcgaac tctatgcatg 660
tgtccgacca accgtttcct ggtgccaccc atgtgttgac gaactcacct ctgcctcagc 720
aggcttgtcg acagccgttt tgtccatttg aggaggttca ttccgacgta tacaggtgga 780
agaaattcgt gatttttgtg gattcctctt ctgacggccg atctcgcatg atgtggacac 840
caggatccga cgactcggct gccttagaag tattgccacc tgaactagaa tgtcgagtcg 900
aaatcctcgt tcggagtttt cctgcccacc accctgtcga catcaccaac tgggagctca 960
ctgagtcccc tgagcacggt tttccttca gcacgtctca ttcttgtggt taccttgccc 1020
aaaaccctga cgtgtttgat ggtaagtgtt ggctttcttg ctttttgggc ctgccgaccg 1080
aagtgtggcg tcatgaggag tatctagcta acgccttcgg ttaccaaacc aagtggggcg 1140
tgcatggtaa gtacctccag cgcaggcttc aggtccgcgg catgcgtgct gtagttgatc 1200
ctgatggtcc catccacgtt gaagcgctgt cttgcccccca gtcttggatc aggcacctga 1260
ctctaaatga tgacgtcacc ccaggatttg ttcgcctaac atcccttcgc attgagccga 1320
acacagagcc tactactttc cggatctttc ggtttggagc gcataagtgg tatggcgctg 1380
ccggcaaacg ggctcgtgct aagcgtgccg ctaaaggtga gaagaattca gctcccaccc 1440
ccaaggtcgc cctgccggtc cccacctgtg gaattaccac ctactctcca ccgacagacg 1500
ggtcttgtgg ttggcatgtc cttgccgcca taatgaaccg gatgataaat ggtgacttca 1560
cgtcccctct gactccgtac aacagaccag aggatgattg ggcttctgat tatgatcttg 1620
ctcaggcaat ccaatgtcta caactgcctg ctaccgtggt ccggagtcgc gcctgtccta 1680
acgccaagta cctcataaaa ctcaacggag tccactggga ggtagaggtg aggtcaggaa 1740
tggctcctcg ctctctttct cgtgaatgtg tggttggcgt ttgctctgaa ggttgtgttg 1800
caccgcctta tccagcagac gggctaccag aacgagcact cgaggccttg gcgtctgctt 1860
acaggttacc ctctgattgt gttagctctg gcattgctga ctttcttgct aacccacctc 1920
ctcaggaatt ctggaccctc gacaaaatgt tgacctcccc gtcaccagag cggtccggct 1980
tctctagttt gtataaatta ctattagagg ttgttccgca aaaatgcggt gccacggaag 2040
gggctttcgt ctatgctgtt gagagaatgt tgaaggattg tccgagctcc aaacaggcca 2100
tggcccttct ggcaaaaatt aaagttccat cctcaaaggc cccgtctgtg tcccttgacg 2160
agtgtttccc tacggatgtt tcagccgact tcgagccagc atctcaggaa aggccccaaa 2220
gttccggtgc tgctgttgtc ctgtgttcac cggaagtaaa agagttcgaa gaagcagccc 2280
cagaagaagt tcaagagagt ggccacaagg tcgcccgctc tgcatttgtt gccgagggtc 2340
ctaacaatga acaggtaccg atggctgccg gcgagcaact gaagcccggt ggtcgcgttt 2400
tggcggtcgg gaatgctcat gaaggtgttc tggcctcaac tagttcgact aacctgatag 2460
gcgggaactt cccccccttca gactccatga aagagagcat gctcaatagc tgggaagacg 2520
aaccactgga tttgtcccaa ccggcaccag ctgttacaat gacccttgtg agagagcaaa 2580
cacccgacaa cctgggtcct gatgccggtg ccttccccgt caccgttcga aaatttgtcc 2640
cgacagggcc tacactccgt catgttgagc actgcggcac ggagtcaggc gacagcagtt 2700
cgccccttgga tctgtcttat gcgcaaaccc tggaccagcc tttaaatcta tccttggccg 2760
cttggccagt gagggccacc gcgtctgacc ctggctgggt ccacggtagg cgtgagccta 2820
tctttgtaaa gcctcgagat gctttctctg acggcgattc agcccttcag ctcggggagc 2880
tgtctgaatc cggctccgtc atcgagtttg accggacaag aaatgctccg gcggtcgacg 2940
cccctgttga cttgacggct tcgaacgagg ccctctctgt ggttgatcct ttcgaatttg 3000
ccgaactcaa gcgcccgcgt tttccgcac aagccttaat tgaccgaggc ggtccacttg 3060
ccgacgtcca tgcaaaaata aagaaccggg tatatgaaca gtgcctccag gcttgtgagc 3120
ctggcagtcg cgcaacccca gccaccaagg agtggctcga taaaatgtgg gatagggtgg 3180

-continued

```
acatgaagac ttggcgctgt acctcgcagt tccaagctgg tcgcattctt gcgtccctta   3240
aattcctccc tgacatgatt caggacacac cacctcctgt tcctaggaag aatcgggcta   3300
gtgataatgc cggcctgaag cgactggtgg cgcagtggga cagaaaattg agtgcaaccc   3360
ccccttcaaa accggttgga ccaacacttg accaaattgt cccttcgccc acgggtaccc   3420
agcaagaaga tgtcacttcc tccgatgggc catctcatgc gccggatcct cctagtcgaa   3480
tgagcacgag tgggagttgg aagggccttg tgctctctgg tacccgtctc gcggggtcca   3540
ttagtcagca tttcatgaca tgggtttttg aggttttctc ccatctccca gcttttgcac   3600
tcacactttt ctcgccgagg ggctctatgg ctccaggtga ttggatgttt gcaggtgttg   3660
ttttacttgc tctcctgctc tgtcgttctt acccagtact cgggtgcctt cccttattgg   3720
gtgtcctttc tggctctgtg cggcgcgttc gtctgggggt ttttggttct tggatggctt   3780
tcgctgtatt tttattctcg actccatcca acccagtcgg ttcttcttgt gaccacgatt   3840
cgccggagtg tcatgctgag cttttggctc ttgagcagcg ccaactttgg gaacctgtgc   3900
gcggccttgt ggtcggcccc tcgggcctct tatgtgtcat tcttggcaag ctactcggtg   3960
ggtcacgtta tctctggcat gttttcttac gtttatgcat gcttgcagat ttggcccttt   4020
ctcttgttta tgtggtgtcc caggggcgtt gtcacaagtg ttggggaaag tgtataagaa   4080
cagctccggc ggaggtggct ctcaatgtgt tccctttctc gcgcgctacc cgtagctctc   4140
ttgtgtcctt gtgcgatcgg ttccaagcgc caaaaggggt tgatcctgtg tacttggcaa   4200
cgggttggcg cgggtgttgg tgtggtgaga gtcccattca tcaaccgcac caaaaaccca   4260
tagcttatgc taatttggat gaaaagaaaa tatctgccca aacggtggtt gctgtcccac   4320
acgatcccag tcaggccatc aagtgcctga aagttttgca ggcgggagga gccatcgtgg   4380
accagcccac acctgaggtc gtccgtgtat ccgaaatccc cttctcagcc ccatttttcc   4440
caaaagttcc agtcaaccca gattgtaagg ttgtggtgga ttcggacact tttgtggctg   4500
cggttcgctg cggctactcg acagcacaac tggtcctagg ccagggcaac tttgccaagt   4560
taaatcagat tcccctcagg agctccatct ccaccaaagc gattggcggg gcctcttaca   4620
cccttgctgt ggctcaagtt tctgtgtgga ctcttgttca cttcatcctc ggtctttggt   4680
tcacgtcacc ccaagtgtgt ggccgaggaa cctctgaccc atggtgttca aatccttttt   4740
cataccctac ctatggcccc ggggttgtgt gctcctctcg actttgtgtg tctgccgacg   4800
gggtcactct accattgttc tcagccgtgg ctcaactctc cggtagagag gtggggattt   4860
ttattttggt gctcgtctcc ttgatggctt tggcccaccg catggccctt aaggcagaca   4920
tgttgatggt ctttctggct tttgtgcttg acgcctggcc catgagctcc tggttgattt   4980
gcttctttcc tacactcttg aagtgggtta ccctccaccc tcttactatg ctttgggtgc   5040
actcattctt ggtgttttgt ctgccagcag ccggcatcct ctcaataggg ataactggcc   5100
ttctttgggc ggttggccgc tttactcagg ttgccggaat tattacacct tatgacatcc   5160
accagtacac ctctgggcca cgtggcgctg cagctgtggc cacagcccca gaaggcactt   5220
atatggccgc cgtccggaga gctgctttaa ctgggcgaac tttaatcttc accccgtctg   5280
cagttggatc ccttctcgaa ggagctttca ggactcataa accttgtctt aacaccgtaa   5340
atgttgtagg ctcttccctt ggttccggcg gggttttcac tattgacggc agaaaaattg   5400
ttgtcactgc tgcccatgtg ttgaacggcg acacagctag agtcaccggc gactcctaca   5460
accgcatgca tactttcaag accaatggtg attatgcctg gtcccatgct gatgactggc   5520
ggggcgttgc ccctgcggtc aaggttgcga aggggtaccg cggtcgtgcc tactggcaaa   5580
```

```
catcaactgg cgtcgaaccc ggtgttattg ggaagggtt cgccttctgt ttcaccacct   5640
gtggcgattc ggggtcaccc gtcatctcag aatccggtga tctcattgga atccataccg   5700
gttcaaataa acttggttct ggtcttgtga caacccctga aggagagaca tgtgccatca   5760
aagaaaccaa gctctctgac ctttccagac atttcgcagg cccaagcgtt cctcttgggg   5820
atattaaatt gagtccagcc atcatccctg atgtaacatc cattccgagt gacttggcat   5880
cgctcctatc ctccgtccct gtagtggaag gcggcctctc gaccgttcaa cttttgtgtg   5940
tctttttcct actttggcgc atgatgggcc atgcctggac tcccattgtt gccgtgggtt   6000
tctttttact gaatgaaatt cttccagcag ttttggtccg agccgtgttt tcttttgcac   6060
tttttgtgct tgcatgggcc accccctggt ctgcacaggt gttgatgatt agactcctca   6120
cggcatctct caaccgcaac aagctttctc tggcgttcta cgcactcggg ggggtcgtcg   6180
gtttggccgc tgaaatcggg acttttgctg gcaaattgcc tgaattgtct caaacccttt   6240
cgacatactg cttcttacct agggtccttg ctatgaccag ttgtgttccc accatcatca   6300
ttggtggact ccatgccctc ggtgtaattc tgtggttgtt caaataccgg tgcctccaca   6360
acatgctcgt tggtgatggg agtttttcaa gcgccttctt cctacggtat tttgcagagg   6420
gtaatctcag aaaaggtgtt tcgcagtcct gtggcatgaa taacgagtcc ctgacggctg   6480
ctttagcttg caagttgtca caggctgacc ttgatttttt gtccagctta acgaacttca   6540
agtgctttgt atctgcttcg aatatgaaaa atgctgccgg ccagtacatt gaagcggcgt   6600
atgccaaggc cctgcgccaa gagttggcat ctctagttca gattgacaaa atgaaaggag   6660
ttttgtccaa actcgaggcc tttgctgaaa cagctactcc gtcccttgac ataggtgacg   6720
tgattgttct gcttgggcaa catccacacg gatctatcct tgatattaat gtggggactg   6780
agaggaaaac tgtgtccgtg caagagaccc ggagcctagg cggttccaaa ttcagtgttt   6840
gtactgtcgt gtctaacaca cccgtggacg ccttaaccgg catcccactc cagacaccaa   6900
cccctctttt tgagaatggt ccgcgtcatc gcagcgaaga agacgatctt aaagtcgaga   6960
ggatgaagaa acactgtgtg tccctcggct tccacaacat caatggcaaa gtttactgca   7020
agatttggga caagtccacc ggtgacacct tttacacgga tgattcccgg tatacccacg   7080
accatgcttt tcaggacagg tcagccgact acagagacag ggactatgag ggtgtgcaaa   7140
ccgcccccca acagggattt gatccaaagt ctgaaacccc tgtcggcact gttgtgatcg   7200
gcggtattac gtataacagg tatctgacta agggtaagga ggttctggtt cccaagcccg   7260
acaattgcct tgaagctgcc aagctgtctc ttgagcaagc tctcgctggg atgggccaaa   7320
cttgcgacct tacagctgcc gaggtggaaa agttaaagcg catcatcagt caactccaag   7380
gtttgaccac tgaacaggct ttaaactgct agccgctagc ggcttgaccc gctgtggccg   7440
cggcggctta gttgttactg aaacggcggt aaaaattgta agataccaca gcagaacttt   7500
caccttgggc cctttggacc taaaagtcgc ttctgaggtg gaggtgaaga gatcaactga   7560
gcagggccac gctgttgtgg caaacctatg ttctggtgtt gtattgatga gacctcaccc   7620
accgtccctt gttgacgttc ttctgaaacc cggacttgac acaacacccg gcattcaacc   7680
ggggcatggg gccgggaata tggcgtgga cggttccatt tgggattttg aaaccgcacc   7740
cacaaaggca gaactcgagt tgtccaagca aataatccaa gcatgtgaag tcaggcgcgg   7800
ggatgccccg aacctccaac tcccttacaa gctctgtcca gttagggggg atcctgagcg   7860
gcataaaggc cgccttatca ataccaggtt tggagatttg ccttacaaga ctcctcaaga   7920
```

-continued

```
caccaagtcc gcaatccacg cggcttgttg cctgcacccc aacggggctc ccgtgtctga   7980
tggtaaatcc acattaggca ccactcttca acacggtttc gagctttatg tccctactgt   8040
gccctatagt gtcatggagt accttgattc acgccctgac acccccttta tgtgtaccaa   8100
acatggtact cccgaggctg ctgcagagga ccttcgaaaa tatgacttat ccacccaagg   8160
gtttgtcctg cctggggtcc tacgtctagt acgcagattc atctttggcc atattggtaa   8220
ggcaccgcca ctgttcctcc catcaactta tcccgccaag aactctatgg cagggatcaa   8280
tggccagagg ttcccaacaa aagacgttca gagcatacct gaaattgatg aaatgtgtgc   8340
ccgcgctgtc aaagagaatt ggcaaactgt gacgccttgc accctcaaaa aacagtattg   8400
ttccaagcct aaaaccagga ccatccttgg taccaacaac ttcattgcct tggctcacag   8460
gtcggcactc agcggtgtca ctcaggcgtt catgaaaaaa gcctggaagt ccccgatcgc   8520
cttggggaaa aacaaattta aggagttgca ctgcactgtc gccggtaggt gcctcgaggc   8580
cgacttggcc tcttgtgatc gcagcacccc ggccatcgtg aggtggtttg ttgccaacct   8640
cctgtacgaa cttgcgggtt gtgaagagta cttgccaagc tatgtgctca attgttgcca   8700
tgacctggtg gcaacgcaaa atggcgcctt cacaaaacgt ggtggcctgt catctggaga   8760
ccccgttacc agtgtgtcca acacagtgta ttcactggtg atttatgctc agcacatggt   8820
gctgtcggct ttgaagatgg gtcatgaaat cggcctcaag ttcctcgagg aacagcttaa   8880
gttcgaggac cttctcgaaa tccagcctat gttggtatat tctgatgacc ttgtattgta   8940
tgctgaaaga cccaccttcc ccaattacca ttggtgggtt gagcaccttg acctgatgct   9000
gggttttaag acagacccaa aaaagactgt cataactgac aaacccagct ttcttggctg   9060
tagaatcgaa gcggggcgac aactggttcc caatcgcgac cgcattctgg ctgctcttgc   9120
atatcacatg aaggcgcaga acgcctcaga gtattatgcg tctgctgccg cgattctgat   9180
ggactcgtgt gcttgcattg accacgatcc tgagtggtat gaggacctca tctgcggcat   9240
tgctcgatgc gcccgccagg atggctacag tttcccaggc ccgccgttct tcatgtccat   9300
gtgggagaag ctgaaaagtc acaatgaagg caagaaattc cgccactgtg gcatttgtga   9360
cgccaaggcc gatcatgcgt ccgcctgtgg gcttgattta tgtctgttcc actcgcactt   9420
tcatcaacac tgccctgtta ctctgagctg cggccatcat gccggttcaa aagaatgccc   9480
acagtgtcag tcacctgttg gagctggtaa atccccccctt gatgcagtgc tgaaacaaat   9540
cccgtacaaa ccccctcgtc ctgtcatcat gaaggtggac aataaaacaa cgacccttga   9600
cccgggaagg tatcagtccc gtcgaggtct tgttgctgtc aagaggggta ttgcaggcaa   9660
tgaggttgat ctcgctgatg gagactatca ggtagtgccc cttttgccaa cctgcaaaga   9720
cataaacatg gtgaaggtgg ctgtcaatgt gctactcagc aagttcatag tggggccgcc   9780
aggttccggc aagacgacct ggctactgag tcaagttcag gatgatgatg tcatctatac   9840
acctacccat cagaccatgt tcgacatagt caatgccctc aaagtctgta ggtattccat   9900
cccagtggct tcagggctcc ctttcccacc gcccgccaga tctggaccgt gggttaggct   9960
cgttgctagc gggcacatcc ctggccgaat atcatacctt gacgaggccg gatattgcaa  10020
tcatctggat attctcagac tgctttctaa gacacctctt gtgtgtttgg gtgaccttca  10080
gcaacttcac cctgtcggct ttgactctta ctgttatgtt tttgatcaaa tgcctcataa  10140
gcagctgacc actatttata gatttggccc caatatctgt tctgccattc aaccttgtta  10200
cagggaaaaa ctcgaatcta aggccaggaa cactagggtg gtttttactg cccggcccgt  10260
ggcttttggt caggtgttga cgccatatca taaagaccgc accggctcag ctataaccat  10320
```

```
agattcatcc cagggagcca cctttgatgt tgtgacgctg catttgccgt cgccagattc  10380
cctgaacaaa tcccgggctc ttgtagctat tactcgggca aggcatgggt tgttcatcta  10440
tgaccctcat aaccaactcc ggaagttttt caacttaaca cctgagcgca ctgattgcaa  10500
cctcgtgttc aaccgcgggg acgagttggt agttttgaat gcagataatg cagtcacgac  10560
tgtggctaag gttttggagg cgggcccgtc tcggtttcga gtatcagatc caaggtgcaa  10620
gtctctttta gccgcttgct cggccagtct ggaaggaggc tgcatgccac tgccgcaagt  10680
ggcacataat ctggggtttt acttctctcc agatagtcca gcatttgcac ctctgccaaa  10740
agagctggca ccacattggc cggtggttac tagtcagaac aaccaggcat ggcccgaccg  10800
acttgtcgct agtatgcggc cagttgatgc ccgctacagc aagcctatgg tcggtgcagg  10860
gtatgtggtt gggccatcca ctttccttgg cactcctggt gtagtgtcat actatctcac  10920
gctgtacatc aggggtgagc cccaggcctt gccggagaca ctcgtctcaa cgggacgtat  10980
agctactgat tgtcgagagt atctcgacgc agctgaggaa gaagcagcta aagaactccc  11040
tcacgcattc attggcgatg tcaaaggtac tacagtgggg gggtgtcacc acattacgtc  11100
aaaatacctt cccaggtcct tgcccaagga ctccgttgcc gtggtcggag tgagttcgcc  11160
cggcaaggct gccaaagccg tgtgtactct caccgatgtg tatcttcccg agctccggcc  11220
atatttgcaa ccggaaacag catcgaaatg ctggaaactt aaactagact tcagggatgt  11280
cagactgatg gtctggaaag gagccaccgc atatttccaa ctggaggggc tcacatggtc  11340
agcgctgccc gactatgcca ggttcattca gctaccaaaa gatgccgttg tgtacattga  11400
tccgtgcata ggaccggcaa cagccaaccg taaggttgtg agaactacag attggcgagc  11460
tgacctggca gtgacaccgt acgactacgg tgctcagagc attttgacta cagcctggtt  11520
cgaggacctt gggccgcagt ggaagatttt agggttgcaa cccttcaagc gggcatttgg  11580
ctttgaaaac actgaggatt gggcgatcct tgcacgtcgc atgaacgacg gcaaggacta  11640
cactgactat aactggaatt gtgttcgaca acgcccacat gccatctacg gacgtgcccg  11700
tgaccatacg tatcactttg cccctggcac tgaactgcaa gtagagctag gtaaaccccg  11760
gctaccgcct gagcaagtac cgtgaatcta gagtgatgca atggggtcac tgtggagtaa  11820
aatcagtcaa ctgttcgtgg atgccttcac tgagttcctc gttagtgtgg ttgatattgt  11880
catcttcctt gccatactgt ttgggttcac cgttgcaggg tggttactgg tctttttttt  11940
cagagtggtt tgctccgcgc ttctccgttc gcgctctgcc attcactctt ccgaactatc  12000
gaaggtccta tgagggcttg ctacctaatt gcagaccgga tgttccacaa ttcgcagtca  12060
agcacccatt gggtatactt tggcacatgc gagtttccca cttaattgac gaaatggtct  12120
ctcgccgcat ttaccagacc atggaacatt caggtcaagc ggcctggaag caggtggtta  12180
gtgaagctac tctcacaaga ctgtcaaagc tcgacatagt tctccacttc caacacctgg  12240
ccgcaataga ggcggattct tgccgcttcc tcagctcacg acttgtgatg ctgaaaaatc  12300
ttgccgttgg caatatgagc ctacagtaca acaccacgtt ggaccgcgtt gagctcatct  12360
tcccaacacc aggtacgagg cccaaattga ccgattttag acaatggctc gtcagtgtgc  12420
acgcttctat tttttcctct gtggcctcat cagttacctt gttcatagtg ctttggcttc  12480
gaattccagc tctacgctat gtttttggtt tccattggcc cacggcaaca catcattcga  12540
gctaaccatc aattacacta tatgtaagcc ctgtctcacc agtcaagcgg ctcgacaaag  12600
gctcgaaccc ggtcgcaaca tgtggtgcaa aataggacac accacgtgtg aggagcgtga  12660
```

-continued

```
ccatgatgag ttgtcaatga ccattccgtc cgggtacgat aacctcaaac ttgagggtta  12720
ttacgcttgg ctggcttttt tgtccttttc ttacgcagcc caatttcatc cagagttgtt  12780
cggaataggg aatgtgtcac gcgtcttcgt ggataaacgg caccagttca tctgtgccga  12840
gcacgacgga caaaattcaa ccgtatccac cgaacataat atttccgcat tgtatgcggc  12900
gtactaccac caccaggtag acgggggcaa ttggttccac ctggaatggc tgcggccttt  12960
cttttcctcc tggctagtac tcaatatttc atggtttctg aggcgttcgc ctgcaagccc  13020
tgtttctcga cgcatttatc agatattgag accaacacga ccgcggctgc cggtttcatg  13080
gtccttcagg acatcaactg tttccacagt ggctcagagg cacaaacgac tggtcccatc  13140
agaaagtcgt cccaatgccg tgaagccgtc ggcactcccc agtacatcaa gataacggcc  13200
aatgtgaccg acgaatcata cttgtacaac gcggacttgc tgatgcttttc tgcgtgcctt  13260
ttctacgcct cagagatgag cgagaaaggc tttaaagtca tttttgggaa tgtctctggc  13320
gttgtctccg cttgtgtcaa ttttacagat tatgtggccc atgtgaccca acatacccag  13380
cagcatcatt tggtaatcaa tcacattcgg ttgctacatt tcctgacacc atcagcaatg  13440
aggtgggcta caaccattgc ttgtttgttc gccattctct tggcgatatg agatgttctc  13500
acaaatcggg gtgtttcttg actccgcact cttgcttctg gtggcttttt ttgctgtgta  13560
ccggcttgtc ctggtccttt gccgatggca acggcaacag ctcgacatac caatatatat  13620
ataacttgac gatatgcgag ctgaatggga ccgaatggct gtccgaccat tttaattggg  13680
cagtcgagac ttttgtgctc tacccagtgg cgactcatat cctctcactg ggtttcctca  13740
cgacaagtca tttccttgat gcgttcggtc ttggagctgt gtcagttaca gggttttgtg  13800
gcgggcggta cgtgctcagc agcgtgtacg gcgcttgtgc actagcagcg ctcgtatgtt  13860
ttgttatccg tgctgccaaa aattgtatgg cttgccgcta tgctcgtacc cggtttacca  13920
acttcattgt ggatgaccgg gggagaatcc atcggtggag gtctccaata gtggtggaaa  13980
aattaggtaa agctgacgtc ggcggcgacc ttgtcaccat caaacatgtc atcctcgaag  14040
gagtcaaagc tcaacccttg acgaggactt cggccgagca atgggaggcc tagataattt  14100
ctgcaacgat cccaccgccg cacaaaagct tgtgctagcc tttagcatca catatacacc  14160
catcatgata tacgccctta aggtgtcacg cggccgactc ttggggttgt tgcacatctt  14220
gatatttctg aactgttctt tcacgttcgg atacatgaca tatatgcatt ttgaatccac  14280
caaccgtgtc gcgcttacca tgggggggcgt tgtcgccctt ctgtggggcg tttatagttt  14340
catagagtca tggaagttta tcacttccag atgcagattg tgttgcctag gccggcgata  14400
cattctggcc cctgcccacc acgtagaaag tgctgcaggc ctccatccga tcccagcgtc  14460
tggtaaccaa gcatacgctg tgagaaagcc cggactaaca tcagtgaacg gcactctggt  14520
accaggactt cgaggcctcg tgctgggcgg caaacgagct gttaaacgag gagtggttaa  14580
cctcgtcaag tatggccggt aaaaaccaga gccagaagaa aaagaaaaat ccagctccaa  14640
tggggaatgg ccagtcagtc aatcaactgt gccagctgct gggcacaatg ataaagtccc  14700
agcgccagcg acccagggga ggacaggcta aaaagaaaaa gcctgagaag ccacatttcc  14760
ccctggctgc tgaagatgac gtccggcacc atctcaccca gaccgagcgc tccctttgct  14820
tgcaatcgat ccagacggct tttaatcaag gcgcaggaac tgcgtcgctt tcatccagcg  14880
ggaagatcgg ttttcaggtt gagtttatgc taccggttgc tcatacagtg cgcctgattc  14940
gcgtgacttc tacatccgcc ggtcaggatg caaattaatt tgatagtcag gtgaatggcc  15000
gcgattggcg tgtggcctct gagtcaccta ttcaattagg gcgatcacat gggggtcaga  15060
```

cttaattagg caggaaccat gtgaccgaaa tt 15092

<210> SEQ ID NO 3
<211> LENGTH: 15092
<212> TYPE: DNA
<213> ORGANISM: Artificial Sequence
<220> FEATURE:
<223> OTHER INFORMATION: PRRS virus isolate 96V198 - passage 9

<400> SEQUENCE: 3
atgatgtgta gggtattccc cctacataca cgacacttct agtgtttgtg tgccttggag 60
gcgtgggtat agccccgccc cacctcttgg cccctgttct agcccaacag gtatccttct 120
ctctcggggc gagcgcgccg cctgctgctc ccttgcagca ggaaggacct cccgagtatt 180
tccggagagc acctgcttta cgggatctcc accctttaac catgtctggg acgttctccc 240
ggtgcatgtg caccccggct gcccgggtat tttggagcgc cggccaagtc tattgcacac 300
ggtgtctcag tgcacggtct cttctctctc cggagcttca ggacactgac ctcgctgcaa 360
ttggcttgtt ttacaagcct aaagacaagc ttcactggaa agtccctatc ggcatccctc 420
aggtggagtg tactccgtcc gggtgctgtt ggctctcagc catcttcccc ttggcgcgca 480
tgacctccgg caatcacaac tttctccaac gacttgtgaa ggttgctgat gttttgtacc 540
gtgacggctg cttggcacct cgacaccttc gcgaactcca agtttacgag cgcggctgca 600
actggtaccc gatcacgggg cccgtgcccg ggatgggttt gtacgcgaac tccatgcacg 660
tgtccgacca accgtttcct ggtgccgctc atgtgttaac gaactcacct ctgcctcagc 720
aggcttgtcg acagccgttt tgtccatttg aggaggttca ttccgacgta tacaggtgga 780
agaaattcgt gatttttgtg gattcctctt ctgacggccg atctcgcatg atgtggacac 840
caggatccga cgactcggct gccttagaag tattgccacc tgaactagaa tgtcgagtcg 900
aaatcctcgt tcggagtttt cctgcccacc accctgtcga catcaccaac tgggagctca 960
ctgagtcccc tgagcacggt tttccttca gcacgtctca ttcttgtggt taccttgccc 1020
aagaccctga cgtgtttgat ggtaagtgtt ggctttcttg ctttttgggc ctgccgaccg 1080
aagtgtggcg tcatgaggag tatctagcta acgccttcgg ttaccaaacc aagtggggcg 1140
tgcatggtaa gtacctccag cgcaggcttc aggtccgcgg catgcgtgct gtagttgatc 1200
ctgatggtcc catccacgtt gaagcgctgt cttgccccca gtcttggatc aggcacctga 1260
ctctaaatga tgacgtcacc ccaggatttg ttcgcctaac atcccttcgc attgagccga 1320
acacagagcc tactactttc cggatctttc ggtttggagc gcataagtgg tatggcgctg 1380
ccggcaaacg ggctcgtgct aagcgtgccg ctaaaggtga gaagaattca gctcccaccc 1440
ccaaggtcgc cctgccggtc cccacctatg gaattaccac ctactctcca ccgacagacg 1500
ggtcttgtgg ttggcatgtc cttgccgcca taatgaaccg gatgataaat ggtgacttca 1560
cgtcccctct gactccgtac aacagaccag aggatgattg ggcttctgat tatgatcttg 1620
ctcaggcaat ccaatgtcta caactgcctg ctaccgtggt ccggagtcgc gcctgtccta 1680
acgccaagta cctcataaaa ctcaacggag tccactggga ggtagaggtg aggtcaggaa 1740
tggctcctcg ctctctttct cgtgaatgtg tggttggcgt ttgctctgaa ggttgtgttg 1800
caccgcctta tccagcagac gggctaccag aacgagcact cgaggccttg gcgtctgctt 1860
acaggttacc ctctgattgt gttagctctg gcattgctga ctttcttgct aacccacctc 1920
ctcaggaatt ctggaccctc gacaaaatgt tgacctcccc gtcaccagag cggtccggct 1980

-continued

```
tctctagttt gtataaatta ctattagagg ttgttccgca aaaatgcggt gccacggaag   2040
gggctttcgt ctatgctgtt gagagaatgt tgaaggattg tccgagctcc aaacaggcca   2100
tggcccttct ggcaaaaatt aaagttccat cctcaaaggc cccgtctgtg tcccttgacg   2160
agtgtttccc tacggatgtt tcagccgact tcgagccagc atctcaggaa aggccccaaa   2220
gttccggtgc tgctgttgtc ctgtgttcac cggaagtaaa agagttcgaa gaagcagccc   2280
cagaagaagt tcaagagagt ggccacaagg tcgcccgctc tgcatttgtt gccgagggtc   2340
ctaacaatga acaggtaccg atggctgccg gcgagcaact gaagcccggt ggtcgcgttt   2400
tggcggtcgg gaatgctcat gaaggtgttc tggcctcaac tagttcgact aacctgatag   2460
gcgggaactt ccccccttca gactccatga aagagagcat gctcaatagc tgggaagacg   2520
aaccactgga tttgtcccaa ccggcaccag ctgttacaat gacccttgtg agagagcaaa   2580
cacccgacaa cctgggtcct gatgccggtg ccttccccgt caccgttcga aaatttgtcc   2640
cgacagggcc tacactccgt catgttgagc actgcggcac ggagtcaggc gacagcagtt   2700
cgcccttgga tctgtcttat gcgcaaaccc tggaccagcc tttaaatcta tccttggccg   2760
cttggccagt gagggccacc gcgtctgacc ctggctgggt ccacggtagg cgtgagccta   2820
tctttgtaaa gcctcgagat gctttctctg acggcgattc agcccttcag ctcggggagc   2880
tgtctgaatc cggctccgtc atcgagtttg accggacaag aaatgctccg gcggtcgacg   2940
cccctgttga cttgacggct tcgaacaagg ccctctctgt ggttgatcct ttcgaatttg   3000
ccgaactcaa gcgcccgcgt ttttccgcac aagccttaat tgaccgaggc ggtccacttg   3060
ccgacgtcca tgcaaaaata aagaaccggg tatatgaaca gtgcctccag gcttgtgagc   3120
ctggcagtcg cgcaacccca gccaccaaga agtggctcga taaaatgtgg gatagggtgg   3180
acatgaagac ttggcgctgt acctcgcagt tccaagctgg tcgcattctt gcgtccctta   3240
aattcctccc tgacatgatt caggacacac cacctcctgt tcctaggaag aatcgggcta   3300
gtgataatgc cggcctgaag cgactggtgg cgcagtggga cagaaaattg agtgcaaccc   3360
cccccttcaaa accggttgga ccaacacttg accaaattgt cccttcgccc acgggtaccc   3420
agcaagaaga tgtcacttcc tccgatgggc catctcatgc gccggatcct cctagtcgaa   3480
tgagcacgag tgggagttgg aagggccttg tgctctctgg tacccgtctc gcggggtcca   3540
ttagtcagca tttcatgaca tgggtttttg aggttttctc ccatctccca gcttttgcac   3600
tcacactttt ctcgccgagg ggctctatgg cttcaggtga ttggatgttt gcaggtgttg   3660
ttttacttgc tctcctgctc tgtcgttctt acccagtatt cgggtgcctt cccttattgg   3720
gtgtcctttc tggctctgtg cggcgcgttc gtctgggggt ttttggttct tggatggctt   3780
tcgctgtatt tttattctcg actccatcca acccagtcgg ttcttcttgt gaccacgatt   3840
cgccggagtg tcatgctgag cttttggctc ttgagcagcg ccaactttgg gaacctgtgc   3900
gcggccttgt ggtcggcccc tcgggcctct tatgtgtcat tcttggcaag ctactcggtg   3960
ggtcacgtta tctctggcat gttttcttac gtttatgcat gcttgcagat ttggcccttt   4020
ctcttgttta tgtggtgtcc caggggcgtt gtcacaagtg ttggggaaag tgtataagaa   4080
cagctccggc ggaggtggct ctcaatgtgt tccctttctc gcgcgctacc cgtagctctc   4140
ttgtgtcctt gtgcgatcgg ttccaagcgc caaaaggggt tgatcctgtg tacttggcaa   4200
cgggttggcg cgggtgttgg tgtggtgaga gtcccattca tcaaccgcac caaaaaccca   4260
tagcttatgc taatctggat gaaaagaaaa tatctgccca aacggtggtt gctgtcccac   4320
acgatcccag tcaggccatc aagtgcctga aagttttgca ggcgggagga gccatcgtgg   4380
```

```
accagcccac acctgaggtc gtccgtgtat ccgaaatccc cttctcagcc ccatttttcc   4440
caaaagttcc agtcaaccca gattgtaagg ttgtggtgga ttcggacact tttgtggctg   4500
cggttcgctg cggctactcg acagcacaac tggtcttagg ccagggcaac tttgccaagt   4560
taaatcagat tcccctcagg agctccatct ccaccaaagc gattggcggg gcctcttaca   4620
cccttgctgt ggctcaagtt tctgtgtgga ctcttgttca cttcatcctc ggtctttggt   4680
tcacgtcacc ccaagtgtgt ggccgaggaa cctctgactc atggtgttca aatccttttt   4740
cataccctac ctatggcccc ggggttgtgt gctcctctcg actttgtgtg tctgccgacg   4800
gggtcactct accattgttc tcagccgtgg ctcaactctc cggtagagag gtggggattt   4860
ttattttggt gctcgtctcc ttgatggctt tggcccaccg catggccctt aaggcagaca   4920
tgttgatggt ctttctggct ttttgtgctt acgcctggcc catgagctcc tggttgattt   4980
gcttctttcc tacactcttg aagtgggtta ccctccaccc tcttactatg ctttgggtgc   5040
actcattctt ggtgttttgt ctgccagcag ccggcatcct ctcactaggg ataactggcc   5100
ttctttgggc ggttggccgc tttactcagg ttgccggaat tattacacct tatgacatcc   5160
accagtacac ctctgggcca cgtggcgctg cagctgtggc cacagcccca gaaggcactt   5220
atatggccgc cgtccggaga gctgctttaa ctgggcgaac tttaatcttc accccgtctg   5280
cagttggatc ccttctcgaa ggagctttca ggactcataa accttgtctt aacaccgtaa   5340
atgttgtagg ctcttccctt ggttccggcg gggttttcac tattgacggc agaaaaattg   5400
ttgtcactgc tgcccatgtg ttgaacggcg acacagctag agtcaccggc gactcctaca   5460
accgcatgca tactttcaag accaatggtg attatgcctg gtcccatgct gatgactggc   5520
ggggcgttgc ccctgcggtc aaggttgcga aggggtaccg cggtcgtgcc tactggcaaa   5580
catcaactgg cgtcgaaccc ggtgttattg gggaagggtt cgccttctgt ttcaccacct   5640
gtggcgattc ggggtcaccc gtcatctcag aatccggtga tctcattgga atccataccg   5700
gttcaaataa acttggttct ggtcttgtga caacccctga aggggagaca tgtaccatca   5760
aagaaaccaa gctctctgac ctctccagac atttcgcagg cccaagcgtt cctcttgggg   5820
atattaaatt gagtccagcc atcatccctg atataacatc cattccgagt gacttggcat   5880
cgctcctatc ctccgtccct gtagtggaag gcggcctctc gaccgttcaa cttttgtgtg   5940
tctttttcct actttggcgc atgatgggcc atgcctggac tcccattgtt gccgtgggtt   6000
tctttttact gaatgaaatt cttccagcag ttttggtccg agccgtgttt tcttttgcac   6060
tttttgtgct tgcatgggcc acccccctggt ctgcacaggt gttgatgatt agactcctca   6120
cggcatctct caaccgcaat aagctttctc tggcgttcta cgcactcggg ggggtcgtcg   6180
gtttggccgc tgaaatcggg acttttgctg gcaaattgcc tgaattgtct caaacccttt   6240
cgacatactg cttcttacct agggtccttg ctatgaccag ttgtgttccc accatcatca   6300
ttggtggact ccatgccctc ggtgtaattc tgtggttgtt caaataccgg tgcctccaca   6360
acatgctcgt tggtgatggg agtttttcaa gcgccttctt cctacggtat tttgcagagg   6420
gtaatctcag aaaaggtgtt tcgcagtcct gtggcatgaa taacgagtcc ctgacggctg   6480
ctttggcttg caagttgtca cggggctgacc ttgatttttt gtccagctta acgaacttca   6540
agtgctttgt atctgcttcg aatatgaaaa atgctgccgg ccagtacatt gaagcggcgt   6600
atgccaaggc cctgcgccaa gagttggcgt ctctagttca gattgacaaa atgaaaggag   6660
ttttgtccaa actcgaggcc tttgctgaaa cagctactcc gtcccttgac ataggtgacg   6720
```

```
tgattgttct gcttgggcaa catccacacg gatctatcct tgatattaat gtggggactg   6780
agaggaaaac tgtgtccgtg caagagaccc ggagcctagg cggttccaaa ttcagtgttt   6840
gtactgtcgt gtctaacaca cccgtggacg ccttaaccgg catcccactc cagacaccaa   6900
cccctctttt tgagaatggt ccgcgtcatc gcagcgaaga agacgatctt aaagtcgaga   6960
ggatgaagaa acactgtgtg tccctcggct tccacaacat caatggcaaa gtttactgca   7020
agatttggga caagtccacc ggtgacacct tttacacgga tgattcccgg tatacccacg   7080
accatgctct tcaggacagg tcagccgact acagagacag ggactatgag ggtgtgcaaa   7140
ccgccccccca acagggattt gatccaaagt ctgaaacccc tgtcggcact gttgtgatcg   7200
gcggtattac gtataacagg tatctgacta agggtaagga ggttctggtt cccaagcccg   7260
acaattgcct tgaagctgcc aagctgtctc ttgagcaagc tctcgctggg atgggccaaa   7320
cttgcgacct tacagctgcc gaggtggaaa agttaaagcg catcatcagt caactccaag   7380
gtttgaccac tgaacaggct ttaaactgct agccgctagc ggcttgaccc gctgtggccg   7440
cggcggctta gttgttactg aaacggcggt aaaaattgta agataccaca gcagaacttt   7500
caccttgggc cctttggacc taaaagtcgc ttctgaggtg gaggtgaaga gatcaactga   7560
gcagggccac gctgttgtgg caaacctatg ttctggtgtt gtattgatga gacctcaccc   7620
accgtccctt gttgacgttc ttctgaaacc cggacttgac acaacacccg gcattcaacc   7680
ggggcatggg gccgggaata tggcgtgga cggttccatt tgggattttg aaaccgcacc   7740
cacaaaggca gaactcgagt tgtccaagca aataatccaa gcatgtgaag tcaggcgcgg   7800
ggatgccccg aacctccaac tcccttacaa gctctgtcca gttagggggg atcctgagcg   7860
gcataaaggc cgccttatca ataccaggtt tggagatttg ccttacaaga ctcctcaaga   7920
caccaagtcc gcaatccacg cggcttgttg cctgcacccc aacggggctc ccgtgtctga   7980
tggtaaatcc acattaggca ccactcttca acacggtttc gagctttatg tccctactgt   8040
gccctatagt gtcatggagt accttgattc acgccctgac acccccttta tgtgtaccaa   8100
acatggtact cccgaggctg ctgcagagga ccttcgaaaa tatgacttat ccacccaagg   8160
gtttgtcctg cctggggtcc tacgtctagt acgcagattc atctttggcc atattggtaa   8220
ggcaccgcca ctgttcctcc catcaactta tcccgccaag aactctatgg cagggatcaa   8280
tggccagagg ttcccaacaa aagacgttca gagcatacct gaaattgatg aaatgtgtgc   8340
ccgcgctgtc aaagagaatt ggcaaactgt gacgccttgc accctcaaaa aacagtattg   8400
ttccaagcct aaaaccagga ccatccttgg taccaacaac ttcattgcct tggctcacag   8460
gtcggcactc agcggtgtca ctcaggcgtt catgaaaaaa gcctggaagt ccccgatcgc   8520
cttggggaaa aacaaattta aggagttgca ctgcactgtc gccggtaggt gcctcgaggc   8580
cgacttggcc tcttgtgatc gcagcacccc ggccatcgtg aggtggtttg ttgccaacct   8640
cctgtacgaa cttgcgggtt gtgaagagta cttgccaagc tatgtgctca attgttgcca   8700
tgacctggtg gcaacgcaaa atggcgcctt cacaaaacgt ggtggcctgt catctggaga   8760
ccccgttacc agtgtgtcca acacagtgta ttcactggtg atttatgctc agcacatggt   8820
gctgtcggct ttgaagatgg gtcatgaaat cggcctcaag ttcctcgagg aacagcttaa   8880
gttcgaggac cttctcgaaa tccagcctat gttggtatat tctgatgacc ttgtattgta   8940
tgctgaaaga cccaccttcc ccaattacca ttggtgggtt gagcaccttg acctgatgct   9000
gggttttaag acagacccaa aaaagactgt cataactgac aaacccagct ttcttggctg   9060
tagaatcgaa gcggggcgac aactggttcc cagtcgcgac cgcattctgg ctgctcttgc   9120
```

```
atatcacatg aaggcgcaga acgcctcaga gtattatgcg tctgctgccg cgattctgat   9180
ggactcgtgt gcttgcattg accacgatcc tgagtggtat gaggacctca tctgcggcat   9240
tgctcgatgc gcccgccagg atggctacag tttcccaggc ccgccgttct tcatgtccat   9300
gtgggagaag ctgaaaagtc acaatgaagg caagaaattc cgccactgtg gcatttgtga   9360
cgccaaggcc gatcatgcgt ccgcctgtgg gcttgattta tgtctgttcc actcgcactt   9420
tcatcaacac tgccctgtta ctctgagctg cggccatcat gccggttcaa aagaatgccc   9480
acagtgtcag tcacctgttg gagctggtaa atccccccctt gatgcagtgc tgaaacaaat   9540
cccgtacaaa cccccctcgtc ctgtcatcat gaaggtggac aataaaacaa cgacccttga   9600
cccgggaagg tatcagtccc gtcgaggtct tgttgctgtc aagaggggta ttgcaggcaa   9660
tgaggttgat ctcgctgatg gagactatca ggtggtgccc cttttgccaa cctgcaaaga   9720
cataaacatg gtgaaggtgg ctgtcaatgt gctactcagc aagttcatag tggggccgcc   9780
aggttccggc aagacgacct ggctactgag tcaagttcag gatgatgatg tcatctatac   9840
acctacccat cagaccatgt tcgacatagt caatgccctc aaagtctgta ggtattccat   9900
cccagtggct tcagggctcc ctttcccacc gcccgccaga tctggaccgt gggttaggct   9960
cgttgctagc gggcacatcc ctggccgaat atcatacctt gacgaggccg gatattgcaa  10020
tcatctggat attctcagac tgctttctaa gacacctctt gtgtgtttgg gtgaccttca  10080
gcaacttcac cctgtcggct ttgactctta ctgttatgtt tttgatcaaa tgcctcataa  10140
gcagctgacc actatttata gatttggccc caatatctgt tctgccattc aaccttgtta  10200
cagggaaaaa ctcgaatcta aggccaggaa cactagggtg gtttttactg cccggcccgt  10260
ggcttttggt caggtgttga cgccatatca taaagaccgc accggctcag ctataaccat  10320
agattcatcc cagggagcca cctttgatgt tgtgacgctg catttgccgt cgccagattc  10380
cctgaacaaa tcccgggctc ttgtagctat cactcgggca aggcatgggt tgttcatcta  10440
tgaccctcat aaccaactcc ggaagttttt caacttaaca cctgagcgca ctgattgcaa  10500
cctcgtgttc aaccgcgggg acgagttggt agttttgaat gcagataatg cagtcacgac  10560
tgtggctaag gttttggagg cgggcccgtc tcggtttcga gtatcagatc caaggtgcaa  10620
gtctctttta gccgcttgct cggccagtct ggaaggaggc tgcatgccac tgccgcaagt  10680
ggcacataat ctggggtttt acttctctcc agatagtcca gcatttgcac ctctgccaaa  10740
agagctggca ccacattggc cggttgttac tagtcagaac aaccaggcat ggcccgaccg  10800
acttgtcgct agtatgcggc cagttgatgc ccgctacagc aagcctatgg tcggtgcagg  10860
gtatgtggtt gggccatcca ctttccttgg cactcctggt gtagtgtcat actatctcac  10920
gctgtacatc aggggtgagc cccaggcctt gccggagaca ctcgtctcaa cgggacgtat  10980
agctactgat tgtcgagagt atctcgacgc agctgaggaa gaagcagcta aagaactccc  11040
tcacgcattc attggcgatg tcaaaggtac tacagtgggg gggtgtcacc acattacgtc  11100
aaaatacctt cccaggtcct tgcccaagga ctccgttgcc gtggtcggag tgagttcgcc  11160
cggcaaggct gccaaagccg tgtgtactct caccgatgtg tatcttcccg agctccggcc  11220
atatttgcaa ccggaaacag catcgaaatg ctggaaactt aaactagact tcagggatgt  11280
cagactgatg gtctggaaag gagccaccgc atatttccaa ctggaggggc tcacatggtc  11340
agcgctgccc gactatgcca ggttcattca gctaccaaaa gatgccgttg tgtacattga  11400
tccgtgcata ggaccggcaa cagccaaccg taaggttgtg agaactacag attggcgagc  11460
```

-continued

```
tgacctggca gtgacaccgt acgactacgg tgctcagagc attttgacta cagcctggtt  11520
cgaggacctt gggccgcagt ggaagatttt agggttgcaa cccttcaagc gggcatttgg  11580
ctttgaaaac actgaggatt gggcgatcct tgcacgtcgc atgaacgacg gcaaggacta  11640
cactgactat aactggaatt gtgttcgaca acgcccacat gccatctacg gacgtgcccg  11700
tgaccatacg tatcactttg cccctggcac tgaactgcaa gtagagctag gtaaaccccg  11760
gctaccgcct gagcaagtac cgtgaatcta gagtgatgca atggggtcac tgtggagtaa  11820
aatcagtcaa ctgttcgtgg atgccttcac tgagttcctt gttagtgtgg ttgatattgt  11880
catcttcctt gccatactgt ttgggttcac cgttgcaggg tggttactgg tcttttttttt  11940
cagagtggtt tgctccgcgc ttctccgttc gcgctctgcc attcactctt ccgaactatc  12000
gaaggtccta tgagggcttg ctacctaatt gcagaccgga tgttccacaa ttcgcattca  12060
agcacccatt gggtatgttt tggcacatgc gagtttccca cttaattgac gaaatggtct  12120
ctcgccgcat ttaccagacc atggaacatt caggtcaagc ggcctggaag caggtggtta  12180
gtgaagctac tctcacaaga ctgtcaaagc tcgacatagt tctccacttc caacacctgg  12240
ccgcaataga ggcggattct tgccgcttcc tcagctcacg acttgtgatg ctgaaaaatc  12300
ttgctgttgg caatatgagc ctacagtaca acaccacgtt ggaccgcgtt gagctcatct  12360
tcccaacacc aggtacgagg cccaaattga ccgattttag acaatggctc gtcagtgtgc  12420
acgcttctat tttttcctct gtggcctcat cagttacctt gttcatagtg ctttggcttc  12480
gaattccagc tctacgctat gtttttggtt tccattggcc cacggcaaca catcattcga  12540
gctaaccatc aattactcta tatgtaagcc ctgtctcacc agtcaagcgg ctcgacaaag  12600
gctcgaaccc ggtcgcaaca tgtggtgcaa aataggacac accacgtgtg aggagcgtga  12660
ccatgatgag ttgtcaatga ccattccgtc cgggtacgat aacctcaaac ttgagggtta  12720
ttacgcttgg ctggcttttt tgtccttttc ttacgcagcc caatttcatc cagagttgtt  12780
cggaataggg aatgtgtcac gcgtcttcgt ggataaacgg caccagttca tctgtgccga  12840
gcacgacgga caaaattcaa ccgtatccac cgaacataat atttccgcat tgtatgcggc  12900
gtactaccac caccaggtag acgggggcaa ttggttccac ctggaatggc tgcggccttt  12960
cttttcctcc tggctagtac tcaatatttc atggtttctg aggcgttcgc ctgcaagccc  13020
tgtttctcga cgcatttatc agatattgag accaacacga ccgcggctgc cggtttcatg  13080
gtccttcagg acatcaactg tttccacagt ggctcagagg cacaaacgac tggtcccatc  13140
agaaagtcgt cccaatgccg tgaagccgtc ggcactcccc agtacatcaa gataacggcc  13200
aatgtgaccg acgaatcata cttgtacaac gcggacttgc tgatgctttc tgcgtgcctt  13260
ttctacgcct cagagatgag cgagaaaggc tttaaagtca tttttgggaa tgtctctggc  13320
gttgtctccg cttgtgtcaa ttttacagat tatgtggccc atctgaccca acatacccag  13380
cagcatcatt tggtaaccaa tcacattcgg ttgctacatt tcctgacacc atcagcaatg  13440
aggtgggcta caaccattgc ttgtttgttc gccattctct tggcgatatg agatgttctc  13500
acaaatcggg gtgtttcttg actccgcact cttgcttttg gtggtttttt ttgctgtgta  13560
ccggcttgtc ctggtccttt gccgatggca acggcaacag ctcgacatac caatatatat  13620
ataacttgac gatatgcgag ctgaatggga ccgaatggct gtccgaccat tttaattggg  13680
cagtcgagac ttttgtgctc tacccagtgg cgactcatat cctctcactg ggtttcctca  13740
cgacaagtca tttccttgat gcgttcggtc ttggagctgt gtcaattaca gggttttgtg  13800
gcgggcggta cgtgctcagc agcgtgtacg gcgcttgtgc actagcagcg ctcgtatgtt  13860
```

```
ttgttatccg tgctgccaaa aattgtatgg cttgccgcta tgctcgtacc cggtttacca  13920

acttcattgt ggatgaccgg gggagaatcc atcggtggag gtctccaata gtggtggaaa  13980

aattaggtaa agctgacgtc ggcggcgacc ttgtcaccat caaacatgtc atcctcgaag  14040

gagtcaaagc tcaacccttg acgaggactt cggccgagca atgggaggcc tagataattt  14100

ctgcaacgat cccaccgccg cacaaaagct tgtgctagcc tttagcatca cgtatacacc  14160

catcatgata tacgccctta aggtgtcacg cggccgactc ttggggttgt tgcacatctt  14220

gatatttctg aactgttctt tcacgttcgg atacatgaca tatatgcatt ttgaatccac  14280

caaccgtgtc gcgcttacca tggggggcgt tgtcgccctt ctgtggggcg tttatagttt  14340

catagagtca tggaagttta tcacttccag atgcagattg tgttgcctag gccggcgata  14400

cattctggcc cctgcccacc acgtagaaag tgctgcaggc ctccatccga tcccagcgtc  14460

tggtaaccaa gcatacgctg tgagaaagcc cggactaaca tcagtgaacg gcactctggt  14520

accaggactt cgaggcctcg tgctgggcgg caaacgagct gttaaacgag gagtggttaa  14580

cctcgtcaag tatggccggt aaaaaccaga gccagaagaa aaagaaaaat ccagctccaa  14640

tggggaatgg ccagtcagtc aatcaactgt gccagctgct gggcacaatg ataaagtccc  14700

agcgccagcg acccagggga ggacaggcta aaaagaaaaa gcctgagaag ccacatttcc  14760

ccctggctgc tgaagatgac gtccggcacc atctcaccca gaccgagcgc tccctttgct  14820

tgcaatcgat ccagacggct tttaatcaag gcgcaggaac tgcgtcgctt tcatccagcg  14880

ggaagatcgg ttttcaggtt gagtttatgc taccggttgc tcatacagtg cgcctgattc  14940

gcgtgacttc tacatccgcc ggtcaggatg caaattaatt tgatagtcag gtgaatggcc  15000

gcgattggcg tgtggcctct gagtcaccta ttcaattagg gcgatcacat gggggtcaga  15060

cttaattagg caggaaccat gtgaccgaaa tt                                15092
```

<210> SEQ ID NO 4
<211> LENGTH: 15092
<212> TYPE: DNA
<213> ORGANISM: Artificial Sequence
<220> FEATURE:
<223> OTHER INFORMATION: PRRS virus isolate 96V198 - passage 14

<400> SEQUENCE: 4

```
atgatgtgta gggtattccc cctacataca cgacacttct agtgtttgtg tgccttggag     60

gcgtgggtat agccccgccc cacctcttgg cccctgttct agcccaacag gtatccttct    120

ctctcggggc gagcgcgccg cctgctgctc ccttgcagca ggaaggacct cccgagtatt    180

tccggagagc acctgcttta cgggatctcc accctttaac catgtctggg acgttctccc    240

ggtgcatgtg caccccggct gcccgggtat tttggagcgc cggccaagtc tattgcacac    300

ggtgtctcag tgcacggtct cttctctctc cggagcttca ggacactgac ctcgctgcaa    360

ttggcttgtt ttacaagcct aaagacaagc ttcactggaa agtccctatc ggcatccctc    420

aggtggagtg tactccgtcc gggtgctgtt ggctctcagc catcttcccc ttggcgcgca    480

tgacctccgg caatcacaac tttctccaac gacttgtgaa ggttgctgat gttttgtacc    540

gtgacggctg cttggcacct cgacaccttc gcgaactcca agtttacgag cgcggctgca    600

actggtaccc gatcacgggg cccgtgcccg ggatgggttt gtacgcgaac tccatgcacg    660

tgtccgacca accgttccct ggtgccgctt atgtgttaac gaactcacct ctgcctcagc    720

aggcttgtcg acagccgttt tgtccatttg aggaggttca ttccgacgta tacaggtgga    780
```

-continued

```
agaaattcgt gatttttgtg gattcctctt ctgacggccg atctcgcatg atgtggacac    840
caggatccga cgactcggct gccttagaag tattgccacc tgaactagaa tgtcgagtcg    900
aaatcctcgt tcggagtttt cctgcccacc accttgtcga catcaccaac tgggagctca    960
ctgagtcccc tgagcacggt tttccttca gcacgtctca ttcttgtggt taccttgccc   1020
aagaccctga cgtgtttgat ggtaagtgtt ggctttcttg ctttttgggc ctgccgaccg   1080
aagtgtggcg tcatgaggag catctagcta acgccttcgg ttaccaaacc aagtggggcg   1140
tgcatggtaa gtacctccag cgcaggcttc aggtccgcgg catgcgtgct gtagttgatc   1200
ctgatggtcc catccacgtt gaagcgctgt cttgcccca gtcttggatc aggcacctga   1260
ctctaaatga tgacgtcacc ccaggatttg ttcgcctaac atcccttcgc attgagccga   1320
acacagagcc tactactttc cggatctttc ggtttggagc gcataagtgg tatggcgctg   1380
ccggcaaacg ggctcgtgct aagcgtgccg ctaaaggtga gaagaattca gctcccaccc   1440
ccaaggtcgc cctgccggtc cccacctatg gaattaccac ctactctcca ccgacagacg   1500
ggtcttgtgg ttggcatgtc cttgccgcca taatgaaccg gatgataaat ggtgacttca   1560
cgtcccctct gactccgtac aacagaccag aggatgattg ggcttctgat tatgatcttg   1620
ctcaggcaat ccaatgtcta caactgcctg ctaccgtggt ccggagtcgc gcctgtccca   1680
acgccaagta cctcataaaa ctcaacggag tccactggga ggtagaggtg aggtcaggaa   1740
tggctcctcg ctctctttct cgtgaatgtg tggttggcgt ttgctctgaa ggttgtgttg   1800
caccgcctta tccagcagac gggctaccag aacgagcact cgaggccttg gcgtctgctt   1860
acaggttacc ctctgattgt gttagctctg gcattgctga ctttcttgct aacccacctc   1920
ctcaggaatt ctggaccctc gacaaaatgt tgacctcccc gtcaccagag cggtccggct   1980
tctctagttt gtataaatta ctattagagg ttgttccgca aaaatgcggt gccacggaag   2040
gggctttcgt ctatgctgtt gagagaatgt tgaaggattg tccgagctcc aaacaggcca   2100
tggcccttct ggcaaaaatt aaagttccat cctcaaaggc cccgtctgtg tcccttgacg   2160
agtgtttccc tacggatgtt tcagccgact tcgagccagc atctcaggaa aggccccaaa   2220
gttccggtgc tgctgttgtc ctgtgttcac cggaagtaaa agagttcgaa gaagcagccc   2280
cagaagaagt tcaagagagt ggccacaagg tcgcccgctc tgcatttgtt gccgagggtc   2340
ctaacaatga acaggtaccg atggctgccg gcgagcaact gaagcccggt ggtcgcgttt   2400
tggcggtcgg gaatgctcat gaaggtgttc tggcctcaac tagttcgacc aacctgatag   2460
gcgggaactt cccccccttca gactccatga aagagagcat gctcaatagc tgggaagacg   2520
aaccactgga tttgtcccaa ccggcaccag ctgttacaat gacccttgtg agagagcaaa   2580
cacccgacaa cctgggtcct gatgccggtg ccttccccgt caccgttcga aaatttgtcc   2640
cgacagggcc tacactccgt catgttgagc actgcggcac ggagtcaggc gacagcagtt   2700
cgcccttgga tctgtcttat gcgcaaaccc tggaccagcc tttaaatcta tccttggccg   2760
cttggccagt gagggccacc gcgtctgacc ctggctgggt ccacggtagg cgtgagccta   2820
tctttgtgaa gcctcgagat gctttctctg acggcgattc agcccttcag ctcggggagc   2880
tgtctgaatc cggctccgtc atcgagtttg accggacaag aaatgctccg gcggtcgacg   2940
cccctgttga cttgacggct tcgaacaagg ccctctctgt ggttgatcct ttcgaatttg   3000
ccgaactcaa gcgcccgcgt ttttccgcac aagccttaat tgaccgaggc ggtccacttg   3060
ccgacgtcca tgcaaaaata aagaaccggg tatatgaaca gtgcctccag gcttgtgagc   3120
ctggcagtcg cgcaacccca gccaccaaga agtggctcga taaaatgtgg gatagggtgg   3180
```

```
acatgaagac ttggcgctgt acctcgcagt tccaagctgg tcgcattctt gcgtccctta   3240
aattcctccc tgacatgatt caggacacac cacctcctgt tcctaggaag aatcgggcta   3300
gtgataatgc cggcctgaag cgactggtgg cgcagtggga cagaaaattg agtgcaaccc   3360
ccccttcaaa accggttgga ccaacacttg accaaattgt cccttcgccc acgggtaccc   3420
agcaagaaga tgtcacttcc tccgatgggc catctcatgc gccggatcct cctagtcgaa   3480
tgagcacgag tgggagttgg aagggccttg tgctctctgg tacccgtctc gcggggtcca   3540
ttagtcagca tttcatgaca tgggtttttg aggttttctc ccatctccca gcttttgcac   3600
tcacactttt ctcgccgagg ggctctatgg cttcaggtga ttggatgttt gcaggtgttg   3660
ttttacttgc tctcctgctc tgtcgttctt acccagtatt cgggtgcctt cccttattgg   3720
gtgtcctttc tggctctgtg cggcgcgttc gtctgggggt tttggttct tggatggctt   3780
tcgctgtatt tttattctcg actccatcca acccagtcgg ttcttcttgt gaccacgatt   3840
cgccggagtg tcatgctgag cttttggctc ttgagcagcg ccaactttgg gaacctgtgc   3900
gcggccttgt ggtcggcccc tcgggcctct tatgtgtcat tcttggcaag ctactcggtg   3960
ggtcacgtta tctctggcat gttttcttac gtttatgcat gcttgcagat ttggcccttt   4020
ctcttgttta tgtggtgtcc caggggcgtt gtcacaagtg ttggggaaag tgtataagaa   4080
cagctccggc ggaggtggct ctcaatgtgt tccctttctc gcgcgctacc cgtagctctc   4140
ttgtgtcctt gtgcgatcgg ttccaagcgc caaaaggggt tgatcctgtg tacttggcaa   4200
cgggttggcg cgggtgttgg tgtggtgaga gtcccattca tcaaccgcac caaaaaccca   4260
tagcttatgc taatctggat gaaaagaaaa tatctgccca aacggtggtt gctgtcccac   4320
acgatcccag tcaggccatc aagtgcctga aagttttgca ggcgggagga gccatcgtgg   4380
accagcccac acctgaggtc gtccgtgtat ccgaaatccc cttctcagcc ccatttttcc   4440
caaaagttcc agtcaaccca gattgtaagg ttgtggtgga ttcggacact tttgtggctg   4500
cggttcgctg cggctactcg acagcacaac tggtcttagg ccagggcaac tttgccaagt   4560
taaatcagat tcccctcagg agctctatct ccaccaaagc gattggcggg gcctcttaca   4620
cccttgctgt ggctcaagtt tctgtgtgga ctcttgttca cttcatcctc ggtctttggt   4680
tcacgtcacc ccaagtgtgt ggccgaggaa cctctgactc atggtgttca aatccttttt   4740
cataccctac ctatggcccc ggggttgtgt gctcctctcg actttgtgtg tctgccgacg   4800
gggtcactct accattgttc tcagccgtgg ctcaactctc cggtagagag gtggggattt   4860
ttattttggt actcgtctcc ttgatggctt tggcccaccg catggccctt aaggcagaca   4920
tgttgatggt ctttctggct tttgtgctt acgcctggcc catgagctcc tggttgattt   4980
gcttctttcc tacactcttg aagtgggtta ccctccaccc tcttactatg ctttgggtgc   5040
actcattctt ggtgttttgt ctgccagcag ccggcatcct ctcactaggg ataactggcc   5100
ttctttgggc ggttggccgc tttactcagg ttgccggaat tattacacct tatgacatcc   5160
accagtacac ctctgggcca cgtggcgctg cagctgtggc cacagcccca gaaggcactt   5220
atatggccgc cgtccggaga gctgctttaa ctgggcgaac tttaatcttc accccgtctg   5280
cagttggatc ccttctcgaa ggagctttca ggactcataa accttgtctt aacaccgtaa   5340
atgttgtagg ctcttccctt ggttccggcg gggttttcac tattgacggc agaaaaattg   5400
ttgtcactgc tgcccatgtg ttgaacggcg acacagctag agtcaccggc gactcctaca   5460
accgcatgca tactttcaag accaatggtg attatgcctg gtcccatgct gatgactggc   5520
```

-continued

```
ggggcgttgc ccctgcggtc aaggttgcga aggggtaccg cggtcgtgcc tactggcaaa   5580

catcaactgg cgtcgaaccc ggtgttattg ggaagggtt cgccttctgt ttcaccacct   5640

gtggcgattc ggggtcaccc gtcatctcag aatccggtga tctcattgga atccataccg   5700

gttcaaataa acttggttct ggtcttgtga caacccctga aggggagaca tgtaccatca   5760

aagaaaccaa gctctctgac ctctccagac atttcgcagg cccaagcgtt cctcttgggg   5820

atattaaatt gagtccagcc atcatccctg atataacatc cattccgagt gacttggcat   5880

cgctcctatc ctccgtccct gtagtggaag gcggcctctc gaccgttcaa cttttgtgtg   5940

tctttttcct actttggcgc atgatgggcc atgcctggac tcccattgtt gccgtgggtt   6000

tctttttact gaatgaaatt cttccagcag ttttggtccg agccgtgttt tcttttgcac   6060

tttttgtgct tgcatgggcc accccctggt ctgcacaggt gttgatgatt agactcctca   6120

cggcatctct caaccgcaat aagctttctc tggcgttcta cgcactcggg ggggtcgtcg   6180

gtttggccgc tgaaatcggg acttttgctg gcaaattgcc tgaattgtct caaacccttt   6240

cgacatactg cttcttacct agggtccttg ctatgaccag ttgtgttccc accatcatca   6300

ttggtggact ccatgccctc ggtgtaattc tgtggttgtt caaataccgg tgcctccaca   6360

acatgctcgt tggtgatggg agtttttcaa gcgccttctt cctacggtat tttgcagagg   6420

gtaatctcag aaaaggtgtt tcgcagtcct gtggcatgaa taatgagtcc ctgacggctg   6480

ctttggcttg caagttgtca cggctgacc ttgatttttt gtccagctta acgaacttca   6540

agtgctttgt atctgcttcg aatatgaaaa atgctgccgg ccagtacatt gaagcggcgt   6600

atgccaaggc cctgcgccaa gagttggcgt ctctagttca gattgacaaa atgaaaggag   6660

ttttgtccaa actcgaggcc tttgctgaaa cagctactcc gtcccttgac ataggtgacg   6720

tgattgttct gcttgggcaa catccacacg gatctatcct tgatattaat gtggggactg   6780

agaggaaaac tgtgtccgtg caagagaccc ggagcctagg cggttccaaa ttcagtgttt   6840

gtactgtcgt gtctaacaca cccgtggacg ccttaaccgg catcccactc cagacaccaa   6900

cccctctttt tgagaatggt ccgcgtcatc gcagcgaaga agacgatctt aaagtcgaga   6960

ggatgaagaa acactgtgtg cccctcggct tccacaacat caatggcaaa gtttactgca   7020

agatttggga caagtccacc ggtgacacct tttacacgga tgattcccgg tatacccacg   7080

accatgctct tcaggacagg tcagccgact acagagacag ggactatgag ggtgtgcaaa   7140

ccgcccccca acagggattt gatccaaagt ctgaaacccc tgtcggcact gttgtgatcg   7200

gcggtattac gtataacagg tatctgacta agggtaagga ggttctggtt cccaagcccg   7260

acaattgcct tgaagctgcc aagctgtctc ttgagcaagc tctcgctggg atgggccaaa   7320

cttgcgacct tacagctgcc gaggtggaaa agttaaagcg catcatcagt caactccaag   7380

gtttgaccac tgaacaggct ttaaactgct agccgctagc ggcttgaccc gctgtggccg   7440

cggcggctta gttgttactg aaacggcggt aaaaattgta agataccaca gcagaacttt   7500

caccttgggc cctttggacc taaaagtcgc ttctgaggtg gaggtgaaga gatcaactga   7560

gcagggccac gctgttgtgg caaacctatg ttctggtgtt gtattgatga gacctcaccc   7620

accgtccctt gttgacgttc ttctgaaacc cggacttgac acaacacccg gcattcaacc   7680

ggggcatggg gccgggaata tgggcgtgga cggttccatt tgggattttg aaaccgcacc   7740

cacaaaggca gagctcgagt tgtccaggca aataatccaa gcatgtgaag tcaggcgcgg   7800

ggatgccccg aacctccaac tcccttacaa gctctgtcca gttagggggg atcctgagcg   7860

gcataaaggc cgccttatca ataccaggtt tggagatttg ccttacaaga ctcctcaaga   7920
```

```
caccaagtcc gcaatccacg cggcttgttg cctgcacccc aacggggctc ccgtgtctga   7980
tggtaaatcc acattaggca ccactcttca acacggtttc gagctttatg tccctactgt   8040
gccctatagt gtcatggagt accttgattc acgccctgac accccttta tgtgtaccaa    8100
acatggtacc cccgaggctg ctgcagagga ccttcgaaaa tatgacttat ccacccaagg   8160
gtttgtcctg cctggggtcc tacgtctagt acgcagattc atctttggcc atattggtaa   8220
ggcaccgcca ctgttcctcc catcaactta tcccgccaag aactctatgg cagggatcaa   8280
tggccagagg ttcccaacaa aagacgttca gagcatacct gaaattgatg aaatgtgtgc   8340
ccgcgctgtc aaagagaatt ggcaaactgt gacgccttgc accctcaaaa aacagtattg   8400
ttccaagcct aaaaccagga ccatccttgg taccaacaac ttcattgcct tggctcacag   8460
gtcggcactc agcggtgtca ctcaggcgtt catgaaaaaa gcctggaagt ccccgatcgc   8520
cttggggaaa aacaaattta aggagttgca ctgcactgtc gccggtaggt gcctcgaggc   8580
cgacttggcc tcttgtgatc gcagcacccc ggccatcgtg aggtggtttg ttgccaacct   8640
cctgtacgaa cttgcgggtt gtgaagagta cttgccaagc tatgtgctca attgttgcca   8700
tgacctggtg gcaacgcaaa atggcgcctt cacaaaacgt ggtggcctgt catctggaga   8760
ccccgttacc agtgtgtcca acacagtgta ttcactggtg atttatgctc agcacatggt   8820
gctgtcggct ttgaagatgg gtcatgaaat cggcctcaag ttcctcgagg aacagcttaa   8880
gttcgaggac cttctcgaaa tccagcctat gttggtatat tctgatgacc ttgtattgta   8940
tgctgaaaga cccaccttcc ccaattacca ttggtgggtt gagcaccttg acctgatgct   9000
gggttttaag acagacccaa aaaagactgt cataactgac aaacccagct ttcttggctg   9060
tagaatcgaa gcggggcgac aactggttcc cagtcgcgac cgcattctgg ctgctcttgc   9120
atatcacatg aaggcgcaga acgcctcaga gtattatgcg tctgctgccg cgattctgat   9180
ggactcgtgt gcttgcattg accacgatcc tgagtggtat gaggacctca tctgcggcat   9240
tgctcgatgc gcccgccagg atggctacag tttcccaggc ccgccgttct tcatgtccat   9300
gtgggagaag ctgaaaagtc acaatgaagg caagaaattc cgccactgtg gcatttgtga   9360
cgccaaggcc gatcatgcgt ccgcctgtgg gcttgattta tgtctgttcc actcgcactt   9420
tcatcaacac tgccctgtta ctctgagctg cggccatcat gccggttcaa aagaatgccc   9480
acagtgtcag tcacctgttg gagctggtaa atcccccctt gatgcagtgc tgaaacaaat   9540
cccgtacaaa cccccctcgtc ctgtcatcat gaaggtggac aataaaacaa cgacccttga  9600
cccgggaagg tatcagtccc gtcgaggtct tgttgctgtc aagaggggta ttgcaggcaa   9660
tgaggttgat ctcgctgatg gagactatca ggtggtgccc cttttgccaa cctgcaaaga   9720
cataaacatg gtgaaggtgg ctgtcaatgt gctactcagc aagttcatag tggggccgcc   9780
aggttccggc aagacgacct ggctactgag tcaagttcag gatgatgatg tcatctatac   9840
acctacccat cagaccatgt tcgacatagt caatgccctc aaagtctgta ggtattccat   9900
cccagtggct tcagggctcc ctttcccacc gcccgccaga tctggaccgt gggttaggct   9960
cgttgctagc gggcacatcc ctggccgaat atcatacctt gacgaggccg gatattgcaa  10020
tcatctggat attctcagac tgctttctaa gacacctctt gtgtgtttgg gtgaccttca  10080
gcaacttcac cctgtcggct ttgactctta ctgttatgtt tttgatcaca tgcctcataa  10140
gcagctgacc actatttata gatttggccc caatatctgt tctgccattc aaccttgtta  10200
cagggaaaaa ctcgaatcta aggccaggaa cactagggtg gtttttactg cccggcccgt  10260
```

```
ggcttttggt caggtgttga cgccatatca taaagaccgc accggctcag ctataaccat  10320
agattcatcc cagggagcca cctttgatgt tgtgacgctg catttgccgt cgccagattc  10380
cctgaacaaa tcccgggctc ttgtagctat cactcgggca aggcatgggt tgttcatcta  10440
tgaccctcat aaccaactcc ggaagttttt caacttaaca cctgagcgca ctgattgcaa  10500
cctcgtgttc aaccgcgggg acgagttggt agttttgaat gcagataatg cagtcacgac  10560
tgtggctaag gttctggagg cgggcccgtc tcggtttcga gtatcagatc caaggtgcaa  10620
gtctctttta gccgcttgct cggccagtct ggaaggaggc tgcatgccac tgccgcaagt  10680
ggcacataat ctggggtttt acttctctcc agatagtcca gcatttgcac ctctgccaaa  10740
agagctggca ccacattggc cggttgttac tagtcagaac aaccaggcat ggcccgaccg  10800
acttgtcgct agtatgcggc cagttgatgc ccgctacagc aagcctatgg tcggtgcagg  10860
gtatgtggtt gggccatcca ctttccttgg cactcctggt gtggtgtcat actatctcac  10920
gctgtacatc aggggtgagc cccaggcctt gccggagaca ctcgtctcaa cgggacgtat  10980
agctactgat tgtcgagagt atctcgacgc agctgaggaa gaagcagcta aagaactccc  11040
tcacgcattc attggcgatg tcaaaggtac tacagtgggg gggtgtcacc acattacgtc  11100
aaaatacctt cccaggtcct tgcccaagga ctccgttgcc gtggtcggag tgagttcgcc  11160
cggcaaggct gccaaagccg tgtgtactct caccgatgtg tatcttcccg agctccggcc  11220
atatttgcaa ccggaaacag catcgaaatg ctggaaactt aaactagact tcagggatgt  11280
cagactgatg gtctggaaag gagccaccgc atatttccaa ctggaggggc tcacatggtc  11340
agcgctgccc gactatgcca ggttcattca gctaccaaaa gatgccgttg tgtacattga  11400
tccgtgcata ggaccggcaa cagccaaccg taaggttgtg agaactacag attggcgagc  11460
tgacctggca gtgacaccgt acgactacgg tgctcagagc attttgacta cagcctggtt  11520
cgaggacctt gggccgcagt ggaagatttt agggttgcaa cccttcaagc gggcatttgg  11580
ctttgaaaac actgaggatt gggcgatcct tgcacgtcgc atgaacgacg gcaaggacta  11640
cactgactat aactggaatt gtgttcgaca acgcccacat gccatctacg gacgtgcccg  11700
tgaccatacg tatcactttg cccctggcac tgaactgcaa gtagagctag gtaaacctcg  11760
gctaccgcct gagcaagtac cgtgaatcta gagtgatgca atggggtcac tgtggagtaa  11820
aatcagtcaa ctgttcgtgg atgccttcac tgagttcctt gttagtgtgg ttgatattgt  11880
catcttcctt gccatactgt ttgggttcac cgttgcaggg tggttactgg tctttttttt  11940
cagagtggtt tgctccgcgc ttctccgttc gcgctctgcc attcactctt ccgaactatc  12000
gaaggtccta tgagggcttg ctacctaatt gcagaccgga tgttccacaa ttcgcattca  12060
agcacccatt gggtatgttt tggcacatgc gagtttccca cttaattgac gaaatggtct  12120
ctcgccgcat ttatcagacc atggaacatt caggtcaagc ggcctggaag caggtggtta  12180
gtgaagctac tctcacaaga ctgtcaaagc tcgacatagt tctccacttc caacacctgg  12240
ccgcaataga ggcggattct tgccgcttcc tcagctcacg acttgtgatg ctgaaaaatc  12300
ttgctgttgg caatatgagc ctacagtaca acaccacgtt ggaccgcgtt gagctcatct  12360
tcccaacacc aggtacgagg cccaaattga ccgattttag acaatggctc gtcagtgtgc  12420
acgcttctat tttttcctct gtggcctcat cagttacctt gttcatagtg ctttggcttc  12480
gaattccagc tctacgctat gtttttggtt tccattggcc cacggcaaca catcattcga  12540
gctaaccatc aattactcta tatgtaagcc ctgtctcacc agtcaagcgg ctcgacaaag  12600
gctcgaaccc ggtcgcaaca tgtggtgcaa aatagggcac accacgtgtg aggagcgtga  12660
```

```
ccatgatgag ttgtcaatga ccattccgtc cgggtacgat aacctcaaac ttgagggtta  12720
ttacgcttgg ctggcttttt tgtccttttc ttacgcagcc caatttcatc cagagttgtt  12780
cggaataggg aatgtgtcac gcgtcttcgt ggataaacgg caccagttca tctgtgccga  12840
gcacgacgga caaaattcaa ccgtatccac cgaacataat atttccgcat tgtatgcggc  12900
gtactaccac caccaggtag acgggggcaa ttggttccac ctggaatggc tgcggccttt  12960
cttttcctcc tggctagtac tcaatatttc atggtttctg aggcgttcgc ctgcaagccc  13020
tgtttctcga cgcatttatc agatattgag accaacacga ccgcggctgc cggtttcatg  13080
gtccttcagg acatcaactg tttccacagt ggctcagagg cacaaacgac tggtcccatc  13140
agaaagtcgt cccaatgccg tgaagccgtc ggcactcccc agtacatcaa gataacggcc  13200
aatctgaccg acgaatcata cttgtacaac gcggacttgc tgatgctttc tgcgtgcctt  13260
ttctacgcct cagagatgag cgagaaaggc tttaaagtca tttttgggaa tgtctctggc  13320
gttgtctccg cttgtgtcaa ttttacagat tatgtggccc atctgaccca acatacccag  13380
cagcatcatt tggtaaccaa tcacattcgg ttgctacatt tcctgacacc atcagcgatg  13440
aggtgggcta caaccattgc ttgtttgttc gccattctct tggcgatatg agatgttctc  13500
acaaatcggg gtgtttcttg actccgcact cttgcttttg gtggtttttt ttgctgtgta  13560
ccggcttgtc ctggtccttt gccgatggca acggcgacag ctcgacatac caatatatat  13620
ataacttgac gatatgcgag ctgaatggga ccgaatggct gtctgaccat tttaattggg  13680
cagtcgagac ttttgtgctc tacccagtgg cgactcatat cctctcactg ggtttcctca  13740
cgacaagtca tttccttgat gcgttcggtc ttggagctgt gtcaattaca gggttttgtg  13800
gcgggcggta cgtgctcagc agcgtgtacg gcgcttgtgc actagcagcg ctcgtatgtt  13860
ttgttatccg tgctgccaaa aattgtatgg cttgccgcta tgctcgtacc cggtttacca  13920
acttcattgt ggatgaccgg gggagaatcc atcggtggag gtctccaata gtggtggaaa  13980
aattaggtaa agctgacgtc ggcggcgacc ttgtcaccat caaacatgtc atcctcgaag  14040
gagtcaaagc tcaacccttg acgaggactt cggccgagca atgggaggcc tagataattt  14100
ctgcaacgat cccaccgccg cacaaaagct tgtgctagcc tttagcatca cgtatacacc  14160
catcatgata tacgccctta aggtgtcacg cggccgactc ttggggttgt tgcacatctt  14220
gatatttctg aactgttctt tcacgttcgg atacatgaca tatatgcatt ttgaatccac  14280
caaccgtgtc gcgcttacca tggggggcgt tgtcgccctt ctgtggggcg tttatagttt  14340
catagagtca tggaagttta tcacttccag atgcagattg tgttgcctag gccggcgata  14400
cattctggcc cctgcccacc acgtagaaag tgctgcaggc ctccatccga tcccagcgtc  14460
tggtaaccaa gcatacgctg tgagaaagcc cggactaaca tcagtgaacg gcactctggt  14520
accaggactt cgaggcctcg tgctgggcgg caaacgagct gttaaacgag gagtggttaa  14580
cctcgtcaag tatggccggt aaaaaccaga gccagaagaa aaagaaaaat ccagctccaa  14640
tggggaatgg ccagtcagtc aatcaactgt gccagctgct gggcacaatg ataaagtccc  14700
agcgccagcg acccagggga ggacaggcta aaaagaaaaa gcctgagaag ccacatttcc  14760
ccctggctgc tgaagatgac gtccggcacc atctcaccca gaccgagcgc tccctttgct  14820
tgcaatcgat ccagacggct tttaatcaag gcgcaggaac tgcgtcgctt tcatccagcg  14880
ggaagatcgg ttttcaggtt gagtttatgc taccggttgc tcatacagtg cgcctgattc  14940
gcgtgacttc tacatccgcc ggtcaggatg caaattaatt tgatagtcag gtgaatggcc  15000
```

gcgattggcg tgtggcctct gagtcaccta ttcaattagg gcgatcacat gggggtcaga 15060
cttaattagg caggaaccat gtgaccgaaa tt 15092

<210> SEQ ID NO 5
<211> LENGTH: 15092
<212> TYPE: DNA
<213> ORGANISM: Artificial Sequence
<220> FEATURE:
<223> OTHER INFORMATION: PRRS virus isolate 96V198 - passage 49

<400> SEQUENCE: 5
atgatgtgta gggtattccc cctacataca cgacacttct agtgtttgtg tgccttggag 60
gcgtgggtat agccccgccc cacctcttgg cccctgttct agcccaacag gtatccttct 120
ctctcggggc gagcgcgccg cctgctgctc ccttgcagca ggaaggacct cccgagtatt 180
tccggagagc acctgcttta cgggatctcc accctttaac catgtctggg acgttctccc 240
ggtgcatgtg caccccggct gcccgggtat tttggagcgc cggccaagtc tattgcacac 300
ggtgtctcag tgcacggtct cttctctctc cggagcttca ggacactgac ctcgctgcaa 360
ttggcttgtt ttacaagcct aaagacaagc ttcactggaa agtccctatc ggcatccctc 420
aggtggagtg tactccgtcc gggtgctgtt ggctctcagc catcttcccc ttggcgcgca 480
tgacctccgg caatcacaac tttctccaac gacttgtgaa ggttgctgat gttttgtacc 540
gtgacggctg cttggcacct cgacaccttc gcgaactcca agtttacgag cgcggctgca 600
actggtaccc gatcacgggg cccgtgcccg ggatgggttt gtacgcgaac tccatgcacg 660
tgtccgacca accgttccct ggtgccgctt atgtgttaac gaactcacct ctgcctcagc 720
aggcttgtcg acagccgttt tgtccatttg aggaggttca ttccgacgta tacaggtgga 780
agaaattcgt gatttttgtg gattcctctt ctgacggccg atctcgcatg atgtggacac 840
caggatccga cgactcggct gccttagaag tattgccacc tgaactagaa tgtcgagtcg 900
aaatcctcgt tcggagtttt cctgcccacc accctgtcga catcaccaac tgggagctca 960
ctgagtcccc tgagcacggt ttttccttca gcacgtctca ttcttgtggt taccttgccc 1020
aagaccctga cgtgtttgat ggtaagtgtt ggctttcttg ctttttgggc ctgccgaccg 1080
aagtgtggcg tcatgaggag catctagcta acgccttcgg ttaccaaacc aagtggggcg 1140
tgcatggtaa gtacctccag cgcaggcttc aggtccgcgg catgcgtgct gtagttgatc 1200
ctgatggtcc catccacgtt gaagcgctgt cttgcccccca gtcttggatc aggcacctga 1260
ctctaaatga tgacgtcacc ccaggatttg ttcgcctaac atcccttcgc attgagccga 1320
acacagagcc tactactttc cggatctttc ggtttggagc gcataagtgg tatggcgctg 1380
ccggcaaacg ggctcgtgct aagcgtgccg ctaaaggtga gaagaattca gctcccaccc 1440
ccaaggtcgc cctgccggtc cccacctatg gaattaccac ctactctcca ccgacagacg 1500
ggtcttgtgg ttggcatgtc cttgccgcca taatgaaccg gatgataaat ggtgacttca 1560
cgtcccctct gactccgtac aacagaccag aggatgattg ggcttctgat tatgatcttg 1620
ctcaggcaat ccaatgtcta caactgcctg ctaccgtggt ccggagtcgc gcctgtccca 1680
acgccaagta cctcataaaa ctcaacggag tccactggga ggtagaggtg aggtcaggaa 1740
tggctcctcg ctctctttct cgtgaatgtg tggttggcgt ttgctctgaa ggttgtgttg 1800
caccgcctta tccagcagac gggctaccag aacgagcact cgaggccttg gcgtctgctt 1860
acaggttacc ctctgattgt gttagctctg gcattgctga ctttcttgct aacccacctc 1920
ctcaggaatt ctggaccctc gacaaaatgt tgacctcccc gtcaccagag cggtccggct 1980

```
tctctagttt gtataaatta ctattagagg ttgttccgca aaaatgcggt gccacggaag   2040
gggctttcgt ctatgctgtt gagagaatgt tgaaggattg tccgagctcc aaacaggcca   2100
tggcccttct ggcaaaaatt aaagttccat cctcaaaggc cccgtctgtg tcccttgacg   2160
agtgtttccc tacggatgtt tcagccgact tcgagccagc atctcaggaa aggccccaaa   2220
gttccggtgc tgctgttgtc ctgtgttcac cggaagtaaa agagttcgaa gaagcagccc   2280
cagaagaagt tcaagagagt ggccataagg tcgcccgctc tgcatttgtt gccgagggtc   2340
ctaacaatga acaggtaccg atggctgccg gcgagcaact gaagcccggt ggtcgcgttt   2400
tggcggtcgg gaatgctcat gaaggtgttc tggcctcaac tagttcgacc aacctgatag   2460
gcgggaactt ccccccttca gactccatga aagagagcat gctcaatagc tgggaagacg   2520
aaccactgga tttgtcccaa ccggcaccag ctgttacaat gacccttgtg agagagcaaa   2580
cacccgacaa cctgggtcct gatgccggtg ccttccccgt caccgttcga aaatttgtcc   2640
cgacagggcc tacactccgt catgttgagc actgcggcac ggagtcaggc gacagcagtt   2700
cgcccttgga tctgtcttat gcgcaaaccc tggaccagcc tttaaatcta tccttggccg   2760
cttggccagt gagggccacc gcgtctgacc ctggctgggt ccacggtagg cgtgagccta   2820
tctttgtgaa gcctcgagat gctttctctg acggcgattc agcccttcag ctcggggagc   2880
tgtctgaatc cggctccgtc atcgagtttg accggacaag aaatgctccg gcggtcgacg   2940
cccctgttga cttgacggct tcgaacaagg ccctctctgt ggttgatcct ttcgaatttg   3000
ccgaactcaa gcgcccgcgt ttttccgcac aagccttaat tgaccgaggc ggtccacttg   3060
ccgacgtcca tgcaaaaata aagaaccggg tatatgaaca gtgcctccag gcttgtgagc   3120
ctggcagtcg cgcaacccca gccaccaaga agtggctcga taaaatgtgg gatagggtgg   3180
acatgaagac ttggcgctgt acctcgcagt tccaagctgg tcgcattctt gcgtccctta   3240
aattcctccc tgacatgatt caggacacac cacctcctgt tcctaggaag aatcgggcta   3300
gtgataatgc cggcctgaag cgactggtgg cgcagtggga cagaaaattg agtgcaaccc   3360
ccccttcaaa accggttgga ccaacacttg accaaattgt cccttcgccc acgggtaccc   3420
agcaagaaga tgtcacttcc tccgatgggc catctcatgc gccggatcct cctagtcgaa   3480
tgagcacgag tgggagttgg aagggccttg tgctctctgg tacccgtctc gcggggtcca   3540
ttagtcagca tttcatgaca tgggtttttg aggttttctc ccatctccca gcttttgcac   3600
tcacactttt ctcgccgagg ggctctatgg cttcaggtga ttggatgttt gcaggtgttg   3660
ttttacttgc tctcctgctc tgtcgttctt acccagtatt cgggtgcctt cccttattgg   3720
gtgtcctttc tggctctgtg cggcgcgttc gtctgggggt ttttggttct tggatggctt   3780
tcgctgtatt tttattctcg actccatcca acccagtcgg ttcttcttgt gaccacgatt   3840
cgccggagtg tcatgctgag cttttggctc ttgagcagcg ccaactttgg gaacctgtgc   3900
gcggccttgt ggtcggcccc tcgggcctct tatgtgtcat tcttggcaag ctactcggtg   3960
ggtcacgtta tctctggcat gttttcttac gtttatgcat gcttgcagat ttggcccttt   4020
ctcttgttta tgtggtgtcc caggggcgtt gtcacaagtg ttggggaaag tgtataagaa   4080
cagctccggc ggaggtggct ctcaatgtgt tccctttctc gcgcgctacc cgtagctctc   4140
ttgtgtcctt gtgcgatcgg ttccaagcgc caaaaggggt tgatcctgtg tacttggcaa   4200
cgggttggcg cgggtgttgg tgtggtgaga gtcccattca tcaaccgcac caaaaaccca   4260
tagcttatgc taatctggat gaaaagaaaa tatctgccca aacggtggtt gctgtcccac   4320
```

-continued

```
acgatcccag tcaggccatc aagtgcctga aagttttgca ggcgggagga gccatcgtgg   4380
accagcccac acctgaggtc gtccgtgtat ccgaaatccc cttctcagcc ccatttttcc   4440
caaaagttcc agtcaaccca gattgtaagg ttgtggtgga ttcggacact tttgtggctg   4500
cggttcgctg cggctactcg acagcacaac tggtcttagg ccagggcaac tttgccaagt   4560
taaatcagat tcccctcagg agctctatct ccaccaaagc gattggcggg gcctcttaca   4620
cccttgctgt ggctcaagtt tctgtgtgga ctcttgttca cttcatcctc ggtctttggt   4680
tcacgtcacc ccaagtgtgt ggccgaggaa cctctgactc atggtgttca aatccttttt   4740
catacccctac ctatggcccc ggggttgtgt gctcctctcg actttgtgtg tctgccgacg   4800
gggtcactct accattgttc tcagccgtgg ctcaactctc cggtagagag gtggggattt   4860
ttattttggt actcgtctcc ttgatggctt tggcccaccg catggccctt aaggcagaca   4920
tgttgatggt ctttctggct tttttgtgctt acgcctggcc catgagctcc tggttgattt   4980
gcttctttcc tacactcttg aagtgggtta ccctccaccc tcttactatg ctttgggtgc   5040
actcattctt ggtgttttgt ctgccagcag ccggcatcct ctcactaggg ataactggcc   5100
ttctttgggc ggttggccgc tttactcagg ttgccggaat tattacacct tatgacatcc   5160
accagtacac ctctgggcca cgtggcgctg cagctgtggc cacagcccca gaaggcactt   5220
atatggccgc cgtccggaga gctgctttaa ctgggcgaac tttaatcttc accccgtctg   5280
cagttggatc ccttctcgaa ggagctttca ggactcataa accttgtctt aacaccgtaa   5340
atgttgtagg ctcttccctt ggttccggcg gggttttcac tattgacggc agaaaaattg   5400
ttgtcactgc tgcccatgtg ttgaacggcg acacagctag agtcaccggc gactcctaca   5460
accgcatgca tactttcaag accaatggtg attatgcctg gtcccatgct gatgactggc   5520
ggggcgttgc ccctgcggtc aaggttgcga aggggtaccg cggtcgtgcc tactggcaaa   5580
catcaactgg cgtcgaaccc ggtgttattg gggaagggtt cgccttctgt ttcaccacct   5640
gtggcgattc ggggtcaccc gtcatctcag aatccggtga tctcattgga atccataccg   5700
gttcaaataa acttggttct ggtcttgtga caacccctga aggggagaca tgtaccatca   5760
aagaaaccaa gctctctgac ctctccagac atttcgcagg cccaagcgtt cctcttgggg   5820
atattaaatt gagtccagcc atcatccctg atataacatc cattccgagt gacttggcat   5880
cgctcctatc ctccgtccct gtagtggaag gcggcctctc gaccgttcaa cttttgtgtg   5940
tctttttcct actttggcgc atgatgggcc atgcctggac tcccattgtt gccgtgggtt   6000
tctttttact gaatgaaatt cttccagcag ttttggtccg agccgtgttt tcttttgcac   6060
tttttgtgct tgcatgggcc accccctggt ctgcacaggt gttgatgatt agactcctca   6120
cggcatctct caaccgcaat aagctttctc tggcgttcta cgcactcggg ggggtcgtcg   6180
gtttggccgc tgaaatcggg acttttgctg gcaaattgcc tgaattgtct caaacccttt   6240
cgacatactg cttcttacct agggtccttg ctatgaccag ttgtgttccc accatcatca   6300
ttggtggact ccatgccctc ggtgtaattc tgtggttgtt caaataccgg tgcctccaca   6360
acatgctcgt tggtgatggg agtttttcaa gcgccttctt cctacggtat tttgcagagg   6420
gtaatctcag aaaaggtgtt tcgcagtcct gtggcatgaa taacgagtcc ctgacggctg   6480
ctttggcttg caagttgtca cgggctgacc ttgatttttt gtccagctta acgaacttca   6540
agtgctttgt atctgcttcg aatatgaaaa atgctgccgg ccagtacatt gaagcggcgt   6600
atgccaaggc cctgcgccaa gagttggcgt ctctagttca gattgacaaa atgaaaggag   6660
ttttgtccaa actcgaggcc tttgctgaaa cagctactcc gtcccttgac ataggtgacg   6720
```

```
tgattgttct gcttgggcaa catccacacg gatctatcct tgatattaat gtggggactg   6780
agaggaaaac tgtgtccgtg caagagaccc ggagcctagg cggttccaaa ttcagtgttt   6840
gtactgtcgt gtctaacaca cccgtggacg ccttaaccgg catcccactc cagacaccaa   6900
cccctctttt tgagaatggt ccgcgtcatc gcagcgaaga agacgatctt aaagtcgaga   6960
ggatgaagaa acactgtgtg cccctcggct tccacaacat caatggcaaa gtttactgca   7020
agatttggga caagtccacc ggtgacacct tttacacgga tgattcccgg tatacccacg   7080
accatgctct tcaggacagg tcagccgact acagagacag ggactatgag ggtgtgcaaa   7140
ccgcccccca acagggattt gatccaaagt ctgaaacccc tgtcggcact gttgtgatcg   7200
gcggtattac gtataacagg tatctgacta agggtaagga ggttctggtt cccaagcccg   7260
acaattgcct tgaagctgcc aagctgtctc ttgagcaagc tctcgctggg atgggccaaa   7320
cttgcgacct tacagctgcc gaggtggaaa agttaaagcg catcatcagt caactccaag   7380
gtttgaccac tgaacaggct ttaaactgct agccgctagc ggcttgaccc gctgtggccg   7440
cggcggctta gttgttactg aaacggcggt aaaaattgta agataccaca gcagaacttt   7500
caccttgggc cctttggacc taaaagtcgc ttctgaggtg gaggtgaaga gatcaactga   7560
gcagggccac gctgttgtgg caaacctatg ttctggtgtt gtattgatga gacctcaccc   7620
accgtccctt gttgacgttc ttctgaaacc cggacttgac acaacacccg gcattcaacc   7680
ggggcatggg gccgggaata tgggcgtgga cggttccatt tgggattttg aaaccgcacc   7740
cacaaaggca gagctcgagt tgtccaggca aataatccaa gcatgtgaag tcaggcgcgg   7800
ggatgccccg aacctccaac tcccttacaa gctctgtcca gttagggggg atcctgagcg   7860
gcataaaggc cgccttatca ataccaggtt tggagatttg ccttacaaga ctcctcaaga   7920
caccaagtcc gcaatccacg cggcttgttg cctgcacccc aacggggctc ccgtgtctga   7980
tggtaaatcc acattaggca ccactcttca acacggtttc gagctttatg tccctactgt   8040
gccctatagt gtcatggagt accttgattc acgccctgac accccccttta tgtgtaccaa   8100
acatggtacc cccgaggctg ctgcagagga ccttcgaaaa tatgacttat ccacccaagg   8160
gtttgtcctg cctggggtcc tacgtctagt acgcagattc atctttggcc atattggtaa   8220
ggcaccgcca ctgttcctcc catcaactta tcccgccaag aactctatgg cagggatcaa   8280
tggccagagg ttcccaacaa aagacgttca gagcatacct gaaattgatg aaatgtgtgc   8340
ccgcgctgtc aaagagaatt ggcaaactgt gacgccttgc accctcaaaa aacagtattg   8400
ttccaagcct aaaaccagga ccatccttgg taccaacaac ttcattgcct tggctcacag   8460
gtcggcactc agcggtgtca ctcaggcgtt catgaaaaaa gcctggaagt ccccgatcgc   8520
cttggggaaa aacaaattta aggagttgca ctgcactgtc gccggtaggt gcctcgaggc   8580
cgacttggcc tcttgtgatc gcagcacccc ggccatcgtg aggtggtttg ttgccaacct   8640
cctgtacgaa cttgcgggtt gtgaagagta cttgccaagc tatgtgctca attgttgcca   8700
tgacctggtg gcaacgcaaa atggcgcctt cacaaaacgt ggtggcctgt catctggaga   8760
ccccgttacc agtgtgtcca acacagtgta ttcactggtg atttatgctc agcacatggt   8820
gctgtcggct ttgaagatgg gtcatgaaat cggcctcaag ttcctcgagg aacagcttaa   8880
gttcgaggac cttctcgaaa tccagcctat gttggtatat tctgatgacc ttgtattgta   8940
tgctgaaaga cccaccttcc ccaattacca ttggtgggtt gagcaccttg acctgatgct   9000
gggttttaag acagacccaa aaaagactgt cataactgac aaacccagct ttcttggctg   9060
```

```
tagaatcgaa gcggggcgac aactggttcc cagtcgcgac cgcattctgg ctgctcttgc   9120
atatcacatg aaggcgcaga acgcctcaga gtattatgcg tctgctgccg cgattctgat   9180
ggactcgtgt gcttgcattg accacgatcc tgagtggtat gaggacctca tctgcggcat   9240
tgctcgatgc gcccgccagg atggctacag tttcccaggc ccgccgttct tcatgtccat   9300
gtgggagaag ctgaaaagtc acaatgaagg caagaaattc cgccactgtg gcatttgtga   9360
cgccaaggcc gatcatgcgt ccgcctgtgg gcttgattta tgtctgttcc actcgcactt   9420
tcatcaacac tgccctgtta ctctgagctg cggccatcat gccggttcaa aagaatgccc   9480
acagtgtcag tcacctgttg gagctggtaa atcccccctt gatgcagtgc tgaaacaaat   9540
cccgtacaaa ccccctcgtc ctgtcatcat gaaggtggac aataaaacaa cgacccttga   9600
cccgggaagg tatcagtccc gtcgaggtct tgttgctgtc aagaggggta ttgcaggcaa   9660
tgaggttgat ctcgctgatg gagactatca ggtggtgccc cttttgccaa cctgcaaaga   9720
cataaacatg gtgaaggtgg ctgtcaatgt gctactcagc aagttcatag tggggccgcc   9780
aggttccggc aagacgacct ggctactgag tcaagttcag gatgatgatg tcatctatac   9840
acctacccat cagaccatgt tcgacatagt caatgccctc aaagtctgta ggtattccat   9900
cccagtggct tcagggctcc ctttcccacc gcccgccaga tctggaccgt gggttaggct   9960
cgttgctagc gggcacatcc ctggccgaat atcatacctt gacgaggccg gatattgcaa  10020
tcatctggat attctcagac tgctttctaa gacacctctt gtgtgtttgg gtgaccttca  10080
gcaacttcac cctgtcggct ttgactctta ctgttatgtt tttgatcaca tgcctcataa  10140
gcagctgacc actatttata gatttggccc caatatctgt tctgccattc aaccttgtta  10200
cagggaaaaa ctcgaatcta aggccaggaa cactagggtg gtttttactg cccggcccgt  10260
ggcttttggt caggtgttga cgccatatca taaagaccgc accggctcag ctataaccat  10320
agattcatcc cagggagcca cctttgatgt tgtgacgctg catttgccgt cgccagattc  10380
cctgaacaaa tcccgggctc ttgtagctat cactcgggca aggcatgggt tgttcatcta  10440
tgaccctcat aaccaactcc ggaagttttt caacttaaca cctgagcgca ctgattgcaa  10500
cctcgtgttc aaccgcgggg acgagttggt agttttgaat gcagataatg cagtcacgac  10560
tgtggctaag gttctggagg cgggcccgtc tcggtttcga gtatcagatc caaggtgcaa  10620
gtctctttta gccgcttgct cggccagtct ggaaggaggc tgcatgccac tgccgcaagt  10680
ggcacataat ctggggtttt acttctctcc agatagtcca gcatttgcac ctctgccaaa  10740
agagctggca ccacattggc cggttgttac tagtcagaac aaccaggcat ggcccgaccg  10800
acttgtcgct agtatgcggc cagttgatgc ccgctacagc aagcctatgg tcggtgcagg  10860
gtatgtggtt gggccatcca ctttccttgg cactcctggt gtggtgtcat actatctcac  10920
gctgtacatc aggggtgagc cccaggcctt gccggagaca ctcgtctcaa cgggacgtat  10980
agctactgat tgtcgagagt atctcgacgc agctgaggaa gaagcagcta aagaactccc  11040
tcacgcattc attggcgatg tcaaaggtac tacagtgggg gggtgtcacc acattacgtc  11100
aaaatacctt cccaggtcct tgcccaagga ctccgttgcc gtggtcggag tgagttcgcc  11160
cggcaaggct gccaaagccg tgtgtactct caccgatgtg tatcttcccg agctccggcc  11220
atatttgcaa ccggaaacag catcgaaatg ctggaaactt aaactagact tcaggatgt   11280
cagactgatg gtctggaaag gagccaccgc atatttccaa ctggaggggc tcacatggtc  11340
agcgctgccc gactatgcca ggttcattca gctaccaaaa gatgccgttg tgtacattga  11400
tccgtgcata ggaccggcaa cagccaaccg taaggttgtg agaactacag attggcgagc  11460
```

```
tgacctggca gtgacaccgt acgactacgg tgctcagagc attttgacta cagcctggtt  11520
cgaggacctt gggccgcagt ggaagatttt agggttgcaa cccttcaagc gggcatttgg  11580
ctttgaaaac actgaggatt gggcgatcct tgcacgtcgc atgaacgacg gcaaggacta  11640
cactgactat aactggaatt gtgttcgaca acgcccacat gccatctacg gacgtgcccg  11700
tgaccatacg tatcactttg cccctggcac tgaactgcaa gtagagctag gtaaacctcg  11760
gctaccgcct gagcaagtac cgtgaatcta gagtgatgca atggggtcac tgtggagtaa  11820
aatcagtcaa ctgttcgtgg atgccttcac tgagttcctt gttagtgtgg ttgatattgt  11880
catcttcctt gccatactgt ttgggttcac cgttgcaggg tggttactgg tcttttttct  11940
cagagtggtt tgctccgcgc ttctccgttc gcgctctgcc attcactctt ccgaactatc  12000
gaaggtccta tgagggcttg ctacctaatt gcagaccgga tgttccacaa ttcgcattca  12060
agcacccatt gggtatgttt tggcacatgc gagtttccca cttaattgac gaaatggtct  12120
ctcgccgcat ttatcagacc atggaacatt caggtcaagc ggcctggaag caggtggtta  12180
gtgaagctac tctcacaaga ctgtcaaagc tcgacatagt tctccacttc caacacctgg  12240
ccgcaataga ggcggattct tgccgcttcc tcagctcacg acttgtgatg ctgaaaaatc  12300
ttgctgttgg caatatgagc ctacagtaca acaccacgtt ggaccgcgtt gagctcatct  12360
tcccaacacc aggtacgagg cccaaattga ccgattttag acaatggctc gtcagtgtgc  12420
acgcttctat tttttcctct gtggcctcat cagttacctt gttcatagtg ctttggcttc  12480
gaattccagc tctacgctat gtttttggtt tccattggcc cacggcaaca catcattcga  12540
gctaaccatc aattactcta tatgtaagcc ctgtctcacc agtcaagcgg ctcgacaaag  12600
gctcgaaccc ggtcgcaaca tgtggtgcaa aatagggcac accacgtgtg aggagcgtga  12660
ccatgatgag ttgtcaatga ccattccgtc cgggtacgat aacctcaaac ttgagggtta  12720
ttacgcttgg ctggcttttt tgtccttttc ttacgcagcc caatttcatc cagagttgtt  12780
cggaataggg aatgtgtcac gcgtcttcgt ggataaacgg caccagttca tctgtgccga  12840
gcacgacgga caaaattcaa ccgtatccac cgaacataat atttccgcat tgtatgcggc  12900
gtactaccac caccaggtag acgggggcaa ttggttccac ctggaatggc tgcggccttt  12960
cttttcctcc tggctagtac tcaatatttc atggtttctg aggcgttcgc ctgcaagccc  13020
tgtttctcga cgcatttatc agatattgag accaacacga ccgcggctgc cggtttcatg  13080
gtccttcagg acatcaactg tttccacagt ggctcagagg cacaaacgac tggtcccatc  13140
agaaagtcgt cccaatgccg tgaagccgtc ggcactcccc agtacatcaa gataacggcc  13200
aatctgaccg acgaatcata cttgtacaac gcggacttgc tgatgctttc tgcgtgcctt  13260
ttctacgcct cagagatgag cgagaaaggc tttaaagtca tttttgggaa tgtctctggc  13320
gttgtctccg cttgtgtcaa ttttacagat tatgtggccc atctgaccca acatacccag  13380
cagcatcatt tggtaaccaa tcacattcgg ttgctacatt tcctgacacc atcagcgatg  13440
aggtgggcta caaccattgc ttgtttgttc gccattctct tggcgatatg agatgttctc  13500
acaaatcggg gtgtttcttg actccgcact cttgcttttg gtggtttttt ttgctgtgta  13560
ccggcttgtc ctggtccttt gccgatggca acggcgacag ctcgacatac caatatatat  13620
ataacttgac gatatgcgag ctgaatggga ccgaatggct gtctgaccat tttaattggg  13680
cagtcgagac ttttgtgctc tacccagtgg cgactcatat cctctcactg ggtttcctca  13740
cgacaagtca tttccttgat gcgttcggtc ttggagctgt gtcaattaca gggttttgtg  13800
```

gcgggcggta cgtgctcagc agcgtgtacg gcgcttgtgc actagcagcg ctcgtatgtt 13860
ttgttatccg tgctgccaaa aattgtatgg cttgccgcta tgctcgtacc cggtttacca 13920
acttcattgt ggatgaccgg gggagaatcc atcggtggag gtctccaata gtggtggaaa 13980
aattaggtaa agctgacgtc ggcggcgacc ttgtcaccat caaacatgtc atcctcgaag 14040
gagtcaaagc tcaacccttg acgaggactt cggccgagca atgggaggcc tagataattt 14100
ctgcaacgat cccaccgccg cacaaaagct tgtgctagcc tttagcatca cgtatacacc 14160
catcatgata tacgccctta aggtgtcacg cggccgactc ttggggttgt tgcacatctt 14220
gatatttctg aactgttctt tcacgttcgg atacatgaca tatatgcatt ttgaatccac 14280
caaccgtgtc gcgcttacca tggggggcgt tgtcgccctt ctgtggggcg tttatagttt 14340
catagagtca tggaagttta tcacttccag atgcagattg tgttgcctag gccggcgata 14400
cattctggcc cctgcccacc acgtagaaag tgctgcaggc ctccatccga tcccagcgtc 14460
tggtaaccaa gcatacgctg tgagaaagcc cggactaaca tcagtgaacg gcactctggt 14520
accaggactt cgaggcctcg tgctgggcgg caaacgagct gttaaacgag gagtggttaa 14580
cctcgtcaag tatggccggt aaaaaccaga gccagaagaa aaagaaaaat ccagctccaa 14640
tggggaatgg ccagtcagtc aatcaactgt gccagctgct gggcacaatg ataaagtccc 14700
agcgccagcg acccagggga ggacaggcta aaaagaaaaa gcctgagaag ccacatttcc 14760
ccctggctgc tgaagatgac gtccggcacc atctcaccca gaccgagcgc tccctttgct 14820
tgcaatcgat ccagacggct tttaatcaag gcgcaggaac tgcgtcgctt tcatccagcg 14880
ggaagatcgg ttttcaggtt gagtttatgc taccggttgc tcatacagtg cgcctgattc 14940
gcgtgacttc tacatccgcc ggtcaggatg caaattaatt tgatagtcag gtgaatggcc 15000
gcgattggcg tgtggcctct gagtcaccta ttcaattagg gcgatcacat gggggtcaga 15060
cttaattagg caggaaccat gtgaccgaaa tt 15092

<210> SEQ ID NO 6
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 6
gcaccacctc acccagac 18

<210> SEQ ID NO 7
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 7
cagttcctgc gccttgat 18

<210> SEQ ID NO 8
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 8
cctctgcttg caatcgatcc agac 24

EFFECTIVE VACCINATION AGAINST EUROPEAN STRAINS OF PORCINE REPRODUCTIVE AND RESPIRATORY SYNDROME (PRRS) VIRUS PRIOR TO WEANING

The present application represents the United States national stage (35 USC 371) of international application PCT/US2017/066347, internationally filed on Dec. 14, 2017, and claims the benefit under 35 USC 119 of U.S. provisional application 62/434,144 filed Dec. 14, 2016.

FIELD OF THE INVENTION

The present invention provides vaccines that protect swine of all ages, both male and female, against European strains of porcine reproductive and respiratory syndrome (PRRS) virus. The present invention particularly provides for the safe and early vaccination of piglets prior to weaning, including from immediately after birth (i.e. only about 1 day of age or less) to three weeks of age, at all times optionally in combination with multivalent combination swine vaccines, such as bivalent PRRSV/*Mycoplasma hyopneumoniae* (*M.hyo*) vaccines, bivalent PRRSV/Porcine Circovirus type 2 (PCV2) vaccines, and trivalent PRRSV/*M.hyo*/PCV2 vaccines, or simply as a monovalent PRRSV vaccine, wherein the PRRS vaccine component generally corresponds to a genotype thereof (and sub-types of said genotype) recognized as circulating on the European continent, to include both Western Europe, Mediterranean regions, Scandinavian regions, and Eastern Europe such as Russia, Turkey, and the Ukraine.

The present invention is broadly directed to novel classes of attenuated European PRRS strains which, in modified live form, are both remarkably safe and effective when given even to the youngest animals as vaccines, and provide very long duration of immunity.

BACKGROUND OF THE INVENTION

Porcine reproductive and respiratory syndrome (PRRS) is characterized by abortions, stillbirths, and other reproductive problems in sows and gilts, as well as respiratory disease in young pigs. The causative agent is the PRRS virus (PRRSV), a member of the family Arteriviridae and the order Nidovirales. The nidoviruses are enveloped viruses having genomes consisting of a single strand of positive polarity RNA. The genomic RNA of a positive-stranded RNA virus fulfills the dual role in both storage and expression of genetic information. No DNA is involved in replication or transcription in Nidoviruses. The non-structural proteins are translated directly from the genomic RNA of nidoviruses as large polyproteins and subsequently cleaved by viral proteases into discreet functional proteins. A 3'-coterminal nested set of subgenomic RNAs (sgRNAs) is synthesized from the genome and are used as messenger RNAs for translation of the structural proteins. The reproduction of nidoviral genomic RNA is thus a combined process of genome replication and sgRNA synthesis.

In the late 1980's, two distinct genotypes of the virus emerged nearly simultaneously, one in North America and another in Europe. PRRS virus is now endemic in nearly all swine producing countries, and is considered one of the most economically important diseases affecting the global pork industry. Additionally, highly virulent genotypes have been isolated in China and surrounding countries, and such genotypes are generally closely related to North American genotypes.

Despite significant advances in understanding the biology of PRRSV, control of the virus remains difficult. Vaccination of animals in the field has proven to be largely ineffective. PRRS commonly re-emerges in immunized herds, and most on-farm PRRSV vaccination campaigns ultimately fail to control the disease.

Without being limited as to theory, infection of pigs with wild type PRRSV or their vaccination with a live attenuated form of this pathogen unfortunately only elicits an exuberant production of non-neutralizing antibodies. During this time interval, for example, only limited quantities of interferon (IFN)-γ secreting cells are generated. Thus, PRRSV seems to inherently stimulate an imbalanced immune response distinguished by consistently abundant humoral (antibody-based) immunity, and a variable and limited but potentially protective T helper (Th) 1-like IFN-γ response. One characteristic of PRRSV infection that most likely contributes to the imbalanced development of adaptive immunity is the lack of an adequate innate immune response. Usually, virus-infected cells secrete type I interferon "IFN" (including IFN-α and IFN-β), which protects neighboring cells from infection. In addition, the released type I IFN interacts with a subset of naïve T cells to promote their conversion into virus-specific type II IFN (IFN-γ) secreting cells. In contrast, the IFN-α response of pigs to PRRSV exposure is nearly non-existent. Such inefficient stimulation of IFN-α production by a pathogen would be expected to have a significant impact on the nature of the host's adaptive immune response, since IFN-α up-regulates IFN-γ gene expression. Accordingly, the former cytokine likely controls the dominant pathway that promotes the development of adaptive immunity, namely, T cell-mediated IFN-γ responses and peak antiviral immune defenses.

In this regard, it has become evident that a probable link between innate and adaptive immunity in viral infections occurs through a special type of dendritic cell which has the ability to produce large amounts of type I interferon, and which plays a critical role in the polarization of T-cell function. Specifically, an infrequent but remarkable type of dendritic cell, the plasmacytoid dendritic cell (PDC), also known as a natural IFN-α/β-producing cell, plays a critical role in anti-viral immunity by means of their ability to cause naïve T cells to differentiate into IFN-γ secreting cells. Although rare, the PDC are enormously potent producers of IFN-α, with each cell being capable of producing 3-10 pg of IFN-α in response to virus. In contrast, monocytes produce 5- to 10-fold less IFN-α on a per cell basis. The phenotype and some biological properties of porcine PDC have been described (Summerfield et al., 2003, Immunology 110:440). Recent studies have determined that PRRSV does not stimulate porcine PDCs to secrete IFN-α (Calzada et al., 2010, Veterinary Immunology and Immunopathology 135:20).

This fact, in combination with the observation that exogenously added IFN-α at the time of vaccination has been found to improve the intensity of the PRRSV-specific IFN-γ response (W. A. Meier et al., Vet. Immunol. Immunopath. 102, pp 299-314, 2004), highlights the critical role that IFN-α plays during the infection of pigs with this virus. Given the apparent critical role of IFN-α on the development of protective immunity, it is important to determine the ability of different PRRS virus stocks to stimulate and/or inhibit the production of IFN-α. Accordingly, there is a pressing need for new and improved modified live vaccines to protect against PRRS.

European PRRS is generally denominated 'type 1' to distinguish it from distantly related North American or "type 2" PRRS, and the two types are only about 60% identical, on a total nucleotide level. The first clearly defined European PRRSV isolate was disclosed by Wensvoort et al., as the Lelystad agent (see Institut Pasteur Isolate 1102, and U.S. Pat. Nos. 5,620,691 and 6,197,310 and their international counterparts). The various subtypes of European PRRS (all of which can be protected against in all aspects of the present invention) are further elaborated in M. P. Murtaugh et al., Virus Research, Vol 154, pp. 18-30, 2010; and M. Shi et al., Virus Research, vol 154 pp. 7-17, 2010. Early North American PRRS isolates are disclosed in U.S. Pat. Nos. 5,476,778 and 5,840,563.

The present inventors have discovered that it is possible to provide attenuated forms of European PRRS strains that prove both safe and effective when given to the youngest of animals, and that unlike many other currently available PRRS vaccines, do not disable many aspects of the animal's immune response mechanisms, such as those aforementioned, thereby further contributing to safety and efficacy. As is well known in the art, it has proved very difficult to culture PRRS virus. Historically, monkey kidney cell line MA-104 and its derivatives have been used almost exclusively for the propagation and attenuation of commercial modified live PRRSV vaccines, although it was not known why such cells were operable for this purpose (see U.S. Pat. No. 5,476,778).

The discovery that the mammalian cell surface protein "CD163" is naturally used by PRRS virus to enter mammalian cells (see for example U.S. Pat. No. 9,102,912) has permitted the development of new PRRSV-permissive cell lines. Surprisingly, attenuation on these newer cell lines yields vaccine viruses with properties that differ from existing vaccines (see U.S. Pat. No. 9,566,324 and U.S. application publication 2013-0309263)

Accordingly, it has been surprisingly discovered that European PRRS viruses adapted to culture on either (1) porcine cells or (2) non-porcine cells that incorporate the porcine CD163 receptor (see U.S. Pat. No. 7,754,464) retain a safety and efficacy profile that is more meaningful to porcine animals than that provided by vaccine viruses cultured by traditional methods, and further that protective immunity can be achieved even with early age vaccinations. It thus appears that the routine adaptation of PRRS to culture in monkey kidney cell line MA-104 (which oddly expresses simian CD163 possibly in relation to a hemoglobin scavenging function, and wherein said simian CD163 is only about 85% identical to porcine CD163) leads to a safety/efficacy profile that will always be less biologically relevant and non optimal. Representative examples of porcine CD163 are described in U.S. Pat. No. 7,754,464 and its related family members, U.S. Pat. Nos. 8,058,050; 8,486,685; and 9,102,912 (see, for example, SEQ ID: NO:14 and SEQ ID NO:2 therein). As further described in this patent family, as applicable to the practice of the present invention, it is not necessary for the recombinant expression cell to express full length CD163, as long as the CD163 polypeptide has a transmembrane domain to anchor in the membrane and expresses its surface exposed domains, thus the C-terminal domain may be absent or reduced.

Additionally, vaccines of the present invention are expected to not downregulate host interferon response, whereas prior art vaccines such as Ingelvac MLV (see U.S. Pat. Nos. 5,476,778 and 5,846,805) that are adapted to culture in simian cells (that provide only simian CD163 as receptor) generally show strong inhibitory effect on host IFN-alpha response (see Example 5 generally, and FIG. 4 in U.S. Pat. No. 9,566,324).

PRRS virus normally generates the most severe symptoms in the youngest of animals, and being able to provide a vaccination that is both safe and efficacious to a piglet that is only one day old, for example, substantially contributes to husbandry in the industry, not only by decreasing mortality in young piglets, but also permitting the movement of animals between facilities at the earliest possible time post-weaning.

A further aspect of the invention provides the recognition that current European simian cell-based vaccines can be improved by re-adapting the underlying viruses either to grow in appropriate porcine cells (see discussion, for example, of PK-9 cells below) or non-porcine cells that express porcine CD163, with the result that the vaccines are generally safer, and can safely elicit a robust and enduring immune response at a much earlier age. Thus, the typical safety and efficacy requirements associated with traditional vaccines that have been prepared in simian cells (i.e. that such vaccines be given at only about 3 weeks of age or later) can be obviated with improved performance, also achieving effectiveness as early as day 1 of life. Thus, given the wide variety of types, subtypes and strains of PRRSV, the methods of the present invention can also be used to improve the current relevance and effectiveness of many preexisting live PRRS vaccines.

That Type 2 (North American) PRRS vaccines can be safe and effective when administered pre-weaning has been earlier reported in regard of North American/Asian strains of PRRS (see WO2013/173443 at Examples 9 and 10, for example), particularly referencing attenuates of the "P129 strain" of North American PRRS virus (see SEQ ID NO:6 therein, for example, and also PCT/IB2011/055003 and U.S. Pat. No. 6,500,662). However, European and North American PRRS viruses are only about 60% identical at a nucleotide level, and behave in somewhat different ways, as to the types of pathologies seen, in different classes of animals (age, sex, and the like).

Here we describe the use of porcine CD163-expressing cell lines to attenuate and select Genotype 1 (European) PRRSV strains having excellent properties as vaccines.

SUMMARY OF THE INVENTION

In a first embodiment, the present invention provides an isolated polynucleotide molecule including a DNA sequence encoding an infectious RNA molecule encoding a PRRS virus that is genetically modified such that, as a vaccine, it elicits an effective immunoprotective response against the PRRS virus in porcine animals. In certain aspects, the invention provides for a DNA sequence as set forth herein including SEQ ID NO:5. Encoding sequences that are at least 80% identical to SEQ ID NO:5 (and more preferably having 85%, 90%, 95%, 96%, 97%, 98% or 99% identity thereto) are also operable in the practice of the present invention, as long as they provide various key mutations, as described below, that distinguish said isolates from other or precursor strains.

A further embodiment of the invention includes the RNA sequences corresponding to the aforementioned DNA polynucleotides, and that can be expressed therefrom, and the actual viruses that can be assembled from such expression. Additional attenuated European PRRS viruses useful in the practice of the invention include those that are encoded by a DNA sequence that hybridizes to the complement of a DNA sequence of SEQ ID NO:5 under highly stringent conditions which comprise hybridization to filter bound DNA in 0.5 M NaHPo4, 7% SDS, 1 mM EDTA at 65 degrees C., and washing in 0.1 SSC/0/1% SDS at 68 degrees C.

For the purposes of the invention, "corresponding" means that the relative sequences can be optimally aligned using a BLOSUM algorithm as described in Henikoff et al. Proc Natl. Acad. Sci., USA, 89, pp. 10915-10919, 1992.

In certain embodiments, the invention provides for a plasmid that includes an isolated polynucleotide molecule as set forth herein and a promoter capable of transcribing the polynucleotide molecule in a suitable host cell. In another embodiment, the European PRRS encoding sequence of the plasmid herein further encodes one or more detectable heterologous antigenic epitopes. The present invention provides for a transfected host cell that includes the plasmid set forth herein.

In another aspect, the present invention provides for a vaccine for protecting a porcine animal from infection by a PRRS virus. The vaccine may include a Euoprean PRRS virus encoded by an infectious RNA molecule, the infectious RNA molecule, each of which is encoded by the isolated polynucleotide molecule as set forth herein. In yet another aspect, the vaccine includes a plasmid or viral vector including the polynucleotide herein. The vaccine set forth herein may optionally include a vaccine carrier acceptable for veterinary use. In one important aspect, the vaccine has a decreased interferon-α inhibitory effect as compared to wild-type European viruses and other available vaccines.

In one embodiment, the present invention provides for diagnostic kit including polynucleotide molecules which distinguish (a so-called DIVA test) between porcine animals naturally infected with a field strain of a PRRS virus and porcine animals vaccinated with the modified live vaccine set forth herein.

In other embodiments, the invention provides for a method of protecting a porcine animal from infection with a strain of PRRS virus, including administering to the animal an immunogenically protective amount of the vaccine of the claims set forth herein.

The present invention also provides a plasmid capable of directly transfecting a suitable host cell and expressing a Porcine Reproductive and Respiratory Syndrome Virus (PRRS) from the suitable host cell so transfected, which plasmid comprises: (a) a DNA sequence encoding an infectious RNA molecule encoding the PRRS virus, and (b) a promoter capable of transcribing said infectious RNA molecule.

In further preferred embodiments, said plasmid contains a promoter that is a eukaryotic promoter capable of permitting a DNA launch in targeted eukaryotic cells, or a prokaryotic or phage promoter capable of directing in vitro transcription of the plasmid. The invention similarly provides a method of generating a PRRS virus, which method comprises transfecting a suitable host cell with an appropriate plasmid and obtaining PRRS virus generated by the transfected cell.

The invention also provides for host cells transfected with polynucleotide molecules and provides vaccines for protecting a porcine animal against infection by a PRRS virus, which vaccine comprises: (a) a genetically modified European PRRS virus encoded by such aforementioned polynucleotide molecules, or (b) said infectious molecule, or (c) said polynucleotide molecule in the form of a plasmid, or (d) a viral vector comprising said polynucleotide molecule, wherein the PRRS virus is able to elicit an effective immunoprotective response against infection by PRRS virus, in an amount effective to produce immunoprotection against infection, and a carrier suitable for veterinary use.

Particularly, the invention includes a method for generating a European Porcine Reproductive and Respiratory Syndrome (PRRS) virus, which method comprises transfecting a suitable eucaryotic host cell with a composition selected from the group consisting of:

(a) a plasmid comprising (1) a DNA sequence encoding an infectious RNA molecule encoding a European PRRS virus, wherein said encoding DNA sequence is SEQ ID: NO:5, or an encoding DNA sequence that is at least 85% identical to SEQ ID NO:5, and (2) a promoter capable of driving transcription of said DNA sequence encoding said infectious RNA molecule in said suitable host cell; and (b) an infectious PRRS RNA molecule produced from in vitro transcription of a plasmid comprising a DNA sequence encoding said infectious PRRS RNA molecule encoding a European PRRS virus, wherein said encoding DNA sequence is SEQ ID: NO:5, or an encoding DNA sequence that is at least 85% identical to SEQ ID NO:5, wherein, for cases (a) and (b) an encoding sequence is used that is at least 85% identical to SEQ ID NO:5 and contains one or more particular mutations compared to a reference sequence.

In preferred examples, both protective and safe vaccination may be provided to the piglet (whether male or female) in a single dose at less than one day of age, such as 8-16 hours after birth, out to two weeks of age, or three weeks of age, taking into account that the piglet may be weaned at any point from about two to three weeks of age. Thus the present invention is generally applicable to single-dose early vaccination, meaning at any time on the first day of life (from birth to 24 hours of age), similarly on Day 2, Day 3, Day 4, Day 5, Day 6, Day 7, Days 1-10, Days 1-14, and Days 1-21, or simply vaccination that is conducted earlier than approximately the day of weaning. Two or more doses can optionally be used.

Early vaccination (typically by the intramuscular or intranasal route) against porcine reproductive and respiratory syndrome virus (PRRSV) under such conditions also provides an early onset of protective immunity, such as by about one to eight weeks of age; or between about two to six weeks following vaccination; and commonly by about 28 days following vaccination.

Vaccination according to the practice of the invention typically provides a duration of immunity to the piglet that is about 23-28 weeks, typically at least about 26 weeks, which is the full expected life of a market pig. Thus vaccine programs made possible by the present invention protect piglets when they are most vulnerable to infection and are most easily handled. Such vaccination also permits onset of immunity to coincide with when weaned piglets are removed from the sow, and may be transported to other facilities where further risk of infection by PRRSV may be present. The vaccines of the invention are also highly effective in protecting boars; and sows and gilts, thus indirectly protecting unborn offspring. Although intramuscular and intranasal vaccination is preferably contemplated, other routes are also applicable.

In a further example of the invention, although it is less preferred, the CD163 polypeptide expressed by the recombinant cells in which the European PRRS virus is cultured (and thus pre-adapted to infection and growth in porcine animals) is not porcine CD163, but rather is a mammalian CD163 having an amino acid sequence that is relatively close to the porcine sequence, such as at least 90% identical to SEQ ID NOS 2 or 14 of U.S. Pat. No. 7,754,464. More preferably, this amino acid identity, 92%, 95%, 96%, 97%, 98% or 99%.

The invention also provides diagnostic kits comprising polynucleotide molecules which distinguish between porcine animals naturally infected with a field strain of a PRRS virus and porcine animals vaccinated with the vaccines of the invention, which vaccines (viruses) preferably evidence a decreased interferon-α inhibitory effect as compared to wild-type.

The invention further provides representative whole genome sequences of PRRSV derived from European (Belgian) PRRSV isolate 96V198. Isolate 96V198 itself was obtained in 1996 by Professor Hans Nauwynck, Ghent University, Belgium, from the lungs of a young pig with respiratory signs (Passage 0 was thus recovered from the serum of an infected pig (SEQ ID NO:1).

Passage 1 (SEQ ID NO:2) is the result of a single passage on primary porcine alveolar macrophages (PAMs). All subsequent passages were performed on the BHK21-C12-26 cell line. Passage 9 (SEQ ID NO:3) is immediately prior to biological cloning of the virus by three rounds of limiting dilution. Passage 14 (SEQ ID NO:4) is clone 1 (of six clones examined and evaluated). Clone 1 continued to become Master Seed Virus at passage 44, and MSV+5 passages became Suvaxyn® PRRS MLV product at passage 49 (SEQ ID NO:5). All genomes are 15,092 nt long. All genomes are at least 99.5% identical to each other, and are about 92% identical to Lelystad virus.

BRIEF DESCRIPTION OF THE FIGURES

FIG. 1 provides the full length nucleotide sequence (15,092 bases) of the passage 49 isolate for the Suvaxyn® PRRS MLV product, SEQ ID NO:5.

BRIEF DESCRIPTION OF THE SEQUENCE LISTING

SEQ ID NO:1 provides passage 0 of PRRSV isolate 96V198.

SEQ ID NO:2 provides passage 1 of PRRSV isolate 96V198.

SEQ ID NO:3 provides passage 9 of PRRSV isolate 96V198.

SEQ ID NO:4 provides passage 14 of PRRSV isolate 96V198.

SEQ ID NO:5 provides passage 49 of PRRSV isolate 96V198.

SEQ ID NOS: 6-8 provide PCR primer sequences.

DETAILED DESCRIPTION OF THE INVENTION

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

"North American PRRS virus" means any PRRS virus having genetic characteristics associated with a North American PRRS virus isolate, such as, but not limited to the PRRS virus that was first isolated in the United States around the early 1990's (see, e.g., Collins, J. E., et al., 1992, J. Vet. Diagn. Invest. 4:117-126); North American PRRS virus isolate MN-1b (Kwang, J. et al., 1994, J. Vet. Diagn. Invest. 6:293-296); the Quebec LAF-exp91 strain of PRRS (Mardassi, H. et al., 1995, Arch. Virol. 140:1405-1418); and North American PRRS virus isolate VR 2385 (Meng, X.-J et al., 1994, J. Gen. Virol. 75:1795-1801). Genetic characteristics refer to genomic nucleotide sequence similarity and amino acid sequence similarity shared by North American PRRS virus strains. Asian PRRS virus strains generally evidence about 80-95% nucleotide sequence identity with North American strains (see the default values for the Clustal W algorithm in the Lasergene software suite, DNASTAR, Inc.), and North American strains are similarly about 85% to 100% identical to each other.

"European PRRS virus" (PRRSV-1, or formerly PRRSV Type 1) refers to any strain of PRRS virus having the genetic characteristics associated with the PRRS virus that was first isolated in Europe around 1991 (see, e.g., Wensvoort, G., et al., 1991, Vet. Q. 13:121-130, the Lelystad virus, see also U.S. Pat. Nos. 5,620,691 and 6,197,310). European PRRS virus also generally refers to viruses having full length nucleotide sequences that are about 80% identical or higher to the Lelystad isolate. It should be noted that within PRRSV-1, subtypes have come to be identified, so that Lelystad virus has been denominated the prototype for subtype 1, and the Lena virus (U. Karniychuk et al., BMC Veterinary Research, 2010, Vol 6, No. 30) has become denominated as the prototype of subtype 3. These two viruses approximately span the maximum current divergence of PRRSV-1, and thus, for example, using ORF5, Lelystad and Lena are about 82.8% identical at the nucleotide level, and using full genomes, Lelystad and Lena are about 80.7% identical at the nucleotide level. Optimization of alignments varies slightly based on algorithm parameters, but the reader is generally referred to the default values for the Clustal W algorithm in the Lasergene software suite (DNASTAR, Inc.).

European PRRS strains are generally only about 60% identical to both North American and Asian (Chinese) strains. For example, using ORF5 nucleotide sequence (which tends to give a good to fair estimate of entire genome when entire genomes are not known), the PRRSV-1 prototype Lelystad Virus and the North American prototype VR2332 strain are about 65.0% identical at the nucleotide level. Using full genome nucleotide sequence, the prototype Lelystad Virus and the prototype VR2332 virus are about 58.6% identical at the nucleotide level, again using the default values for the cited Clustal W algorithm.

"An effective immunoprotective response", "immunoprotection", and like terms, for purposes of the present invention, mean an immune response that is directed against one or more antigenic epitopes of a pathogen so as to protect against infection by the pathogen in a vaccinated animal. For purposes of the present invention, protection against infection by a pathogen includes not only the absolute prevention of infection, but also any detectable reduction in the degree or rate of infection by a pathogen, or any detectable reduction in the severity of the disease or any symptom or condition resulting from infection by the pathogen in the vaccinated animal as compared to an unvaccinated infected animal. An effective immunoprotective response can be induced in animals that have not previously been infected with the pathogen and/or are not infected with the pathogen at the time of vaccination. An effective immunoprotective response can also be induced in an animal already infected with the pathogen at the time of vaccination.

A genetically modified PRRS virus is "attenuated" if it is less virulent than its unmodified parental strain. A strain is "less virulent" if it shows a statistically significant decrease in one or more parameters determining disease severity. Such parameters may include level of viremia, fever, severity of respiratory distress, severity of reproductive symptoms, or number or severity of lung lesions, etc.

"Host cell capable of supporting PRRS virus replication" means a cell which is capable of generating infectious PRRS when infected with a virus of the invention. Such cells include porcine cells of the monocyte/macrophage lineage such as porcine alveolar macrophage cells and derivatives, MA-104 monkey kidney cells and derivatives such as MARC-145 cells; and cells transfected with a gene encoding a receptor for the PRRS virus (see U.S. Pat. No. 9,102,912 referring to assignment of the mammalian CD163 surface protein as the normal PRRS virus cell receptor). The term "host cell capable of supporting PRRS virus replication" may also include cells within a live pig.

"Open reading frame", or "ORF", as used herein, means the minimal nucleotide sequence required to encode a particular PRRS virus protein without an intervening stop codon.

"Porcine" and "swine" are used interchangeably herein and refer to any animal that is a member of the family Suidae such as, for example, a pig. The vaccines and method protocols of the invention are applicable to all swine, whether male of any age, or female of any age to include sows and gilts, and such methods also are capable of protecting male and female piglets indirectly via protection administered to the mother sow. The term "PRRS virus", as used herein, unless otherwise indicated, means any strain of either the North American, Asain or European PRRS viruses.

"PRRS" encompasses disease symptoms in swine caused by a PRRS virus (PRRSV) infection. Examples of such symptoms include, but are not limited to, fever, abortion in pregnant females, respiratory distress, lung lesions, loss of appetite, and mortality in young pigs. As used herein, a PRRS virus that is "unable to produce PRRS" refers to a virus that can infect a pig, but which does not produce any disease symptoms normally associated with a PRRS infection in the pig.

"Transfected host cell" means practically any host cell which, when transfected with PRRS virus RNA, can produce at least a first round of PRRS virions.

An "infectious DNA molecule", for purposes of the present invention, is a DNA molecule that encodes the necessary elements to support replication, transcription, and translation into a functional virion from a suitable host cell.

Likewise, an "isolated polynucleotide molecule" refers to a composition of matter comprising a polynucleotide molecule of the present invention purified or controlled to any detectable degree from its naturally occurring state, if any.

For purposes of the present invention, the nucleotide sequence of a second polynucleotide molecule (either RNA or DNA) is "homologous" to the nucleotide sequence of a first polynucleotide molecule, or has "identity" to said first polynucleotide molecule, where the nucleotide sequence of the second polynucleotide molecule encodes the same polyaminoacid as the nucleotide sequence of the first polynucleotide molecule as based on the degeneracy of the genetic code, or when it encodes a polyaminoacid that is sufficiently similar to the polyaminoacid encoded by the nucleotide sequence of the first polynucleotide molecule so as to be useful in practicing the present invention. Homologous polynucleotide sequences also refers to sense and anti-sense strands, and in all cases to the complement of any such strands. For purposes of the present invention, a polynucleotide molecule is useful in practicing the present invention, and is therefore homologous or has identity, where it can be used as a diagnostic probe to detect the presence of PRRS virus or viral polynucleotide in a fluid or tissue sample of an infected pig, e.g. by standard hybridization or amplification techniques. Generally, the nucleotide sequence of a second polynucleotide molecule is homologous to the nucleotide sequence of a first polynucleotide molecule if it has at least about 70% nucleotide sequence identity to the nucleotide sequence of the first polynucleotide molecule as based on the BLASTN algorithm (National Center for Biotechnology Information, otherwise known as NCBI, (Bethesda, Md., USA) of the United States National Institute of Health). In a specific example for calculations according to the practice of the present invention, reference is made to BLASTP 2.2.6 [Tatusova TA and TL Madden, "BLAST 2 sequences—a new tool for comparing protein and nucleotide sequences." (1999) FEMS Microbiol Lett. 174:247-250.]. Briefly, two amino acid sequences are aligned to optimize the alignment scores using a gap opening penalty of 10, a gap extension penalty of 0.1, and the "blosum62" scoring matrix of Henikoff and Henikoff (Proc. Nat. Acad. Sci. USA 89:10915-10919. 1992). The percent identity is then calculated as: Total number of identical matches×100/divided by the length of the longer sequence+number of gaps introduced into the longer sequence to align the two sequences.

Preferably, a homologous nucleotide sequence has at least about 75% nucleotide sequence identity, even more preferably at least about 80%, 85%, 90% 95%, 96%, 97%, 98% and 99% nucleotide sequence identity. Since the genetic code is degenerate, a homologous nucleotide sequence can include any number of "silent" base changes, i.e. nucleotide substitutions that nonetheless encode the same amino acid.

A homologous nucleotide sequence can further contain non-silent mutations, i.e. base substitutions, deletions, or additions resulting in amino acid differences in the encoded polyaminoacid, so long as the sequence remains at least about 70% identical to the polyaminoacid encoded by the first nucleotide sequence or otherwise is useful for practicing the present invention.

In this regard, certain conservative amino acid substitutions may be made which are generally recognized not to inactivate overall protein function: such as in regard of positively charged amino acids (and vice versa), lysine, arginine and histidine; in regard of negatively charged amino acids (and vice versa), aspartic acid and glutamic acid; and in regard of certain groups of neutrally charged amino acids (and in all cases, also vice versa), (1) alanine and serine, (2) asparagine, glutamine, and histidine, (3) cysteine and serine, (4) glycine and proline, (5) isoleucine, leucine and valine, (6) methionine, leucine and isoleucine, (7) phenylalanine, methionine, leucine, and tyrosine, (8) serine and threonine, (9) tryptophan and tyrosine, (10) and for example tyrosine, tyrptophan and phenylalanine. Amino acids can be classified according to physical properties and contribution to secondary and tertiary protein structure. A conservative substitution is recognized in the art as a substitution of one amino acid for another amino acid that has similar properties. Exemplary conservative substitutions may be found in WO 97/09433, page 10, published Mar. 13, 1997 (PCT/GB96/02197, filed Sep. 6, 1996. Alternatively, conservative amino acids can be grouped as described in Lehninger, (Biochemistry, Second Edition; Worth Publishers, Inc. NY:NY (1975), pp. 71-77). Additional suitable conservative changes and the application thereof are described below.

Homologous nucleotide sequences can be determined by comparison of nucleotide sequences, for example by using BLASTN, above. Alternatively, homologous nucleotide sequences can be determined by hybridization under selected conditions. For example, the nucleotide sequence of a second polynucleotide molecule is homologous to SEQ ID NO:5 (or any other particular polynucleotide sequence) if it hybridizes to the complement of SEQ ID NO:5 under moderately stringent conditions, e.g., hybridization to filter-bound DNA in 0.5 M $NaHPO_4$, 7% sodium dodecyl sulfate (SDS), 1 mM EDTA at 65° C., and washing in 0.2×SSC/0.1% SDS at 42° C. (see Ausubel et al editors, Protocols in Molecular Biology, Wiley and Sons, 1994, pp. 6.0.3 to 6.4.10), or conditions which will otherwise result in hybridization of sequences that encode a PRRS virus as defined below. Modifications in hybridization conditions can be empirically determined or precisely calculated based on the length and percentage of guanosine/cytosine (GC) base pairing of the probe. The hybridization conditions can be calculated as described in Sambrook, et al., (Eds.), *Molecular Cloning: A Laboratory Manual*, Cold Spring Harbor Laboratory Press: Cold Spring Harbor, N.Y. (1989), pp. 9.47 to 9.51.

In another embodiment, a second nucleotide sequence is homologous to SEQ ID NO:5 (or any other sequence of the invention) if it hybridizes to the complement of SEQ ID NO:5 under highly stringent conditions, e.g. hybridization to filter-bound DNA in 0.5 M $NaHPO_4$, 7% SDS, 1 mM EDTA at 65° C., and washing in 0.1×SSC/0.1% SDS at 68° C., as is known in the art (Ausebel et al. Current Protocols in Molecular Biology, Greene Publishing and Wiley Interscience, New York, 1989.

It is furthermore to be understood that the isolated polynucleotide molecules and the isolated RNA molecules of the present invention include both synthetic molecules and molecules obtained through recombinant techniques, such as by in vitro cloning and transcription.

Polynucleotide molecules can be genetically mutated using recombinant techniques known to those of ordinary skill in the art, including by site-directed mutagenesis, or by random mutagenesis such as by exposure to chemical mutagens or to radiation, as known in the art." The mutations may be carried out by standard methods known in the art, e.g. site directed mutagenesis (see e.g. Sambrook et al. (1989) Molecular Cloning: A Laboratory Manual, 2nd Ed., Cold Spring Harbor Laboratory Press, Cold Spring Harbor, N.Y.) of an infectious copy as described (e.g. Meulenberg et al., Adv. Exp. Med. Biol., 1998, 440:199-206).

In connection with providing preferred European PRRS virus sequences that are both safe and effective when administered to pre-weaning piglets, the following are among the amino acid positions that may be modified. In identifying these specific mutations, it is of course noted that conservative substitutions for these preferred amino acid residues, as defined immediately above, may also be used. In identifying the preferred encoded amino acids, the corresponding/original amino acids of the wild isolate of strain 96V198 are also shown by parenthesis, thus passage 0 (SEQ ID NO:1) is compared to passage 49 (the preferred vaccine material, SEQ ID NO:5). Thus, for the amino acid sequence encoded from ORF1a, S at amino acid position 19 (N); Y at amino acid position 24 (F); A at amino acid position 156 (T); Y at amino acid position 157 (H); D at amino acid position 268 (N); H at amino acid position 294 (Y); Y at amino acid position 416 (C); S at amino acid position 742 (P); L at amino acid position 884 (F); P at amino acid position 908 (S); K at amino acid position 916 (E); K at amino acid position 977 (E); S at amino acid position 1138 (P); F at amino acid position 1160 (L); S at amino acid position 1500 (P); R at amino acid position 2094 (Q); P at amino acid position 2254 (S); and L at amino acid position 2290 (F). For the amino acid sequence encoded from ORF1b, S at amino acid position 567 (N); and H at amino acid position 912 (Q). For the amino acid sequence encoded from ORF2a, L at amino acid position 22 (S); F at amino acid position 88 (V); M at amino acid position 94 (I); and F at amino acid position 95 (L). For the amino acid sequence encoded from ORF2b, L at amino acid position 47 (F). For the amino acid sequence encoded from ORF3, S at amino acid position 52 (T). For the amino acid sequence encoded from ORF4, T at amino acid position 151 (I). For the amino acid sequence encoded from ORF5, F at amino acid position 20 (L); and D at amino acid position 37 (N). For the amino acid sequence encoded from ORF5a, V at amino acid position 18 (A); and R at amino acid position 35 (Q).

Accordingly, the present invention further provides a method for making a genetically modified European PRRS virus, which method comprises mutating the DNA sequence encoding an infectious RNA molecule which encodes the PRRS virus as described above, and expressing the genetically modified PRRS virus using a suitable expression system. A genetically modified PRRS virus can be expressed from an isolated polynucleotide molecule using suitable expression systems generally known in the art, examples of which are described in this application. For example, the isolated polynucleotide molecule can be in the form of a plasmid capable of expressing the encoded virus in a suitable host cell in vitro, as is described in further detail below.

The North American PRRSV N protein sequences are highly conserved and the reported sequences have about 93-100% identity with each other. The North American and European PRRSV N proteins are about 57-59% identical and share common structural motifs. Generally, when comparing PRRS encoding sequences and isolates, which might be numbered differently as to specific nucleotides or encoded amino acids, identification of the proper regions are readily achieved by identifying preserved characteristic amino acids in a PRRS strain of interest and aligning it with a reference strain.

Recombinant DNA technology comprises extremely varied and powerful molecular biology techniques aimed at modifying nucleic acids at the DNA level and makes it possible to analyze and modify genomes at the molecular level. In this respect, viruses such as the PRRS virus because of the modest size of its genome is particularly amenable to such manipulations. However, recombinant DNA technology is not immediately applicable to non-retroviral RNA viruses because these viruses do not encompass a DNA intermediate step in their replication. For such viruses, infectious cDNA clones have to be developed before recombinant DNA technology can be applied to their genome to generate modified virus. Infectious clones can be derived through the construction of full-length (genomic length) cDNA (here used in the broad sense of a DNA copy of RNA and not only in the strict sense of a DNA copy of mRNA) of the virus under study, after which an infectious transcript is synthesized in vivo in cells transfected with the full-length cDNA, but infectious transcripts can also be obtained by in vitro transcription from full-length cDNA in a plasmid having a prokaryotic promoter in the presence of a transcription cocktail, or again in vitro using ligated partial-length cDNA fragments that comprise the full viral genome. In all cases, the transcribed RNA carries all the modifications that have been introduced to the cDNA and can be used to further passage the thus modified virus.

The preparation of an infectious clone of a European PRRS virus isolate or Lelystad virus is described in U.S. Pat. No. 6,268,199 which is hereby fully incorporated by reference. The preparation of an infectious cDNA clone of a North American PRRS virus isolate designated P129 (Lee et al., 2005; Yoo et al., 2004) is described in U.S. Pat. No. 6,500,662 which is hereby incorporated fully by reference. The sequence of P129 cDNA is disclosed in Genbank Accession Number AF494042 and in U.S. Pat. No. 6,500,662. Our work below makes use of such an infectious clone which in the context of a plasmid is expressed by the CMV immediate early promoter and has been designated pCMV-S-P129 and is also disclosed within U.S. Pat. No. 6,500,662. As described in U.S. Pat. No. 6,500,662 there are other plasmids and promoters suitable for use here.

Given the complete sequence of any open reading frame of interest and the location of an amino acid residue of interest, one of ordinary skill need merely consult a codon table to design changes at the particular position desired.

Codons constitute triplet sequences of nucleotides in mRNA and their corresponding cDNA molecules. Codons are characterized by the base uracil (U) when present in a mRNA molecule but are characterized by base thymidine (T) when present in DNA. A simple change in a codon for the same amino acid residue within a polynucleotide will not change the sequence or structure of the encoded polypeptide. It is apparent that when a phrase stating that a particular 3 nucleotide sequence "encode(s)" any particular amino acid, the ordinarily skilled artisan would recognize that the table above provides a means of identifying the particular nucleotides at issue. By way of example, if a particular three nucleotide sequence encodes lysine, the table above discloses that the two possible triplet sequences are AAA and AAG. Glycine is encoded by GGA, GGC, GGT (GGU if in RNA) and GGG. To change a lysine to glycine residue in an encoded protein one might replace a AAA or AAG triplet with any of by GGA and GGC, GGT or GGG in the encoding nucleic acid.

Studies on the immunobiology of PRRS virus are suggestive that the interaction of PRRS virus with PDCs merits examination. This cell type represents 0.2%-0.8% of peripheral blood mononuclear cells in humans, mice, rats, pigs and monkeys. Despite its scarcity, this cell is an important component of the innate immune system and is capable of secreting copious amounts of IFN-α following viral stimulation. It is through the secretion of IFN-α that PDCs play a major role in regulating antiviral innate and adaptive immunity since they promote the function of natural killer cells, B cells, and T cells. Furthermore, the maturation of porcine monocyte derived dendritic cells (MoDC) is aided by the IFN-α secreted by PDCs resulting in an enhanced ability of MoDCs to present antigen and activate T cells. At a later stage of viral infection, PDCs differentiate into a unique type of mature dendritic cell, which directly regulates the function of T cells and direct the differentiation of T cells into cells capable of secreting IFN-γ, which is a major mediator of antiviral immunity against viruses including PRRS virus. Not surprisingly there are human viruses, such as respiratory syncitial virus and measles virus, which are known to suppress the ability of PDCs to secrete IFN-α. This inhibitory effect is thought to play a role in the predominance of a humoral immune response and the associated immunopathology observed as a result of the infection with these viruses, as well as in the increased susceptibility of the host to secondary bacterial and viral infections.

As aforementioned, there are numerous known strains and isolates of European, North American and Chinese PRRS, and novel strains continue to evolve or to be isolated. Although a high level of amino acid sequence homology exists between all these strains, those skilled in the art will immediately recognize that some variation does exist, and indeed advantage can be taken of these differences and similarities to further improve the phenotypic properties of all vaccine strains.

First, in regard of all of the amino acid motifs defined by SEQ ID NOS as specified below, it is generally possible to inspect the corresponding expressed protein sequences from any other European PRRS, to find the corresponding amino acid motif, even if additional changes have occurred in such other strains, as a result of evolution, causing substitutions and/or deletions or additions. Thus, it should be readily possible to identify the comparable motif in another PRRS strain if, for example, the valine therein is replaced by isoleucine or leucine, or any other residue, or if a residue is simply missing or an additional residue added. Numerous computer programs exist to identify alignments and thus determine if polypeptide sequence motifs correspond, for example the so-called Blosum tables (based on a given level of percent identity), see S. Henikoff et al. "Amino Acid Substitution matrices from protein blocks", Proc Natl Acad Sci, USA, 89(22), pp. 10915-10919, Nov. 15, 1992, and see also A. L. Lehninger et al. Principles of Biochemistry, 2005, MacMillan and Company, 4$^{th}$ edition. Conservative amino acid changes are also recognized based on categorization into 5 overall groups: sulfydryl (Cys); aromatic (Phe, Tyr, and Trp); basic (Lys, Arg, His); aliphatic (Val, Ileu, Leu, Met), and hydrophilic (Ala, Pro, Gly, Glu, Asp, Gin, Asn, Ser and Thr). Thus it is within the practice of the invention to modify any European PRRS encoding nucleotide sequence to incorporate at the appropriate and corresponding position, any of the amino acid changes provided by SEQ ID NO:5 even if one or more of the other amino acids adjacent to the designated position have been added, deleted or substituted. Such amino acid changes may, of course, be introduced into the corresponding encoding nucleotide sequences of the virus by site directed mutagenesis, PCR, and other techniques as are well known in the art.

General Measure of Attenuation

To demonstrate that a particular genetically modified strain is attenuated an experiment described as follows may be used.

At least 10 gilts per group are included in each trial, which are derived from a PRRSV-free farm. Animals are tested free of PRRS virus specific serum antibodies and negative for PRRSV. All animals included in the trial are of the same source and breed. The allocation of the animals to the groups is randomized.

Challenge is performed at day 90 of pregnancy with intranasal application of 1 ml PRRSV with $10^5$ $TCID_{50}$ per nostril. There are at least three groups for each test setup: One group for wild type virus; one test group for challenge with the possibly attenuated virus; and one strict control group.

The study is deemed valid when the strict controls stay PRRSV-negative over the time course of the study and at least 25% less live healthy piglets are born in the wild type challenged group compared to the strict controls.

Attenuation, in other words less virulence, is defined as the statistical significant change of one or more parameters determining reproductive performance or other symptomology:

Significant reduction in at least one of the following parameters for the test group (possibly attenuated virus) compared to the unmodified parental strain infected group would be an indication of attenuation:

a) frequency of stillborns
b) abortion at or before day 112 of pregnancy
c) number of mummified piglets
d) number of less lively and weak piglets
e) pre-weaning mortality.

Furthermore a significant increase in one of the following parameters for the test group compared the unmodified parental strain infected group is preferred:

f) number of piglets weaned per sow
g) number of live healthy piglets born per sow.

In the alternative, respiratory symptoms and other symptoms of PRRSV infection could be examined to establish attenuation.

An attenuated strain is valuable for the formulation of vaccines. The present vaccine is effective if it protects a pig against infection by a PRRS virus. A vaccine protects a pig against infection by a PRRS virus if, after administration of the vaccine to one or more unaffected pigs, a subsequent challenge with a biologically pure virus isolate (e.g., any European wild type) results in a lessened severity of any gross or histopathological changes (e.g., lesions in the lung) and/or of symptoms of the disease, as compared to those changes or symptoms typically caused by the isolate in similar pigs which are unprotected (i.e., relative to an appropriate control). More particularly, the present vaccine may be shown to be effective by administering the vaccine to one or more suitable pigs in need thereof, then after an appropriate length of time (e.g., 4 weeks), challenging with a large sample ($10^{(3-7)}$ $TCID_{(50)}$) of a biologically pure PRRSV isolate. A blood sample is then drawn from the challenged pig after about one week, and an attempt to isolate the virus from the blood sample is then performed. Isolation of a large amount of the virus is an indication that the vaccine may not be effective, while isolation of reduced amounts of the virus (or no virus) is an indication that the vaccine may be effective.

Thus, the effectiveness of the present vaccine may be evaluated quantitatively (i.e., a decrease in the percentage of consolidated lung tissue as compared to an appropriate control group) or qualitatively (e.g., isolation of PRRSV from blood, detection of PRRSV antigen in a lung, tonsil or lymph node tissue sample by an immunoassay). The symptoms of the porcine reproductive and respiratory disease may be evaluated quantitatively (e.g., temperature/fever) or semi-quantitatively (e.g., the presence or absence of one or more symptoms or a reduction in severity of one or more symptoms, such as cyanosis, pneumonia, lung lesions etc.).

An unaffected pig is a pig which has either not been exposed to a porcine reproductive and respiratory disease infectious agent, or which has been exposed to a porcine reproductive and respiratory disease infectious agent but is not showing symptoms of the disease. An affected pig is one which shows symptoms of PRRS or from which PRRSV can be isolated.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta, Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 pg/ml Quil A, 100 [mgr]g/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 .mu.g/ml Quil A, and 50 .mu.g/ml cholesterol. Other immunomodulatory agents that can be included in the vaccine include, e.g., one or more interleukins, interferons, or other known cytokines.

Vaccines of the present invention can optionally be formulated for sustained release of the virus, infectious RNA molecule, plasmid, or viral vector of the present invention. Examples of such sustained release formulations include virus, infectious RNA molecule, plasmid, or viral vector in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279-292, which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in: Drugs and the Pharmaceutical Sciences, Vol. 45, M. Dekker, N.Y., which is also incorporated herein by reference. Alternatively, or additionally, the virus, plasmid, or viral vector can be microencapsulated to improve administration and efficacy. Methods for microencapsulating antigens are well-known in the art, and include techniques described, e.g., in U.S. Pat. Nos. 3,137,631; 3,959,457; 4,205,060; 4,606,940; 4,744,933; 5,132,117; and International Patent Publication WO 95/28227, all of which are incorporated herein by reference.

Liposomes can also be used to provide for the sustained release of virus, plasmid, or viral vector. Details concerning how to make and use liposomal formulations can be found in, among other places, U.S. Pat. Nos. 4,016,100; 4,452,747; 4,921,706; 4,927,637; 4,944,948; 5,008,050; and 5,009,956, all of which are incorporated herein by reference.

An effective amount of any of the above-described vaccines can be determined by conventional means, starting with a low dose of virus, viral protein plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies (see Examples 3-7 below).

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, protein, infectious DNA molecule, plasmid, or viral vector, of the present invention can be determined using known techniques, taking into account factors that can be determined by one of ordinary skill in the art such as the weight of the animal to be vaccinated. The dose amount of virus of the present invention in a vaccine of the present invention preferably ranges from about $10^1$ to about $10^9$ pfu (plaque forming units), more preferably from about $10^2$ to about $10^8$ pfu, and most preferably from about $10^3$ to about $10^7$ pfu. The dose amount of a plasmid of the present invention in a vaccine of the present invention preferably ranges from about 0.1 mg to about 100 mg, more preferably from about 1 mg to about 10 mg, even more preferably from about 10 mg to about 1 mg. The dose amount of an infectious DNA molecule of the present invention in a vaccine of the present invention preferably ranges from about 0.1 mg to about 100 mg, more preferably from about 1 mg to about 10 mg, even more preferably from about 10 mg to about 1 mg. The dose amount of a viral vector of the present invention in a vaccine of the present invention preferably ranges from about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

Suitable doses for viral protein or peptide vaccines according to the practice of the present invention range generally from 1 to 50 micrograms per dose, or higher amounts as may be determined by standard methods, with the amount of adjuvant to be determined by recognized methods in regard of each such substance. In a preferred example of the invention relating to vaccination of swine, an optimum age target for the animals is between about 1 and 21 days, which at pre-weening, may also correspond with other scheduled vaccinations such as against *Mycoplasma* hyopneumoniae or PCV. Additionally, a preferred schedule of vaccination for breeding sows would include similar doses, with an annual revaccination schedule.

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, infectious RNA molecule, plasmid, or viral vector, of the present invention can be determined using known techniques, taking into account factors that can be determined by one of ordinary skill in the art such as the weight of the animal to be vaccinated. By way of example, vaccines may be delivered orally, parenterally, intradermally, subcutaneously, intramuscularly, intranasally or intravenously. Oral delivery may encompass, for example, adding the compositions to the feed or drink of the animals. Factors bearing on the vaccine dosage include, for example, the weight and age of the pig.

The present invention further provides a method of preparing a vaccine comprising a PRRS virus, infectious RNA molecule, plasmid, or viral vector described herein, which method comprises combining an effective amount of one of the PRRS virus, infectious RNA molecule, plasmid, or viral vector of the present invention, with a carrier acceptable for pharmaceutical or veterinary use.

In addition the live attenuated vaccine of the present invention can be modified as described in U.S. Pat. No. 6,500,662 to encode a heterologous antigenic epitope which is inserted into the PRRS viral genome using known recombinant techniques. See also U.S. Pat. No. 7,132,106 which is incorporated by reference in its entirety. Antigenic epitopes useful as heterologous antigenic epitopes for the present invention include antigenic epitopes from a swine pathogen other than PRRS virus which include, but are not limited to, an antigenic epitope from a swine pathogen selected from the group consisting of porcine parvovirus, porcine circovirus, a porcine rotavirus, swine influenza, pseudorabies virus, transmissible gastroenteritis virus, porcine respiratory coronavirus, classical swine fever virus, African swine fever virus, encephalomyocarditis virus, porcine paramyxovirus, torque teno virus, *Actinobacillus pleuropneumoniae, Actinobacillus suis, Bacillus anthraci, Bordetella bronchiseptica, Clostridium haemolyticum, Clostridium perfringens, Clostridium tetani, Escherichia coli, Erysipelothrix rhusiopathiae, Haemophilus parasuis, Leptospira* spp., *Mycoplasma hyopneumoniae, Mycoplasma hyorhinis, Mycoplasma hyosynovia, Pasteurella multocida, Salmonella choleraesuis, Salmonella typhimurium, Streptococcus equismilis*, and *Streptococcus suis*. Nucleotide sequences encoding antigenic epitopes from the aforementioned swine pathogens are known in the art and can be obtained from public gene databases on the worldwide web, such as at Genbank from the (USA) National Center for Biotechnology Information.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention. It will be clear that the invention may be practiced otherwise than as particularly described in the foregoing description and examples.

Accordingly, a PRRS vaccine based on the SEQ ID NO:5 virus will be seen as representative of those having a safety and efficacy profile that provides the dramatic improvement of permitting successful vaccination of piglets, as early even as the first day of life, with long lasting immunity out to about 6 months of age, Such unprecedented improvements in vaccine performance are surprisingly provided by culturing and attenuating the virus in a cell culture environment that maximizes relevance to swine biology, including by permitting appropriate and safe replication of the virus in a swine host while not downregulating the needed host immune response. Such benefits are provided to piglets, boars, and sows and gilts (both before and during pregnancy); and in all cases whether the animal is seropositive or seronegative at the time of vaccination.

It is also readily apparent that the culturing improvements of the present invention are equally applicable to European PRRS viruses irrespective of whether they are, were, or come to be manipulated by recombinant means, or have only been isolated, maintained, or cultured and adapted by primarily non-recombinant means; in all cases including whether any culturing cells used are, or are not themselves recombinant.

Numerous modifications and variations of the present invention are possible in light of the above teachings and, therefore, are within the scope of the invention.

The following examples are intended to illustrate but not limit the invention.

Example 1—Generation of the BHK21-C12-26 Cell Line

The generation of the BHK21-C12 cell line, the parent of the BHK21-C12-26 cell line used in these studies, was previously described in U.S. Pat. No. 9,102,912. In this patent, the BHK21-C12 cell line is referred to as BHK/CMV/v1 #12 in Example 14 and FIG. 6. Briefly, the commonly used baby hamster kidney cell line BHK-21 was transfected with the plasmid pCMV-susCD163v1, which contains a truncated variant (v1) of the porcine (sus) CD163 PRRSV receptor gene, under control of the CMV promoter. The plasmid also contains a kanamycin/neomycin resistance gene under the control of dual prokaryotic/eukaryotic promoters for selection in *E. coli* and mammalian cells, respectively. Following transfection, the cells were subjected to simultaneous selection with G418 (Geneticin, a neomycin analog) and single cell cloning in 96-well plates. One of the resulting clones (#12, or "C12") was chosen for further use and designated BHK21-C12.

The BHK21-C12 cell line was serially passaged 65 times under G418 selection and retained the PRRSV-permissive phenotype. By passage 64 it was observed that a few cells survived infection with the PRRS virus, indicating the early stages of phenotypic instability. Additional single cell cloning was performed, and many new clones were evaluated for the PRRSV-permissive phenotype and for general growth characteristics. Of these, clone #26 was selected for being superior to other clones and to the parental BHK21-C12 cell line. Clone #26 was designated BHK21-C12-26, and was used in the attenuation of PRRS virus 96V198.

Example 2—Additional Cells Appropriate for Adaptation and Culturing of Virus that is Safe and Effective at Very Early Aqe, Such as for Vaccination at Day 1 after Birth PK-9 cells are a transgenic cell line derived by stably transfecting the PK0809 porcine kidney cell line with a plasmid encoding a deleted version of the porcine CD163 gene and the neomycin resistance gene. Details of the construction and characterization of the PK-9 cell line have been described previously (see U.S. Pat. No. 9,102,912).

It should be noted that adaptation of a first passage virus from PAM cells to growth on PK-9 cells may be difficult, and required several attempts with multiple parallel lineages. In this case, infection can be monitored by immunofluorescence of duplicate wells using FITC-conjugated monoclonal antibody SDOW17 specific for the viral nucleocapsid protein (Rural Technologies Inc, Brookings S. Dak.). Early passages may result in a few small foci, and not generate enough cell-free virus particles to initiate infection of a fresh monolayer. These passages can nonetheless be accomplished by treating the infected monolayer with Accutase (a trypsin substitute) and reseeding the cells in multiple wells with fresh medium, with or without the addition of non-infected PK-9 cells. After several such passages, some lineages should show a clear increase in the frequency and size of fluorescent foci. Some of these should acquire the ability to be passaged using cell-free virus fluids. Generally, it is expected that appropriate passages evidence a reduced ability to inhibit alpha interferon.

The safety and efficacy of the European PRRS vaccines of the invention are further evidenced by the experimental protocols and data comprising Examples 3-7, which follow directly.

Example 3—Duration of Immunity Provided by the European PRRS MLV Administered to 1-Day-Old Piglets with Subsequent Challenge with a Further European PRRSV Isolate at Approximately 26 Weeks Post-Vaccination The objective of the study was to evaluate the duration of immunity (DOI) of the European PRRS modified life vaccine (the virus encoded by SEQ ID NO:5) in pigs vaccinated at 1 day of age by the intramuscular (IM, group T02) or the intranasal (IN, group T03) route, followed by a respiratory challenge at 26 weeks post-vaccination with a different European PRRSV isolate. The primary variable in determining the efficacy was viral load in serum (viremia) of treatment groups T02 and T03 in comparison to T01 pigs. Lung lesions, rectal temperatures, shedding, clinical signs and body weight were compared as secondary variables.

At 1 day of age, pigs from groups T02 and T03 were administered with a single 2 mL dose of IVP via the intramuscular (T02) or the intranasal (T03) route. Pigs from the control group (T01) received 2 ml intramuscular and 2 ml intranasal of Saline Solution. At 26 weeks post-vaccination (182 days), pigs were challenged intranasally with the EU PRRSV isolate Olot/91 (see J. Duran et al., Virus Genes, vol 14 No. 1, 1997, pp 19-29 and Z. Lu et al., Virology Journal, vol 11, No 42, 2014) as a respiratory challenge.

During the challenge phase, blood samples, nasal and oral swabs, clinical observations and rectal temperatures were collected every 3-4 days until day of necropsy. Pigs were weighed before vaccination, before challenge, and at necropsy. Nine or ten days post-challenge, pigs were euthanized and necropsied. Upon necropsy, lungs were evaluated for the presence of PRRSV lesions and scored. The test was valid since all T01 pigs remained PRRSV viro-negative throughout the vaccination period and no confounding disease factors were detected.

Applicable; PAM, Porcine Alveolar Macrophages; PRRSV, Porcine Reproductive and Respiratory Syndrome Virus; PBS, Phosphate Buffered Saline; RT-qPCR, Quantitative Reverse-Transcription Polymerase Chain Reaction; SART, Sick Animal Report and Treatment; SOP, Standard Operating Procedure; S/P, Sample to positive; and TBD, To Be Determined.

Design

| Group | Treatment Description | Dosage (Actual titre) | Route | Day of Admin | Day of Challenge (DC) | Challenge dose (Actual titre) | End of Study (DN) | N |
|---|---|---|---|---|---|---|---|---|
| T01 | CP | 2 mL + 2 mL | IM + IN | D 0 | D 182 | 5.7 $log_{10}$ | D 191/D 192 | 20 |
| T02 | IVP | 2.2 $log_{10}$ $CCID_{50}$/2.0 mL | IM | D 0 | D 182 | $CCID_{50}$/pig | D 191/D 192 | 18 |
| T03 | IVP | 2.2 $log_{10}$ $CCID_{50}$/2.0 mL | IN | D 0 | D 182 | | D 191/D 192 | 17 |

A protective effect of both IM and IN vaccination was observed when comparing viral load in serum between groups. Both groups vaccinated with the IVP (T02 and T03) had significantly (P≤0.05) lower viral titers compared to the control group at all sampling days post-challenge (3, 6, 8 and 9/10, corresponding to study days 185, 188, 190 and 191/192). Efficacy was also supported by the significant reduction of PRRSV-associated lung lesions at necropsy, as well as the significant reduction in nasal and oral shedding in both vaccinated groups compared to the control group.

Comparison between vaccinated groups revealed that at 3 days post-challenge, the group vaccinated by the IN route (T03) had significantly lower viremia, nasal shedding and oral shedding compared to the group vaccinated by the IM route (T02). These results indicate that, under the conditions of the present study, the protection obtained following the IN vaccination was stronger than following IM vaccination.

Vaccination induced the development of PRRSV-specific antibodies within 28 days post-vaccination. All vaccinated pigs were seropositive to PRRS antibodies at challenge (26 weeks post-vaccination), indicating that both administration routes were able to elicit a strong and protective antibody response to vaccination. However, the level of antibody titres detected at challenge were significantly higher in the group vaccinated by the IN route compared to the group vaccinated intramuscularly, fact that would explain the significant reduction in viral load detected in both serum and excretion routes in the IN group compared to the IM group at 3 days post-challenge.

In conclusion, the results from the present study demonstrated that a single administration of the EU PRRSV MLV vaccine (SEQ ID NO:5) containing a dose of 2.5 log 10 CCID50 to 1 day-old pigs by the intramuscular or the intranasal route conferred a protective duration of immunity of 6.5 months (26 weeks).

Abbreviations used in Examples 3-7 include: AAALAC, Association for Assessment and Accreditation of Laboratory Animal Care; AE, Adverse Event; CCID50, Cell Culture Infectious Dose 50%; CP, Control Product; DC, Day of Challenge; DCF, Data Capture Form; DRAC, Daily Review Animal Care; ID, identification; IF, Immunofluorescence; IM, Intramuscular; IN, Intranasal; IV, Intravenous; IVP, Investigational Veterinary Product; MDA, Maternally Derived Antibodies; MLV, Modified Live Vaccine; MSF, Master Study File; MSV, Master Seed Virus; NA, Not At 1 day of age, a 2 mL dose (IM route) and a 2 mL dose (IN route) of the CP was administered to T01 piglets. Also, a single 2.0 mL dose of the IVP was administered to T02 piglets by IM route and to T03 piglets by IN route. Twenty-six weeks post-vaccination, pigs were challenged with PRRSV Olot/91 and at 9-10 post-challenge, they were euthanized and necropsied. Day 0=Day of vaccination.

Randomisation

Immediately after birth, piglets were cross-fostered such that piglets were randomized and spread as even as possible over all sows. At weaning, sows were removed and piglets were housed in pens in the source farm (1 pen per treatment). Certain parameters for the animals are as follows:

| | |
|---|---|
| Species/breed: | Porcine crossbred |
| Initial age on day 0: | 1 day (24 ± 12 h) old |
| Initial weight on day 0 | NA |
| Sex: | Male and female |
| Origin: | Farm Cal Marquès<br>Zoetis Manufacturing & Research Spain S.L.<br>Ctra Camprodon s/n Finca “La Riba”<br>17813 Vall de Bianya (Girona), Spain |
| Serological status: | Seronegative to PRRSV |
| Reproductive status: | NA |
| Identification method: | Ear tags |
| Ownership: | Zoetis Manufacturing & Research Spain S.L. |

Twelve pregnant sows were used to get a total of 117 piglets. The day before the expected farrowing date, parturition was induced with an intramuscular injection of cloprostenol (Cyclix® Porcino, Virbac). All sows farrowed the day after (D-1). To reduce the duration of parturition and the number of stillborn piglets, all sows but two (71 and 78 that already finished farrowing), were injected with oxytocin (Partovet® DFV).

During the vaccination phase, 8 piglets died or had to be euthanized. From the remaining 109 piglets, 55 were for the present study.

To reduce aggressive and sexual behaviour in male pigs at older age, piglets were castrated at 6 days of age following site-specific animal welfare procedures. Three piglets (232, 284 and 286) could not be castrated because they had scrotal hernia.

Around 1 month post-vaccination, two sudden deaths with identical pathological findings together with the presence of white spots on the floor and some pigs showing white urine at the end of the micturition process suggested a bacterial infection affecting the urinary tract. This process was not considered to have an impact on the study results since all animals responded well to treatment and no other case appeared during the rest of the vaccination phase (next 3 months until challenge). •Any animal with an injury or clinical illness unrelated to the test procedure that may affect the health of the animal and evaluation of the results may be withdrawn from the study at the discretion of the investigator. The Investigational Veterinary Product (IVP) was provided from a freeze dried fraction that was resuspended in saline solution at 2.5 $\log_{10}$ $CCID_{50}$/ML (SEQ ID NO: 5 virus)

Reconstitution

At day 0, the IVP was diluted with vaccine diluent (lot T22019) to match the target titer (2.5 $\log_{10}$ $CCID_{50}$/2 mL). One aliquot of the IVP was collected for titration on BHK-21-C12-26 cells to confirm the dosage. An additional IVP sample was frozen (−80±10° C.) and stored as a retention sample. Titration on BHK-21-C12-26 cells was performed following local standard procedures. The reconstituted and diluted vaccine had a titer of $10^{1.9}$ $CCID_{50}$/ml, which corresponds to $10^{2.2}$ $CCID_{50}$/2 mL (2.2 $\log_{10}$ $CCID_{50}$/2 ml). At day 0, the IVP was diluted with vaccine diluent (lot T22019) to match the target titer (2.5 $\log_{10}$ $CCID_{50}$/2 mL). One aliquot of the IVP was collected for titration on BHK-21-C12-26 cells to confirm the dosage. An additional IVP sample was frozen (−80+10° C.) and stored as a retention sample. Titration on BHK-21-C12-26 cells was performed following local standard procedures. The reconstituted and diluted vaccine had a titer of $10^{1.9}$ $CCID_{50}$/ml, which corresponds to $10^{2.2}$ $CCID_{50}$/2 mL (2.2 $\log_{10}$ $CCID_{50}$/2 ml), Control Product (CP) was vaccine diluent (saline solution) and was administered as 4.0 mL (2.0 mL IM+2.0 mL IN)

At day 0, piglets were vaccinated with the IVP or CP as described. Piglets of T01 and T02 groups were injected intramuscularly in the right side of the neck. Piglets of T01 and T03 groups were administered intranasally, delivering 1.0 mL in each nostril.

Challenge Administration

All pigs were challenged intranasal (IN) with a total challenge volume of 2.0 mL by instilling 1.0 mL of challenge material in each nostril with the Olot/91 virus at a titre of 105.7 CCID50/2 mL.

Results—Viremia

All pigs were RT-qPCR PRRSV negative in serum before vaccination (D0) and before challenge (D181). After challenge, 100% of pigs from the T01 group became viremic at day 185 (3 days post-challenge, DC+3) and remained positive until the end of the study. In the vaccinated groups, 100% (T02 group) and 88% (T03) of the pigs were also positive at DC+3. However, the percentage of positive pigs in both vaccinated groups decreased in time and became significantly lower at DC+8 and day of necropsy (DN) compared to the control group T01.

In both vaccinated groups, the amount of viral load detected in serum was also significantly reduced compared to group T01 at all sampling days post-challenge. At day 185 (DC+3), a significant reduction on viral titres was also observed in the group T03 in relation to T02. Table 1 summarizes the viremia results during the 10-day post-challenge period.

TABLE 1

Summary of viremia results by group and day of study (challenge phase data)

| | | | $Log_{10}$RNA copies/ml of serum | | | | | |
|---|---|---|---|---|---|---|---|---|
| Group | Study day | N | Least Square Means | SE | Range | Lower 95% CB | Upper 95% CB | % of viremic animals |
| T01 | D 181 (DC − 1) | 20 | 1.69 | 0.18 | 1.70 to 1.70 | 1.31 | 2.08 | 0.0 |
| T02 | D 181 (DC − 1) | 18 | 1.71 | 0.18 | 1.70 to 1.70 | 1.33 | 2.09 | 0.0 |
| T03 | D 181 (DC − 1) | 17 | 1.70 | 0.26 | 1.70 to 1.70 | 1.17 | 2.22 | 0.0 |
| T01 | D 185 (DC + 3) | 20 | 6.47 | 0.18 | 5.28 to 7.95 | 6.09 | 6.85 | 100.0 |
| T02 | D 185 (DC + 3) | 18 | 5.77 | 0.18 | 3.94 to 7.13 | 5.38 | 6.15 | 100.0 |
| T03 | D 185 (DC + 3) | 17 | 5.04 | 0.26 | 1.70 to 7.28 | 4.51 | 5.57 | 88.2 |
| T01 | D 188 (DC + 6) | 20 | 5.24 | 0.18 | 3.89 to 6.40 | 4.86 | 5.62 | 100.0 |
| T02 | D 188 (DC + 6) | 17 | 3.95 | 0.18 | 1.70 to 5.86 | 3.56 | 4.34 | 94.1 |
| T03 | D 188 (DC + 6) | 17 | 3.73 | 0.26 | 1.70 to 5.45 | 3.20 | 4.26 | 82.4 |
| T01 | D 190 (DC + 8) | 20 | 4.62 | 0.18 | 2.91 to 6.58 | 4.24 | 5.00 | 100.0 |
| T02 | D 190 (DC + 8) | 17 | 2.12 | 0.18 | 1.70 to 4.17 | 1.74 | 2.51 | 35.3 |
| T03 | D 190 (DC + 8) | 17 | 2.22 | 0.26 | 1.70 to 4.48 | 1.70 | 2.75 | 29.4 |
| T01 | D 191/192 (DN) | 20 | 5.90 | 0.18 | 4.51 to 7.35 | 5.52 | 6.28 | 100.0 |
| T02 | D 191/192 (DN) | 17 | 2.06 | 0.18 | 1.70 to 3.41 | 1.68 | 2.45 | 35.3 |
| T03 | D 191/192 (DN) | 17 | 1.99 | 0.26 | 1.70 to 2.95 | 1.46 | 2.51 | 29.4 |

N: number;
SE: Standard Error;
CB: confidence bound;
D = day of study;
DC: day of challenge;
DN: day of necropsy;
RT-qPCR positive: >1.7 log10 RNA copies/ml.

Nasal Shedding

All pigs were RT-qPCR PRRSV negative in nasal swabs before challenge (D181). After challenge, all pigs from T01 became nasal shedders. In the vaccinated groups, the percentage of pigs that ever shed by the nasal route was 94% (T02 group) and 88% (T03 group). In relation to the T01 group, a significant reduction in the percentage of nasal shedders was observed in the T03 group at days 185, 188 and 191/192 (DC+3, DC+6 and DN) and in the T02 group at day 191/192 (DN). No significant differences in the percentage of nasal shedders were detected between vaccinated groups. The amount of virus shed by the nasal route was significantly higher in the T01 group compared to the T02 group at DC+6 and DN, and compared to T03 at DC+3, DC+6 and DN. Comparison between vaccinated groups revealed significantly higher viral titres in the T02 group compared to the T03 at DC+3. Table 2 summarizes the nasal shedding results during the 10-day post-challenge period.

TABLE 2

Summary of nasal shedding results by group and day of study (post-challenge data)

| Group | Study day | N | Log$_{10}$RNA copies/ml<br>Least Square Means | SE | Range | Lower 95% CB | Upper 95% CB | % of nasal shedders |
|---|---|---|---|---|---|---|---|---|
| T01 | D 181 (DC − 1) | 20 | 1.70 | 0.19 | 1.70 to 1.70 | 1.32 | 2.08 | 0.0 |
| T02 | D 181 (DC − 1) | 18 | 1.68 | 0.20 | 1.70 to 1.70 | 1.28 | 2.08 | 0.0 |
| T03 | D 181 (DC − 1) | 16 | 1.69 | 0.21 | 1.70 to 1.70 | 1.27 | 2.11 | 0.0 |
| T01 | D 185 (DC + 3) | 20 | 4.61 | 0.19 | 3.70 to 5.51 | 4.23 | 4.99 | 100.0 |
| T02 | D 185 (DC + 3) | 18 | 4.66 | 0.20 | 1.70 to 6.49 | 4.26 | 5.06 | 88.9 |
| T03 | D 185 (DC + 3) | 17 | 3.35 | 0.21 | 1.70 to 5.44 | 2.94 | 3.75 | 70.6 |
| T01 | D 188 (DC + 6) | 20 | 4.36 | 0.19 | 3.44 to 5.25 | 3.98 | 4.75 | 100.0 |
| T02 | D 188 (DC + 6) | 17 | 3.33 | 0.21 | 1.70 to 5.21 | 2.92 | 3.74 | 94.1 |
| T03 | D 188 (DC + 6) | 17 | 3.02 | 0.21 | 1.70 to 5.22 | 2.62 | 3.43 | 76.5 |
| T01 | D 190 (DC + 8) | 20 | 2.21 | 0.19 | 1.70 to 3.69 | 1.83 | 2.59 | 40.0 |
| T02 | D 190 (DC + 8) | 17 | 2.39 | 0.21 | 1.70 to 4.73 | 1.98 | 2.80 | 35.3 |
| T03 | D 190 (DC + 8) | 17 | 2.21 | 0.21 | 1.70 to 3.92 | 1.80 | 2.61 | 35.3 |
| T01 | D 191/192 (DN) | 20 | 2.55 | 0.19 | 1.70 to 5.98 | 2.17 | 2.94 | 50.0 |
| T02 | D 191/192 (DN) | 17 | 1.81 | 0.21 | 1.70 to 3.25 | 1.40 | 2.22 | 11.8 |
| T03 | D 191/192 (DN) | 17 | 1.82 | 0.21 | 1.70 to 2.84 | 1.41 | 2.22 | 11.8 |

N: number;
SE: Standard Error;
CB: confidence bound;
D = day of study;
DC: day of challenge;
DN: day of necropsy;
RT-qPCR positive: >1.7 log10 RNA copies/ml Oral Shedding All pigs were RT-qPCR PRRSV negative in oral swabs before challenge (D181). After challenge, the proportion of pigs that ever shed by the oral route was 9/20 (45%), 8/18 (44%) and 7/17 (41%) in T01, T02 and T03 groups, respectively. By the end of the study, all pigs from the T02 group and all but one in the T03 group were negative in oral swabs. In the control group T01, 5/20 were still positive at that time; differences in the percentage of oral shedders between T01 and T02 were statistically significant at the end of study (DN). The amount of virus shed by the oral route was significantly higher in the T01 group compared to the T03 group at day of necropsy, corresponding to 9/10 days post-challenge. Viral load was also significantly higher in the T02 group compared to both T01 and T03 at day 185 (DC+3). Table 3 summarizes the oral shedding results during the 10-day post-challenge period.

TABLE 3

Summary of oral shedding results by group and day of study (post-challenge data)

| Group | Study day | N | Log$_{10}$RNA copies/ml<br>Least Square Means | SE | Range | Lower 95% CB | Upper 95% CB | % of oral shedders |
|---|---|---|---|---|---|---|---|---|
| T01 | D 181 (DC − 1) | 20 | 1.70 | 0.07 | 1.70 to 1.70 | 1.57 | 1.83 | 0.0 |
| T02 | D 181 (DC − 1) | 18 | 1.70 | 0.12 | 1.70 to 1.70 | 1.45 | 1.95 | 0.0 |
| T03 | D 181 (DC − 1) | 17 | 1.70 | 0.08 | 1.70 to 1.70 | 1.54 | 1.86 | 0.0 |
| T01 | D 185 (DC + 3) | 20 | 1.79 | 0.07 | 1.70 to 2.71 | 1.66 | 1.93 | 10.0 |
| T02 | D 185 (DC + 3) | 18 | 2.17 | 0.12 | 1.70 to 5.65 | 1.92 | 2.42 | 27.8 |
| T03 | D 185 (DC + 3) | 17 | 1.79 | 0.08 | 1.70 to 2.52 | 1.64 | 1.95 | 11.8 |
| T01 | D 188 (DC + 6) | 20 | 1.85 | 0.07 | 1.70 to 2.86 | 1.72 | 1.98 | 15.0 |
| T02 | D 188 (DC + 6) | 17 | 1.95 | 0.13 | 1.70 to 2.59 | 1.70 | 2.20 | 23.5 |
| T03 | D 188 (DC + 6) | 17 | 2.11 | 0.08 | 1.70 to 3.66 | 1.95 | 2.26 | 35.3 |
| T01 | D 190 (DC + 8) | 20 | 1.70 | 0.07 | 1.70 to 1.70 | 1.57 | 1.83 | 0.0 |
| T02 | D 190 (DC + 8) | 17 | 1.75 | 0.13 | 1.70 to 1.70 | 1.49 | 2.00 | 0.0 |
| T03 | D 190 (DC + 8) | 17 | 1.70 | 0.08 | 1.70 to 1.70 | 1.54 | 1.86 | 0.0 |
| T01 | D 191/192 (DN) | 20 | 1.95 | 0.07 | 1.70 to 3.16 | 1.81 | 2.08 | 25.0 |

TABLE 3-continued

Summary of oral shedding results by group and day of study (post-challenge data)

| | | | $Log_{10}$RNA copies/ml | | | | | | |
|---|---|---|---|---|---|---|---|---|
| Group | Study day | N | Least Square Means | SE | Range | Lower 95% CB | Upper 95% CB | % of oral shedders |
| T02 | D 191/192 (DN) | 17 | 1.73 | 0.13 | 1.70 to 1.70 | 1.48 | 1.99 | 0.0 |
| T03 | D 191/192 (DN) | 17 | 1.72 | 0.08 | 1.70 to 2.00 | 1.56 | 1.87 | 5.9 |

N: number;
SE: Standard Error;
CB: confidence bound;
D = day of study;
DC: day of challenge;
DN: day of necropsy;
RT-qPCR positive: >1.7 log10 RNA copies/ml Clinical Observations None of the pigs showed abnormal general condition, depression, respiratory distress, coughing or sneezing during the whole post-challenge period.

Rectal Temperatures

Table 4 summarizes the rectal temperature results during the post-challenge period. In the T01 group, 5/20 pigs (25%) had fever (RT≥40.5) at least once during the post-challenge period. In the vaccinated groups T02 and T03, the proportion of pigs that had fever after challenge was 8/18 (44%) and 12/17 (71%), respectively. Rectal temperatures were significantly higher in both vaccinated groups T02 and T03 compared to the T01 group, at day 185 (DC+3).

TABLE 4

Summary of rectal temperature results in piglets by group and day of study

| | | | Rectal temperatures (° C.) | | | | | |
|---|---|---|---|---|---|---|---|---|
| Group | Study Day | N | LSM | SE | Range | Lower 95% CB | Upper 95% CB | % of pigs with fever (RT ≥ 40.5) |
| T01 | D 182 (DC) | 20 | 39.5 | 0.09 | 39 to 40.32 | 39.3 | 39.7 | 0.0 |
| T02 | D 182 (DC) | 18 | 39.7 | 0.13 | 39 to 40.85 | 39.4 | 39.9 | 5.6 |
| T03 | D 182 (DC) | 17 | 39.7 | 0.12 | 38.94 to 40.43 | 39.4 | 39.9 | 0.0 |
| T01 | D 185 (DC + 3) | 20 | 39.9 | 0.09 | 39.06 to 40.82 | 39.7 | 40.1 | 5.0 |
| T02 | D 185 (DC + 3) | 18 | 40.3 | 0.13 | 39.39 to 41.54 | 40.1 | 40.6 | 33.3 |
| T03 | D 185 (DC + 3) | 17 | 40.4 | 0.12 | 39.3 to 41.14 | 40.1 | 40.6 | 52.9 |
| T01 | D 188 (DC + 6) | 20 | 40.0 | 0.09 | 39.14 to 40.8 | 39.8 | 40.1 | 25.0 |
| T02 | D 188 (DC + 6) | 17 | 40.1 | 0.14 | 39.14 to 41.02 | 39.9 | 40.4 | 29.4 |
| T03 | D 188 (DC + 6) | 17 | 40.2 | 0.12 | 39.36 to 41.38 | 39.9 | 40.4 | 29.4 |
| T01 | D 190 (DC + 8) | 20 | 39.5 | 0.09 | 38.9 to 40.26 | 39.3 | 39.7 | 0.0 |
| T02 | D 190 (DC + 8) | 17 | 39.7 | 0.14 | 39.02 to 40.75 | 39.4 | 39.9 | 5.9 |
| T03 | D 190 (DC + 8) | 17 | 39.6 | 0.12 | 39.07 to 40.86 | 39.4 | 39.9 | 17.6 |
| T01 | D 191 (DC + 9) | 20 | 39.5 | 0.09 | 38.85 to 39.95 | 39.3 | 39.7 | 0.0 |
| T02 | D 191 (DC + 9) | 17 | 39.7 | 0.14 | 39.02 to 40.2 | 39.4 | 40.0 | 0.0 |
| T03 | D 191 (DC + 9) | 17 | 39.7 | 0.12 | 38.9 to 41.15 | 39.5 | 40.0 | 5.9 |

LSM: Least Square Means;
SE: Standard Error;
CB: confidence bound;
RT: Rectal Temperature Lung Lesions The percentage of lung with lesions for each treatment group is shown in Table 5. Lung visual scores are displayed in Table 6. At necropsy, 18/20 pigs (90%) from the control group T01 had a positive lung visual score, indicating that PRRSV challenge was successful in inducing lung lesions. In the T02 and T03 groups, 12/17 (71%) and 7/16 (44%) pigs scored positive as well. One pig from the T03 group (#300) showed catharral-purulent pleuropneumonia affecting between 10 and 70% of the right lung lobes, between 2 and 30% of the left lung lobes and 70% of the accessory lobe, thus masking the presence of any potential PRRSV-associated lesions. The data from this pig was flagged from the analysis (see flagging report in the MSF). The percentage of lung with lesions observed at necropsy was significantly higher in the control group T01 compared to the vaccinated groups T02 and T03. No differences were detected between vaccinated groups.

TABLE 5

Summary of the percentage of lung with lesions

| Group | N | Back transformed LSM* | SE | Lower 95% CB | Upper 95% CB | Range |
|---|---|---|---|---|---|---|
| T01 | 20 | 3.7 [A] | 0.61 | 2.6 | 5.0 | 0.2 to 13.5 |
| T02 | 17 | 1.0 [B] | 0.35 | 0.5 | 1.9 | 0.0 to 4.4 |
| T03 | 16 | 0.7 [B] | 0.30 | 0.2 | 1.5 | 0.0 to 5.2 |

*Different letter supercripts indicate statistical significant difference.

TABLE 6

Lung visual score by treatment group

| | Visual score | | | | | | | | Total observations |
|---|---|---|---|---|---|---|---|---|---|
| | 0 (no lesions) | | 1 (mild lesions) | | 2 (moderate lesions) | | 3 (severe lesions) | | |
| Group | Number | % | Number | % | Number | % | Number | % | Number |
| T01 | 2 | 10.0 | 17 | 85.0 | 1 | 5.0 | 0 | 0.0 | 20 |
| T02 | 5 | 29.4 | 12 | 70.6 | 0 | 0.0 | 0 | 0.0 | 17 |
| T03 | 9 | 56.3 | 7 | 43.8 | 0 | 0.0 | 0 | 0.0 | 16 |

Serology (ELISA) Results

A summary of the serology results is shown in Table 7. The ELISA results obtained from samples collected at monthly intervals during the vaccination phase are only summarized with descriptive statistics (geometric mean and standard deviations); differences between groups could not be evaluated because there was no replication of the experimental unit (treatments were not comingled). Differences between groups were only tested at study day 181, after animal comingling for the challenge phase. All pigs were ELISA negative prior to vaccination (IDEXX S/P ratio<0.4). Pigs from the control group T01 remained negative until challenge. One month post-vaccination (Day 28), all pigs from T02 and T03 groups had already developed antibodies to PRRSV and all of them were still positive at challenge (6.5 months post-vaccination). Comparison between groups at day 181 (DC-1) revealed significantly higher least squares mean antibody titers in the T03 group compared to T02 group.

TABLE 7

Summary of S/P ratio ELISA results,

| Treatment Number | Day of Study | N | Geometric Mean/ LSM* | SD/SE | Range | % of seropositive |
|---|---|---|---|---|---|---|
| T01 | Day 0 | 20 | 0.023 | 0.002 | −0.019 to 0.239 | 0.0 |
| T02 | Day 0 | 18 | 0.006 | 0.000 | −0.015 to 0.140 | 0.0 |
| T03 | Day 0 | 17 | 0.001 | 0.000 | −0.018 to 0.100 | 0.0 |
| T01 | Day 28 | 20 | −0.013 | −0.000 | −0.025 to 0.018 | 0.0 |
| T02 | Day 28 | 18 | 2.487 | 0.174 | 2.112 to 2.923 | 100.0 |
| T03 | Day 28 | 17 | 2.496 | 0.218 | 2.022 to 3.037 | 100.0 |
| T01 | Day 56 | 20 | −0.010 | −0.001 | −0.079 to 0.182 | 0.0 |
| T02 | Day 56 | 18 | 2.366 | 0.832 | −0.078 to 3.591 | 94.4 |
| T03 | Day 56 | 17 | 2.523 | 0.317 | 1.656 to 3.452 | 100.0 |
| T01 | Day 83 | 20 | 0.011 | 0.000 | −0.013 to 0.080 | 0.0 |
| T02 | Day 83 | 18 | 2.249 | 0.328 | 1.556 to 2.852 | 100.0 |
| T03 | Day 83 | 17 | 2.281 | 0.322 | 1.582 to 3.162 | 100.0 |
| T01 | Day 113 | 20 | 0.042 | 0.001 | −0.003 to 0.091 | 0.0 |
| T02 | Day 113 | 18 | 1.598 | 0.333 | 0.692 to 2.606 | 100.0 |
| T03 | Day 113 | 17 | 1.797 | 0.360 | 0.956 to 2.938 | 100.0 |
| T01 | Day 140 | 20 | 0.023 | 0.001 | −0.005 to 0.118 | 0.0 |

TABLE 7-continued

Summary of S/P ratio ELISA results,

| Treatment Number | Day of Study | N | Geometric Mean/ LSM* | SD/SE | Range | % of seropositive |
|---|---|---|---|---|---|---|
| T02 | Day 140 | 18 | 1.270 | 0.249 | 0.612 to 2.076 | 100.0 |
| T03 | Day 140 | 17 | 1.461 | 0.316 | 0.526 to 2.534 | 100.0 |
| T01 | Day 168 | 20 | 0.034 | 0.001 | −0.002 to 0.122 | 0.0 |
| T02 | Day 168 | 18 | 1.433 | 0.329 | 0.709 to 2.780 | 100.0 |
| T03 | Day 168 | 17 | 1.674 | 0.427 | 0.677 to 3.175 | 100.0 |
| T01 | Day 181 | 20 | 0.055 | 0.001 | 0.006 to 0.200 | 0.0 |
| T02 | Day 181 | 18 | 1.190 | 0.060 | 0.477 to 1.959 | 100.0 |
| T03 | Day 181 | 17 | 1.527 | 0.068 | 0.665 to 2.422 | 100.0 |

*Results from days 0, 28, 56, 83, 113, 140 and 168 are expressed with the Geometric Mean and standard deviation (SD). Day 181 with the Back transformed - Least Square Mean (LSM) and standard error (SE);; ELISA positive: S/P ratio ≥ 0.4

Viremia and Shedding

Prior to statistical analysis the RT-qPCR was transformed using an appropriate logarithm transformation. The transformed data was analyzed using a general linear repeated measured mixed model. Pairwise treatment comparisons were made at each time point if the treatment or treatment by time point interaction effect was significant (P≤0.05). Treatment least squares mean and 95% confidence intervals were back transformed for presentation. Percentage of animals viremic/shedders was also calculated. Each sample was determined to be positive if >50 PRRSV RNA copies/mL (1.7 log 10 PRRSV RNA copies/mL), which corresponds to a half of the detection limit of the technique (100 PRRSV RNA copies/mL). It was also determined if an animal was ever viremic or ever shed for Days ≤DC (reference to pre challenge) and Days >DC (post challenge). Frequency tables for viremia status were calculated for each time point and if the animal was ever viremic for days prior to challenge and days post challenge.

Rectal Temperatures

Rectal temperatures were analyzed using a general linear repeated measures mixed model analysis. Pairwise treatment comparisons were made at each time point if the treatment or treatment by time point interaction effect was significant (P≤0.05). Treatment least squares means, 95% confidence intervals, the minimum and maximum were calculated for each time point. Descriptive statistics, means, standard deviations, and ranges, were calculated for each treatment and day of study, pre-challenge. Frequency distributions of animals with a fever (rectal temperature □40.5° C.) were calculated for each treatment and time point data is collected. It was determined if an animal ever had fever for Days ≤DC and for Days >DC. Frequency tables for if an animal ever had a fever were calculated for each period, Days ≤DC and Days >DC.

Serology (ELISA)

Prior to statistical analysis the serology was transformed, where necessary, using an appropriate logarithm transformation. The transformed serology data was analyzed using a general linear repeated measured mixed model. Pairwise treatment comparisons were made at each time point if the treatment or treatment by time point interaction effect was significant (P□0.05). Treatment least squares means and 95% confidence intervals were back transformed for presentation. in addition, frequency distributions of the positive/negative results were calculated for each treatment at each time point. Also, it was determined for each animal whether or not it seroconverted (≥0.4 S/P ratio) at any time during the study. Frequency distributions of whether or not an animal seroconverted were calculated for each treatment. Descriptive statistics, means, standard deviations, and ranges, were calculated for each treatment, pre-challenge.

Clinical Observations

Frequency distributions of clinical signs prior to challenge and clinical signs following challenge were calculated, separately, for each treatment and time point data was collected. Frequency distributions of whether an animal ever had a clinical sign, for each phase (Days ≤DC and Days >DC), was calculated for each treatment.

Body Weights

Body weights were analyzed using a general linear repeated measures mixed model. Least squares means, standard errors, 95% confidence intervals, minimums and maximums were calculated for each treatment at each time point. Pairwise treatment comparisons were made between treatments at each time point if the treatment effect and/or the treatment by time-point interaction was significant. The standard errors and 95% confidence intervals of the estimates were calculated. Descriptive statistics, means, standard deviations, and ranges were calculated for each treatment, pre-challenge. Average daily gain estimates and comparisons were calculated using parameter estimates from the model.

Lung Lesions

Percentage of total lung with lesions was calculated using the following formula: Percentage of total lung with lesions=(0.10×left cranial)+(0.10×left middle)+(0.25×left caudal)+(0.10×right cranial)+(0.10×right middle)+(0.25×right caudal)+(0.10×accessory). The arcsine square root transformation was applied to the percentage of total lung with lesions prior to analysis. The transformed lung lesions was analyzed with a general linear mixed model. Pairwise comparisons were made between treatment groups if the treatment effect was significant. Back transformed least squares means of percentage of total lung with lesions, their standard errors, and their 95% confidence intervals were calculated as well as the minimums and maximums.

Lung Lesion Assessment Score

Frequency distributions of lung lesion assessment scores were calculated for each treatment. The scores, normal or not normal, were analyzed using a generalized linear mixed model for binomial data. If the general linear mixed model did not converge, Fisher's Exact test was used to analyze the data. If the treatment main effect was significant, then pairwise treatment comparisons was made.

Models for Analyses

Transformed percentage of total lung with lesions was analyzed with a general linear mixed model with fixed effects, treatment, and random effects pen and block within pen. Linear combinations of the parameter estimates were used in a priori contrasts after testing for a significant (P≤0.05) treatment effect. Comparisons were made between treatments. The 5% level of significance (P≤0.05) was used to assess statistical differences. Least squares means (back-transformed), standard errors, 95% confidence intervals of the means and ranges were calculated for each treatment.

Viremia status was analyzed with a general linear repeated measures mixed model with a logit link with fixed effects: treatment, time point, and treatment by time point interaction, and random effects: pen, block within pen, and animal within block, pen, and treatment, which is the animal term. Linear combinations of the parameter estimates were used in a priori contrasts after testing for a significant (P≤0.05) treatment effect or treatment by time point interaction. Comparisons were made between treatments at each time point. The 5% level of significance (P≤0.05) was used to assess statistical differences. Least squares means (back transformed), standard errors, and 95% confidence intervals of the means were calculated for each treatment and time point. if the model did not converge, Fisher's Exact were used for the analysis.

Lung assessment scores, normal/not normal, and if ever viremic were analyzed with a generalized linear mixed model with fixed effects treatment, and random effects pen and block within pen, via GLIMMIX. If the treatment main effect was significant, then pairwise treatment comparisons were made. If GLIMMIX did not converge, Fisher's Exact test was used for analysis.

Viral load, serology, body weight, and rectal temperature were analyzed with a generalized linear repeated measures mixed model with fixed effects: treatment, time point, and treatment by time point interaction, and random effects: pen, block within pen, and animal within block, pen, and treatment, which is the animal term. Linear combinations of the parameter estimates were used in a priori contrasts after testing for a significant (P≤0.05) treatment effect or treatment by time point interaction. Comparisons were made between treatments at each time point. The 5% level of significance (P≤0.05) was used to assess statistical differences. Least squares means (back transformed for viral load and serology), standard errors, 95% confidence intervals of the means and ranges were calculated for each treatment and time point. All hypothesis tests were conducted at the 0.05 level of significance using two-sided tests.

Discussion

The objective of the present study was thus to evaluate the Duration of Immunity (DOI) of the EU PRRS modified live vaccine (SEQ ID NO:5) in pigs vaccinated at 1 day of age by the intramuscular (IM, group T02) or the intranasal (IN, group T03) route, upon inoculation with a genotype I PRRS isolate as a respiratory challenge at 26 weeks post-vaccination. The primary variable in determining the efficacy was viral load in serum (viremia) of treatment groups T02 and T03 in comparison to T01 pigs. Lung lesions, rectal temperatures, shedding, clinical signs and body weight were compared as secondary variables.

The test was valid since all T01 pigs remained PRRSV viro-negative throughout the vaccination period and no confounding disease factors were detected. A protective effect of both IM and IN vaccination was observed when comparing viral load in serum between groups; the control group T01 had significantly higher viral titers compared to the vaccinated groups T02 and T03 at all sampling days post-challenge. In addition, in relation to the control group, the proportion of viremic pigs was also significantly reduced at days 8 and 9/10 post-challenge in both vaccinated groups. When vaccinated groups were compared, significantly lower viral titers were detected at day 185 (DC+3) in the group vaccinated by the IN route (T03) compared to the group vaccinated intramuscularly (T02). The benefit of both IM and IN vaccination on virus replication was also supported by the significant reduction observed in both vaccinated groups in the amount of virus shed by the nasal route as well as in the percentage of nasal shedders. In addition, a positive effect of vaccination was also observed on oral shedding at 9/10 days post-challenge, as demonstrated by the significant reduction in viral load (T03 group) or the percentage of positive pigs in oral swabs (T02 group) in relation to the control group.

After challenge, rectal temperatures were significantly higher in both vaccinated groups compared to the control group at DC+3. At that time, the proportion of pigs with fever (RT≥40.5° C.) in the groups vaccinated with the IVP by the IM and the IN route was 6/18 (33%) and 9/17 (53%), respectively. In the control group, only 1/20 (5%) had fever at DC+3. However, it is noteworthy to mention that at that time (DC+3), the viral load detected in serum was indeed significantly reduced in both vaccinated groups compared to the control group, thus suggesting that PRRSV replication was probably not the sole reason behind the elevated rectal temperatures observed in vaccinated pigs shortly after challenge. In addition, from then onwards, rectal temperatures from vaccinated pigs decreased and, by day 8 post-challenge, mean rectal temperatures in all groups were already below 40-C.

Besides elevated rectal temperatures, none of the pigs from any group showed clinical signs compatible with PRRSV (abnormal body condition, depression, respiratory distress, coughing or sneezing) during the whole post-challenge period. In addition, no differences in body weight or average daily weight gain were detected between groups.

At necropsy, 18/20 pigs (90%) from the control group T01 had a positive lung visual score, indicating that PRRSV challenge was successful in inducing lung lesions. In the T02 and T03 groups, 12/17 (71%) and 7/16 (44%) pigs scored positive as well. Comparison between treatment groups showed significant higher % of lung with lesions in the control group than in the vaccinated groups, demonstrating the benefit of vaccination on reducing the PRRSV-associated lung lesions regardless of the administration route.

Serology data demonstrated that vaccination with the IVP by either the IM or the IN route induced the development of PRRSV-specific antibodies within 28 days post-vaccination. All vaccinated pigs were seropositive to PRRSV antibodies at challenge (6.5 months post-vaccination), indicating that both administration routes were able to elicit a strong and protective antibody response to vaccination. However, comparison between vaccinated groups showed significantly higher antibody titers in the group vaccinated by the IN route compared to the group vaccinated by the IM route.

Although vaccination by both the IN and the IM routes conferred a clear protection against PRRSV challenge at 26 weeks post-vaccination, comparison between groups revealed that at 3 days post-challenge, the group vaccinated by the IN route (T03) had significantly lower viremia, nasal shedding and oral shedding compared to the group vaccinated intramuscularly (T02). These results indicate that, under the conditions of the present study, the protection obtained following the IN vaccination was stronger than following IM vaccination. These differences in the virological outcome would be explained by the significantly higher antibody titres detected by ELISA before challenge in the group vaccinated IN (S/P ratio range: 0.665-2.422), compared to the group vaccinated IM (S/P ratios range: 0.477-1.959).

Vaccination with a single administration of the EU PRRS MLV vaccine (SEQ ID NO:5) containing a dose of 2.5 log 10 CCID50 to 1 day-old seronegative pigs by either the IM or the IN route conferred a duration of immunity of 26 weeks, as seen by the significant reduction on the viral load detected in serum after challenge with a pathogenic EU PRRSV strain at 26 weeks post-vaccination. Efficacy was also supported by the significant reduction on the percentage of lung lesions at necropsy, as well as the reduction of nasal and oral shedding.

Laboratory Methods

In regard of RT qPCR, viremia (PRRSV load in serum) and shedding (PRRSV load in swab material) were measured by means of a Reverse Transcription (RT) qPCR performed following local SOP on the serum samples collected before vaccination (D-1), before challenge (D62) and at 3, 5, 7 and 10 days post-challenge (D66, D68, D70 and D73). In brief, the purified viral RNA was used as template, reverse transcribed at 50° C. for 30 minutes, and denatured at 95° C. for 5 minutes. The PCR program of reactions consisted of 40 cycles of denaturation at 95° C. for 20 seconds and annealing at 53° C. for 40 seconds. The qRT-PCR was conducted in a 7500 Real-Time PCR System thermalcycler. Appropriate primers and probe were selected for Lelystad virus as follows:

```
Forward primer (Lelystad F):
5'-GCACCACCTCACCCAGAC-3' (SEQ ID NO: 6, final
concentration 0.5 micromolar).

Reverse primer (Lelystad R):
5'-CAGTTCCTGCGCCTTGAT-3' (SEQ ID NO:7, final
concentration 0.5 micromolar).

Probe (Lelystad S):
5'-6-FAM-CCTCTGCTTGCAATCGATCCAGAC-TAMRA-3' (SEQ
ID NO: 8, final concentration 0.6 micromolar).
```

SeroloGy (ELISA)

Sera collected before vaccination (D0), before challenge (D67) and at necropsy (D77) were tested for antibodies to PRRSV using the IDEXX PRRS X3 ELISA, following the manufacturer's instructions. In brief, serum samples were diluted 1:40 in 96-well plate coated with a recombinant PRRSV antigen and incubated 30 minutes at 18-26° C. After washing, an anti-porcine horseradish peroxidase conjugate was added and plates were incubated for another 30 minutes at 18-26° C. Unbound conjugate was washed away and TMB substrate was added to the wells. Color development was measured at 650 nm. S/P values were recorded for each sample. If the S/P ratio was ≥0.4 the sample was classified as positive for PRRS antibodies. If the S/P ratio was <0.4 the sample was classified as negative. ELISA instructions are included in the study file.

Example 4—Onset of Immunity (OOI) of a Modified Live EU PRRSV Vaccine Administered to 2 Weeks Old piGs Against Challenge with an European PRRS Isolate at 4 Weeks Post-Vaccination The objective of this study was to evaluate the Onset of Immunity (001) of an experimental EU PRRSV MLV vaccine (the SEQ ID NO:5 virus) administered to 2-week old pigs for the prevention of respiratory disease induced by PRRSV at 4 weeks post-vaccination. The primary variable in determining prevention of disease was viral load in serum in treatment group T02 (vaccinated with the Test Item) compared to T01 (vaccinated with control product), supported by lung lesions, oral and nasal shedding, clinical observations, rectal temperatures and body weight.

At the age of 14-15 days, a single 2.0 mL dose of the Control Product (CP) or the Test Item (TI, SEQ ID NO:5 virus) was administered as an intramuscular injection to each animal. Four weeks post-vaccination, pigs were challenged intranasally with the EU PRRSV isolate Olot/91 as a respiratory challenge. During the challenge phase, blood samples, nasal and oral swabs, clinical observations and rectal temperatures were collected every 2-3 days until day of necropsy. Pigs were weighed the day before vaccination, before challenge and at necropsy. Ten days post-challenge, pigs were anesthetized, euthanized and necropsied. Upon necropsy, lungs were evaluated for the presence of PRRSV lesions and scored. This study was valid since T01 pigs remained PRRSV sero and viro-negative throughout the vaccination period and no confounding disease factors were detected.

A protective effect of vaccination was observed when comparing viral load in serum between groups. The group vaccinated with the TI (T02) had significantly lower viral titers compared to the control group at all sampling days post-challenge.

Efficacy was also supported by the significant reduction of the percentage of lung with lesions at necropsy (10 days post-challenge), the reduction on nasal and oral shedding, as well as by the reduction on rectal temperatures at 7 days post-challenge. No differences were detected in body weight. Vaccination induced the development of PRRSV-specific antibodies within 4 weeks post-vaccination. Ten days after challenge, antibody titers remain significantly higher in the T02 group compared to the control one (T01). In conclusion, a single intramuscular administration of the experimental EU PRRSV MLV vaccine containing a dose of 2.0 $\log_{10}$ $CCID_{50}$ to 14-15 day-old pigs (seronegative to PRRSV) was protective against respiratory disease induced after challenge with a pathogenic EU PRRS strain at 4 weeks post-vaccination. Experimental Design is as follows:

| | VACCINATION (Day 0) | | CHALLENGE (Day 27) | | |
|---|---|---|---|---|---|
| Group | Test material | Dose | Test material | Dose | N |
| T01 | Control product | 2 mL | PRRSV Olot/91 | 5.4 $\log_{10}$ $CCID_{50}$/2 mL | 20 |
| T02 | Test Item | 2.0 $\log_{10}$ $CCID_{50}$/2 mL | PRRSV Olot/91 | 5.4 $\log_{10}$ $CCID_{50}$/2 mL | 20 |

At Day 27, after re-housing of the pigs, all animals were challenged with 2 ml of the challenge strain Olot/91, by intranasal (IN) route. The pigs were challenged with a total challenge volume of 2.0 mL by instilling 1.0 mL challenge material in each nostril. Pigs were held in a head up position for some seconds after challenge.

Clinical Observations and Rectal Temperatures

Clinical observations included general condition, depression, sneezing, coughing and respiratory distress. Rectal temperatures were collected according to local standard procedures. Those days (before and after vaccination/challenge inoculation) in which a complete clinical examination was not performed, the general health of the pigs was observed and recorded in Daily Review Animal Care (DRAC) forms following standard SOP.

Necropsy and Lung Scoring.

Upon necropsy, lung lesions were scored using the following methods: 1) the percentage of consolidation for each lobe (left cranial, left middle, left caudal, right cranial, right middle, right caudal and accessory) will be scored and recorded as percent of lobe observed with lesions; and 2) a numeric visual score (0, 1, 2, 3).

RT qPCR

Viremia (PRRSV load in serum) and shedding (PRRSV load in nasal and oral swabs) were measured by means of a Reverse Transcription (RT) qPCR performed following standard procedures. In brief, the purified viral RNA was used as template, reverse transcribed at 50-C for 30 minutes, and denatured at 95° C. for 5 minutes. The PCR program of reactions consisted of 40 cycles of denaturation at 95° C. for 20 seconds and annealing at 53° C. for 40 seconds. The qRT-PCR was conducted in a 7500 Real-Time PCR System thermalcycler. Results were expressed as RNA copies/ml.

Serology

Sera collected before vaccination, before challenge and at necropsy were tested for antibodies to PRRSV using the IDEXX PRRS X3 ELISA, following the manufacturer's instructions. In brief, serum samples were diluted 1:40 in 96-well plate coated with a recombinant PRRSV antigen and incubated 30 minutes at 18-26° C. After washing, an anti-porcine horseradish peroxidase conjugate was added and plates were incubated for another 30 minutes at 18-26° C. Unbound conjugate was washed away and TMB substrate was added to the wells. Color development was measured at 650 nm. S/P values were recorded for each sample. If the S/P ratio was ≥0.4 the sample was classified as positive for PRRS antibodies. If the S/P ratio was <0.4 the sample was classified as negative. ELISA instructions are included in the study file. The study ended at day 37 (euthanasia).

Viremia and Shedding

Prior to statistical analysis the RT-qPCR data was transformed using an appropriate logarithm transformation. The transformed data was analyzed using a general linear repeated measured mixed model. Pairwise treatment comparisons were made at each time point if the treatment or treatment by time point interaction effect is significant (P≤0.05). Treatment least squares mean and 95% confidence intervals were back transformed for presentation. Percentage of days viremic/shedding was also calculated. Each sample was determined to be positive if >250 PRRSV RNA copies/mL, which corresponded to a half of the detection limit of the technique (500 PRRSV RNA copies/mL of sample). It was also determined if an animal was ever viremic or ever shed for Days 527 (reference to pre challenge) and Days >27 (post challenge).

Lung Lesions

Percentage of total lung with lesions was calculated using the following formula: Percentage of total lung with lesions=(0.10×left cranial)+(0.10×left middle)+(0.25×left caudal)+(0.10×right cranial)+(0.10×right middle)+(0.25×right caudal)+(0.10×accessory). The arcsine square root transformation was applied to the percentage of total lung with lesions prior to analysis. The transformed lung lesions were analyzed with a general linear mixed model. Pairwise comparisons were made between treatment groups if the treatment effect was significant. Back transformed least squares means of percentage of total lung with lesions, their standard errors, and their 95% confidence intervals were calculated as well as the minimums and maximums. Frequency distributions of lung lesion assessment scores were calculated for each treatment. The scores, normal or not normal, were analyzed using a general linear mixed linear model for binomial data. If the general linear mixed model did not converge, Fisher's Exact test was used to analyze the data. If the treatment main effect was significant, then pairwise treatment comparisons was made.

Lung Scoring

The percentage of lung with lesions for each treatment group is shown in Table 8. Lung visual scores are displayed in Table 9. At necropsy, 17/18 pigs (94.4%) from the control group T01 had a positive lung visual score indicating that PRRSV challenge was successful in inducing lung lesions. In the T02 group, 14/19 (73.7%) pigs scored positive as well. Control group T01 had a significantly higher LS mean percentage of lung with lesions compared to the T02 group.

Regarding the total lung visual score, lungs from all T02 pigs were scored as either 0 (no lesions) or 1 (mild lesions). In the T01 control group, 7/18 (38.9%) pigs were given a visual score of 2 (moderate lesions). None of the lungs from any group was given a visual score of 3 (severe lesions).

TABLE 8

Summary of the percentage of lung with lesions

| | N | Back transformed LS Mean | Standard Error | Lower 95% CL | Upper 95% CL | Range |
|---|---|---|---|---|---|---|
| T01 | 18 | $7^a$ | 2 | 4 | 11 | 0 to 29 |
| T02 | 19 | $2^b$ | 1 | 1 | 5 | 0 to 10 |

Different superscripts mean significant differences among groups.

RT-qPCR Results, Viremia (PRRSV Load in Serum)

TABLE 9

Lung visual score by treatment group

| Treat- | Visual score | | | | | | Total obser- |
|---|---|---|---|---|---|---|---|
| | 0 (no lesions) | | 1 (mild lesions) | | 2 (moderate lesions) | | vations |
| ment | Number | % | Number | % | Number | % | Number |
| T01 | 1 | 5.6 | 10 | 55.6 | 7 | 38.9 | 18 |
| T02 | 4 | 26.3 | 14 | 73.7 | 0 | 0.0 | 19 |

All pigs were found RT-qPCR PRRSV negative in blood at day 0. At challenge (day 27), PRRSV RNA could be detected in 100% of the pigs vaccinated with the TI (T02 group). By that time, all T01 pigs where still PRRSV negative. In control pigs, viremia was first detected at day 29 (2 days post-challenge) and pigs remained PRRSV positive until the end of the study. At all sampling days post-challenge, viral loads detected in control T01 group were significantly higher than those detected in the T02 group. Table 10 summarize the viremia results from day 27 (day of challenge) until day 36. Summary of Least square means and LS Means differences between groups are shown in Table 11.

TABLE 10

Summary of viremia results by group and day of study.

| | | $Log_{10}$RNA copies/ml of serum | | | | | |
|---|---|---|---|---|---|---|---|
| | Day of Study | Least Squares Mean | Standard Error | Range | Lower 95% Confidence Bound | Upper 95% Confidence Bound | % of viremic pigs |
| T01 | Day 27 | 2.4 | 0.16 | 2.4 to 2.4 | 2.0 | 2.8 | 0.0% |
| T02 | Day 27 | 6.0 | 0.16 | 4.6 to 7.8 | 5.6 | 6.4 | 100.0% |
| T01 | Day 29 | 7.4 | 0.25 | 5.3 to 9.4 | 6.8 | 7.9 | 100.0% |
| T02 | Day 29 | 5.6 | 0.25 | 3.8 to 7.8 | 5.1 | 6.1 | 100.0% |
| T01 | Day 31 | 8.1 | 0.27 | 6.3 to 9.2 | 7.5 | 8.6 | 100.0% |
| T02 | Day 31 | 6.9 | 0.27 | 4 to 8.9 | 6.4 | 7.5 | 100.0% |
| T01 | Day 34 | 7.3 | 0.24 | 5.4 to 8.4 | 6.8 | 7.8 | 100.0% |
| T02 | Day 34 | 6.4 | 0.24 | 4.2 to 8 | 5.9 | 6.9 | 100.0% |
| T01 | Day 36 | 7.2 | 0.28 | 5.7 to 8.6 | 6.6 | 7.7 | 100.0% |
| T02 | Day 36 | 5.6 | 0.28 | 2.7 to 8.4 | 5.0 | 6.2 | 100.0% |

RT-qPCR positive: >2.4 log10 RNA copies/ml

TABLE 11

Summary table of Least Square Means for viremia results.

| Treatment | Least Square Mean at different study dates | | | | |
|---|---|---|---|---|---|
| Number | Day 27 | Day 29 | Day 31 | Day 34 | Day 36 |
| T01 | $2.4^a$ | $7.4^a$ | $8.1^a$ | $7.3^a$ | $7.2^a$ |
| T02 | $6.0^b$ | $5.6^b$ | $6.9^b$ | $6.4^b$ | $5.6^b$ |

Different superscripts mean significant differences among groups.

Nasal and Oral Shedding

All pigs were found RT-qPCR PRRSV negative in nasal and orals swabs at day 0. At challenge (day 27), 70% and 85% of pigs vaccinated with the TI (T02 group) had detectable PRRSV RNA in nasal and oral swabs, respectively. None of the pigs from the T01 group shed at that time. During the post-challenge period, the percentage of nasal shedders in the T01 group ranged from 85% (Day 34) to 100% (Day 29). In the T02 group, percentages of nasal shedders ranged from 42% (Day 36) to 90% (Day 29). Regarding oral shedding, the percentage of positive pigs ranged between 95 to 100% in the T01 group and between 73.7 to 100% in group T02. Comparison of LSM between groups revealed significant higher viral loads in T01 group at all days post-challenge but day 34 for nasal swabs and at days 31 and 36 for oral swabs.

Results on nasal and oral shedding from day 27 (day of challenge) until day 36 are summarized in Table 12 and Table 14, respectively. Summary of LSM and LS Means differences between groups are shown in Tables 13 and 15.

TABLE 12

Summary of nasal shedding results by group and day of study.

| | Day of Study | Least Squares Mean (RNA copies/ml (per swab)) | Standard Error | Range | Lower 95% Confidence Bound | Upper 95% Confidence Bound | % of shedding pigs |
|---|---|---|---|---|---|---|---|
| T01 | Day 27 | 2.4 | 0.19 | 2.4 to 2.4 | 2.0 | 2.8 | 0.0% |
| T02 | Day 27 | 3.5 | 0.26 | 2.4 to 4.9 | 3.0 | 4.1 | 70.0% |
| T01 | Day 29 | 6.5 | 0.19 | 5.4 to 7.6 | 6.1 | 6.9 | 100.0% |
| T02 | Day 29 | 4.8 | 0.26 | 2.4 to 6.8 | 4.2 | 5.3 | 90.0% |
| T01 | Day 31 | 6.4 | 0.19 | 5.2 to 7.7 | 6.0 | 6.8 | 100.0% |
| T02 | Day 31 | 5.0 | 0.27 | 2.4 to 6.8 | 4.5 | 5.5 | 94.7% |
| T01 | Day 34 | 4.5 | 0.19 | 2.4 to 6.9 | 4.1 | 4.9 | 85.0% |
| T02 | Day 34 | 4.2 | 0.27 | 2.4 to 7.2 | 3.7 | 4.8 | 84.2% |
| T01 | Day 36 | 4.7 | 0.20 | 2.4 to 6.5 | 4.3 | 5.1 | 88.9% |
| T02 | Day 36 | 3.3 | 0.27 | 2.4 to 5.6 | 2.8 | 3.9 | 42.1% |

RT-qPCR positive: >2.4 log10 RNA copies/ml

TABLE 13

Summary table of Least Square Means for nasal shedding results.

| Treatment Number | Day 27 | Day 29 | Day 31 | Day 34 | Day 36 |
|---|---|---|---|---|---|
| | Least Square Mean at different study dates | | | | |
| T01 | 2.4 [a] | 6.5 [a] | 6.4 [a] | 4.5 [a] | 4.7 [a] |
| T02 | 3.5 [b] | 4.8 [b] | 5.0 [b] | 4.2 [a] | 3.3 [b] |

TABLE 14

Summary of oral shedding results by group and day of study.

| | Day of Study | Least Squares Mean (RNA copies/ml (per swab)) | Standard Error | Range | Lower 95% Confidence Bound | Upper 95% Confidence Bound | % of shedding pigs |
|---|---|---|---|---|---|---|---|
| T01 | Day 27 | 2.4 | 0.19 | 2.4 to 2.4 | 2.0 | 2.8 | 0.0% |
| T02 | Day 27 | 4.9 | 0.26 | 2.4 to 7.4 | 4.3 | 5.4 | 85.0% |
| T01 | Day 29 | 4.2 | 0.19 | 2.4 to 5.9 | 3.8 | 4.6 | 95.0% |
| T02 | Day 29 | 4.0 | 0.26 | 2.4 to 5.2 | 3.5 | 4.6 | 90.0% |
| T01 | Day 31 | 5.2 | 0.19 | 4 to 6.9 | 4.8 | 5.6 | 100.0% |
| T02 | Day 31 | 4.4 | 0.26 | 2.4 to 6.6 | 3.8 | 4.9 | 94.7% |
| T01 | Day 34 | 4.9 | 0.19 | 3.7 to 6.7 | 4.5 | 5.3 | 100.0% |
| T02 | Day 34 | 4.6 | 0.26 | 3 to 5.8 | 4.1 | 5.1 | 100.0% |
| T01 | Day 36 | 4.6 | 0.20 | 3.5 to 6.1 | 4.2 | 5.0 | 100.0% |
| T02 | Day 36 | 3.8 | 0.26 | 2.4 to 5.2 | 3.3 | 4.4 | 73.7% |

RT-qPCR positive: >2.4 log10 RNA copies/ml

TABLE 15

Summary table of Least Square Means for oral shedding results.

| Treatment Number | Day 27 | Day 29 | Day 31 | Day 34 | Day 36 |
|---|---|---|---|---|---|
| | Least Square Mean at different study dates | | | | |
| T01 | 2.4 [a] | 4.2 [a] | 5.2 [a] | 4.9 [a] | 4.6 [a] |
| T02 | 4.9 [b] | 4.0 [a] | 4.4 [b] | 4.6 [a] | 3.8 [b] |

Different superscripts mean significant differences among groups.

Serology

All pigs were serologically negative for PRRSV prior to vaccination (IDEXX S/P ratio<0.4). At challenge (4 weeks post-vaccination), all control pigs were still seronegative, while 90% of the pigs vaccinated with the TI had seroconverted to PRRSV (IDEXX S/P ratio>0.4). At day 36 (9 days post challenge), all pigs were seropositive to PRRSV. Pigs from group T02 had significantly higher LS mean antibody titres compared to the control group T01. Table 6 summarizes the serology results obtained by ELISA.

TABLE 16

S/P ratio ELISA results (LS mean and range) and % of seropositive pigs by treatment group and day

| Treatment | Day 27 LS Mean (range) | Day 27 % sero-positive | Day 36 LS Mean (range) | Day 36 % sero-positive |
|---|---|---|---|---|
| T01 | 0.011 [a] (−0.087 to 0.123) | 0.0% | 1.582 [a] (0.846 to 2.357) | 100% |
| T02 | 1.617 [b] (0.31 to 2.561) | 90% | 1.960 [b] (0.762 to 2.884) | 100% |

Different superscripts mean significant differences among groups.

Discussion

This study evaluated the Onset of Immunity (001) of a modified live PRRSV vaccine in pigs vaccinated at 14-15 days of age upon inoculation with a pathogenic genotype I PRRSV isolate as a respiratory challenge at 4 weeks after vaccination. The test was valid since all T01 pigs remained PRRSV sero and viro-negative throughout the vaccination period and no confounding disease factors were detected.

The primary variable in determining the efficacy was viral load in serum of treatment group T02 in comparison to T01 pigs. Lung lesions, rectal temperatures, shedding, clinical signs and body weight were compared as secondary variables.

A protective effect of vaccination was observed when comparing viral load in serum between T01 and T02 groups; the group vaccinated with the TI had significantly lower viral titers compared to the control group T01 at all sampling days post-challenge.

After challenge, oral and nasal shedding could be detected in all pigs regardless of the treatment group. However, significant higher viral loads were detected in the T01 group, at all days but day 34 for nasal swabs and at days 31 and 36 for oral swabs.

Regarding lung lesions, a protective vaccine effect was also observed for the T02 pigs when comparing back-transformed least squares mean percentage of lung lesions between groups. In addition, all 14 T02 pigs that were given a positive visual score at necropsy were scored as 1 (mild lesions). In contrast, lungs from the 17 pigs in T01 group that also scored positive, 10 were given a score of 1 (mild lesions) and 7 a score of 2 (moderate lesions).

During the post-challenge period, rectal temperatures were significantly lower in pigs vaccinated with the TI at day 7 post-challenge. By that time, 20% of the T01 pigs had fever, whereas none in the T02 group did. Before challenge, rectal temperatures in the T02 group were also significant lower compared to T01. However, none of the pigs had fever and there was no apparent clinical condition in that group that might have induced an increase in rectal temperature. Besides increased rectal temperatures, no other clinical observations compatible with PRRS (depression, respiratory distress, coughing or sneezing) were observed in any pig during the whole time-period. In addition, no differences in body weight could be detected at any time point between groups.

Serology data demonstrated that vaccination with the TI (T02 group) induced the development of PRRSV-specific antibodies within 4 weeks post-vaccination. Antibody titers in the T02 group increased until the end of the study and were significantly higher than titers detected by that time in the non-vaccinated challenged group T01.

Vaccination with a single intramuscular administration of the experimental EU PRRSV MLV vaccine containing a dose of 2.0 $\log_{10}$ $CCID_{50}$ to 14-15 day-old pigs was protective against PRRSV, as seen by the significant reduction on the viral load detected in serum after challenge with a pathogenic EU PRRS strain at 4 weeks post-vaccination. Efficacy was also supported by the protective effect observed on the percentage of lung lesions at necropsy (10 days post-challenge), reduction on oral and nasal shedding as well as reduction on rectal temperatures at 7 days post-challenge Example 5—Assessment of the Potential Effect of Maternally-Derived Antibodies on the Efficacy of the Modified Live EU PRRSV Vaccine Administered to 1-Day-Old Seropositive Pigs Against Challenge with a European PRRSV Isolate The objective of the present study was to evaluate the influence of maternally derived antibodies (MDA) on the efficacy of the EU PRRS MLV (the virus expressed from SEQ ID NO:5), when administered in 1 day-old piglets by the intramuscular (IM, group T02) or the intranasal (IN, group T03) route.

The study was designed based on the recommendations of the EMA/CVMP/WP/439467/2007: "Reflection paper on the demonstration of a possible impact of maternally derived antibodies on vaccine efficacy in young animals" and the European Pharmacopoeia (Ph. Eur.) Monograph 04/2008: 50207: "Evaluation of efficacy of veterinary vaccines and immunosera". Both documents recommend that the influence of passively acquired and maternally derived antibodies on the efficacy of a vaccine has to be adequately evaluated. In addition, EMA/CVMP/WP/439467/2007 states that the efficacy of the vaccine in animals vaccinated in the presence of MDAs should be, notwithstanding normal biological variation, similar to that obtained in animals of the same age but vaccinated in the absence of MDAs.

Based on the abovementioned specifications, the onset of protective Immunity (001) of the modified live EU PRRSV vaccine was evaluated in seropositive pigs vaccinated (IM and IN routes) at 1 day of age upon inoculation with a pathogenic genotype I PRRSV isolate as a respiratory challenge. The animals were challenged at the time when the levels of MDAs detected by seroneutralization test (SNT) in the control group (T01) became undetectable. To demonstrate protection against challenge, the same parameters evaluated in a previous study performed in seronegative animals were evaluated (viral load in serum, lung lesions, rectal temperatures, shedding, clinical signs and body weight).

The test was valid since all control pigs (T01 group) remained PRRSV viro-negative throughout the vaccination period and no confounding disease factors were detected.

When the EU PRRS MLV was administered by the IM route, a protective effect of vaccination was observed as seen by a significant reduction of viral load in serum compared to the control group; efficacy was also supported by the significant reduction of nasal and oral shedding as well as significant reduction in rectal temperatures. Differences in mean percentage of lung lesions were close to significance ($p=0.092$). The efficacy observed following the IM administration in the present study is similar to that obtained in a previous study, in which the efficacy was evaluated in seronegative animals; in both studies, a significant impact of vaccination was observed on the primary variable (reduction on viremia) and also supported by a reduction on nasal shedding and rectal temperatures.

When the EU PRRS MLV was administered by the IN route, no protection was achieved against PRRSV challenge, as seen by the lack of significant differences in any of the parameters evaluated.

In conclusion, the results of the present study demonstrate lack of interference of maternally derived antibodies with vaccine efficacy, when the vaccine is administered intramuscularly in 1 day old piglets. However, when the vaccine is administered by the IN route, an immune response was not generated in most pigs following vaccination, presumably due to neutralization of the vaccine by MDA. To produce PRRSV MDA positive piglets, six pregnant sows were vaccinated with the EU PRRS MLV vaccine lot VMRD13-015 (5 $\log_{10}$ $CCID_{50}$/2 mL) during the first half of gestation (45 days of pregnancy). The day before the expected farrowing date, parturition was induced with an intramuscular injection of cloprostenol (Cyclix® Porcino, Virbac). All sows farrowed the next day. All sows were seropositive to PRRS at day 0. Results are shown Vaccine virus was provided at a potency of 6.0 log 10CCID50/ml. At day 0, the IVP was diluted with vaccine diluent (lot T22019) to match the target titer (2.5 log 10 CCID50/2 mL). One aliquot of the IVP was collected for titration on BHK-21-C12-26 cells to confirm the dosage. An additional IVP sample was frozen (−80+10° C.) and stored as a retention sample. Titration on BHK-21-C12-26 cells was performed following local standard procedures. The reconstituted and diluted vaccine had a titer of 101.8 CCID50/ml, which corresponds to 102.1 CCID50/2 mL (2.1 log 10CCID50/2 ml)

At day 0, piglets were vaccinated with the IVP or CP as described in section 4. Piglets of T01 and T02 groups were injected intramuscularly in the right side of the neck. Piglets of T01 and T03 groups were administered intranasally, delivering 1.0 mL in each nostril. The challenge material was the genotype 1 Spanish PRRSV isolate Olot/91, grown in Porcine Alveolar Macrophages (PAM). This strain was isolated in 1991 from a case of late-term abortion in sows.

Viremia

All pigs were found RT-qPCR PRRSV negative in serum before vaccination (D0) and all pigs from the T01 group remained so until challenge. In contrast, 8/16 (50%) piglets from the T02 group (IM vaccinated) and 1/19 (5.3%) piglets from T03 group (IN vaccination) were RT-qPCR PRRSV positive at challenge (67 days post-vaccination).

After challenge, 100% of pigs from the T01 group became viremic at D70 (3 days post-challenge) and remained positive until the end of the study (DC+10). In the vaccinated groups (T02 and T03), all pigs were detected PRRSV positive at least once; however, by the end of the study (DC+10), only 11/16 T02 pigs (68.8%) were still viremic. In contrast, all T03 pigs but one were positive at all sampling points post-challenge.

Pigs from the T02 group had significantly lower viral load in serum than pigs from the T01 control group at all sampling days post-challenge. At DC+3 and DC+10, viral load in T02 group was also significantly lower than in the T03 group. No significant differences were detected between T01 and T03 groups.

Table 17 summarizes the viremia results during the 10-day post-challenge period.

TABLE 17

Summary of viremia results by group and day of study (post-challenge data)

| Group | Study day | N | $Log_{10}$RNA copies/ml of serum: Least Square Means | SE | Range | Lower 95% CB | Upper 95% CB | % of viremic animals |
|---|---|---|---|---|---|---|---|---|
| T01 | D 67 (DC) | 18 | 1.65 | 0.20 | 1.70 to 1.70 | 1.24 | 2.05 | 0.0 |
| T02 | D 67 (DC) | 16 | 2.25 | 0.36 | 1.70 to 3.84 | 1.53 | 2.97 | 50.0 |
| T03 | D 67 (DC) | 19 | 1.82 | 0.29 | 1.70 to 3.80 | 1.25 | 2.40 | 5.3 |
| T01 | D 70 (DC + 3) | 18 | 6.60 | 0.20 | 5.23 to 7.66 | 6.20 | 7.01 | 100.0 |
| T02 | D 70 (DC + 3) | 16 | 2.87 | 0.36 | 1.70 to 6.59 | 2.15 | 3.59 | 50.0 |
| T03 | D 70 (DC + 3) | 19 | 6.30 | 0.29 | 1.70 to 8.10 | 5.72 | 6.87 | 94.7 |
| T01 | D 73 (DC + 6) | 18 | 6.39 | 0.20 | 4.87 to 7.44 | 5.99 | 6.80 | 100.0 |
| T02 | D 73 (DC + 6) | 16 | 5.18 | 0.36 | 1.70 to 7.00 | 4.45 | 5.90 | 93.8 |
| T03 | D 73 (DC + 6) | 19 | 5.80 | 0.29 | 1.70 to 7.70 | 5.22 | 6.37 | 94.7 |
| T01 | D 75 (DC + 8) | 18 | 5.32 | 0.20 | 3.32 to 7.21 | 4.92 | 5.73 | 100.0 |
| T02 | D 75 (DC + 8) | 16 | 4.18 | 0.36 | 2.25 to 6.22 | 3.46 | 4.90 | 100.0 |
| T03 | D 75 (DC + 8) | 19 | 5.07 | 0.29 | 1.70 to 7.13 | 4.50 | 5.65 | 94.7 |
| T01 | D 77 (DC + 10) | 18 | 5.29 | 0.20 | 3.51 to 6.47 | 4.89 | 5.70 | 100.0 |
| T02 | D 77 (DC + 10) | 16 | 2.96 | 0.36 | 1.70 to 5.86 | 2.23 | 3.68 | 68.8 |
| T03 | D 77 (DC + 10) | 19 | 5.42 | 0.29 | 2.16 to 7.08 | 4.85 | 6.00 | 100.0 |

N: number;
SE: Standard Error;
CB: confidence bound;
D = day of study;
DC: day of challenge;
RT-qPCR positive: >1.7 log10 RNA copies/ml Viremia and Shedding Prior to statistical analysis the RT-qPCR data was transformed using an appropriate logarithm transformation. The transformed data was analyzed using a general linear repeated measured mixed model. Pairwise treatment comparisons was made at each time point if the treatment or treatment by time point interaction effect was significant (P≤0.05). Treatment least squares mean and 95% confidence intervals were back-transformed for presentation. Percentage of days viremic/shedding was also be calculated. Each sample was determined to be positive if >50 PRRSV RNA copies/mL, which corresponds to a half of the detection limit of the technique (100 PRRSV RNA copies/mL). It was also determined if an animal was ever viremic or ever shed for Days ≤DC (reference to pre-challenge) and Days >DC (post-challenge).

The objective of the present study was to evaluate the influence of maternally derived antibodies (MDA) on the efficacy of the EU PRRS MLV, when administered in 1 day-old piglets by the intramuscular (IM, group T02) or the intranasal (IN, group T03) route. The efficacy was evaluated in seropositive pigs vaccinated at 1 day of age upon inoculation with a pathogenic genotype I PRRSV isolate as a respiratory challenge. The animals were challenged at the time when the levels of MDAs detected by SNT in the T01 group became undetectable (Day 67).

The primary variable in determining the efficacy was viral load in serum (viremia) of treatment groups T02 and T03 in comparison to T01 pigs. Lung lesions, rectal temperatures, shedding, clinical signs and body weight were compared as secondary variables.

The test was valid since all T01 pigs remained PRRSV viro-negative throughout the vaccination period and no confounding disease factors were detected.

A protective effect of IM vaccination was observed when comparing viral load in serum between T01 and T02 groups; the group vaccinated with the IVP by the IM route had significantly lower viral titers compared to the control group T01 at all sampling days post-challenge. No differences in viral titers were detected between T01 and T03 groups, indicating no protective effect of IN vaccination on viral load post-challenge. The lack of efficacy in T03 group was also evidenced by the significant higher viral load observed in this group compared to the T02 group at 3 and 10 days post-challenge.

The protection conferred following IM vaccination (T02 group) was supported by the significant reduction in the percentage of nasal shedders as well as in the amount of virus detected in nasal and oral secretions in the T02 group in relation to the control group T01. Similar to what was observed for viremia, no positive effect of vaccination was observed in virus shedding when the IVP was administered by the IN route (T03 group), since no differences were detected between T01 and T03 groups. In fact, the amount of virus shed by both the nasal and oral route detected in the T03 group was also significantly higher than in the T02.

Vaccination by the IM route had also a positive impact on rectal temperatures. Before challenge (D67), mean rectal temperatures were significantly lower in T02 group compared to T01 and T03; however, since none of the pigs from any group had fever (RT≥40.5) at that time and rectal temperatures at D67 were collected before comingling the animals for the challenge phase, it can be concluded that these differences are probably attributed to stress of the animals that were first evaluated. During the post-challenge period, the percentage of pigs that had fever at least once was 61%, 31%, and 42% in T01, T02 and T03 groups, respectively. Control pigs (T01) had significantly higher rectal temperatures than pigs vaccinated with the IVP (T02 and T03 groups) at day 70 (3 post-challenge); however, at DC+10, rectal temperatures of T03 group were significantly higher than T01 and T02 groups. Besides increased rectal temperatures, no other clinical signs compatible with a PRRSV infection were observed. Regarding body weight, no effect of vaccination was observed as seen by the lack of significant differences between groups.

At necropsy, 13/18 pigs (72%) from the control group T01 had a positive lung visual score. In the T02 and T03 groups, 7/16 (44%) and 13/19 (68%) pigs scored positive as well. Comparison between treatment groups showed no significant differences in the % of lung with lesions. However, the differences observed between the control group T01 and the group vaccinated with the IVP by the IM route (T02) were close to significance (p=0.092).

All pigs had presence of PRRSV-specific antibodies before vaccination as measured by ELISA (S/P ratio≥0.4), thus complying with the inclusion criteria. Before challenge (67 days post-vaccination), 39% of the pigs in the control group were still seropositive, indicating the presence of remaining MDAs at that time (mean S/P ratio: 0.279). However, the fact that all pigs from the control group developed viremia after challenge and that 13/18 had also a positive lung score at necropsy indicates that the remaining MDA detected by ELISA did not interfere with the challenge take. In fact, when the levels of PRRSV-specific neutralizing antibodies were determined in those pigs by means of an SNT, negative results were detected in all T01 pigs before challenge (Day 52). In the group vaccinated with IVP by the IM route, 9/16 pigs experienced an increase in the levels of antibodies detected by ELISA from the day of vaccination to 67 days post-vaccination and all of them were seropositive before challenge (mean S/P ratio: 1.803), indicating the development of an antibody response following the IM vaccination even in the face of MDAs. In contrast, only 2/19 pigs vaccinated with the IVP by the IN route had an increase of PRRS antibodies from vaccination to challenge, and only 32% were seropositive at D67 (mean S/P ratio: 0.328), which indicates that no humoral immune response was induced in the other 17 pigs due to neutralization of the vaccine by MDA. After challenge (D77), all pigs, regardless of the treatment group, were seropositive and no significant differences in ELISA titers were detected between groups.

The EMA/CVMP/WP/439467/2007 guideline "Reflection paper on the demonstration of a possible impact of maternally derived antibodies on vaccine efficacy in young animals" states that the efficacy of a vaccine in animals vaccinated in the presence of MDAs should be, notwithstanding normal biological variation, similar to that obtained in animals of the same age but vaccinated in the absence of MDAs. Based on those specifications, efficacy observed in the present study should be similar to that obtained in a previous study (C/394/13), in which the OOI was evaluated in seronegative animals vaccinated at 1 day of age by the IN and IM routes.

When the EU PRRS MLV was administered by the IM route, efficacy could be demonstrated regardless of the serological status of the pigs, since a significant reduction on viremia (primary variable) was observed in both studies. The protective effect of IM vaccination was also demonstrated for nasal shedding and rectal temperatures in both cases. In addition, following IM vaccination of MDA+ pigs, oral shedding was also significantly reduced and differences in the % of lung with lesions were close to significant. Altogether, these data clearly demonstrate lack of interference of MDA with vaccine efficacy, when the vaccine is administered in 1 day old piglets by the IM route.

When the EU PRRS MLV was administered by the IN route, efficacy could only be demonstrated in the absence of MDA, as seen by the significant reduction in viremia and nasal shedding observed in seronegative animals. In MDA+ pigs, IN vaccination did not induce protection as seen by the lack of significant differences in any of the parameters evaluated.

Thus, vaccination with a single administration of the EU PRRSV MLV vaccine containing a dose of 2.5 $\log_{10}$ $CCID_{50}$ to 1 day-old seropositive pigs by the IM route was protective against PRRSV, as seen by the significant reduction of the viral load detected in serum after challenge with a pathogenic EU PRRS strain 67 days (9.6 weeks) post-vaccination. Efficacy was also supported by the significant reduction of nasal and oral shedding as well as rectal temperatures post-challenge. In addition, differences in mean percentage of lung lesions were close to significance (p=0.09). Vaccination with a single administration of the EU PRRSV MLV vaccine containing a dose of 2.5 $\log_{10}$ $CCID_{50}$ to 1 day-old seropositive pigs by the IN route was not protective against PRRSV challenge. The results of the present study demonstrate lack of interference of maternally derived antibodies with vaccine efficacy, when the vaccine is administered intramuscularly in 1 day old. When the vaccine is administered by the IN route, the majority of the pigs (17/19) failed to generate an immune response following vaccination as measured by ELISA. This indicates neutralization of the vaccine by MDA, which might compromise vaccine efficacy at the herd level.

Example 6—Dissemination, Spread and Safety of the Administration of One Dose, Repeated Dose and Overdose of the Modified Live EU PRRSV Vaccine 96V198 Clone 1 MSV+3 to 1 Day Old Pigs The objective of this study was to evaluate the safety of a repeated dose and an overdose, and the dissemination, spread and safety of one dose, of the modified live PRRSV vaccine 96V198 clone 1 administered at 1 day old pigs by IM and IN route. The test was carried out using the MSV+3, which is the least attenuated passage level (see Page 8, MSV+5 is standard Passage 49) that is present in a batch of vaccine.

According to the European legislation in force, it is compulsory to demonstrate the safety of a vaccine to get the marketing authorization. In this case, the protocol was developed taking account European Pharmacopoeia; directive 2009/9/EC and VICH GL44 guidelines to demonstrate the safety of one dose, repeated dose and overdose by IN and IM routes in 1 day old piglets—the proposed routes and category of animals for which the vaccine is intended.

Safety was evaluated in accordance with the European Pharmacopoeia recommendations for vaccines of veterinary use, i.e.: assessment of rectal temperature, and local and general reactions at least until 14 days after inoculation. The spreading of the vaccine strain was evaluated from vaccinated (one dose) to unvaccinated sentinel pigs; shedding (nasal mucus, oral fluids and faeces) and dissemination in tissues in vaccinated animals (one dose) was also investigated.

The study was carried out following the Good Laboratory Practice (GLP) regulations, in accordance with the corresponding OCDE Guidelines and in compliance with the requirements of European Pharmacopoeia 7.7 04/2013: 50206 (Evaluation of safety of veterinary vaccines and immunosera).

The test product was EU PRRS MLV (96V198 clone 1), least attenuated passage level MSV+3), at a maximum release titer of 105.2 TCID50/2 ml with a 2 L IN or IM dose, with the lower passage (less attenuated) being chosen as a better measure of safety. For a test system, the protocol was developed taking account European Pharmacopoeia; directive 2009/9/EC and VICH GL44 guidelines to demonstrate the safety of one dose, repeated dose and overdose by IN and IM routes in 1 day old piglets—the proposed category of animals for which the vaccine is intended.

Sufficient number of sows (n=11) were used to obtain the piglets needed to carry out the study (at least, n=80). The design applied allowing an appropriate description of the safety, dissemination and shedding of the vaccine for both routes, IM and IN. Sows arrived to the experimental farm from a PRRSV negative farm (Annex I). Sows were located in 11 isolated boxes in facilities. At the experimental farm, sows were bled before parturition and analyzed again for the presence of PRRSV-specific antibodies using a commercially ELISA (PRRS X3 Ab Test: Ref. 99-4095, IDEXX Laboratories;) (Annex I). IM administration of Ceftiofur sodium (13 ml/sow; to sows was done as a preventive treatment.

Farrowing of the sows was synchronized administrating 1 ml IM of D-Cloprostenol (Galapan, INVESA) (Annex XVI) approximately 111-113 days after insemination (with synchronization of parturitions). Piglets were born within the next 40 hours ($9^{th}$ and $10^{th}$, April). Start of vaccination was done at $10^{th}$; at this date, the age of all piglets was approximately ≤24 h (1 day of age).

Cross-fostering was performed within the first day post-farrowing (before vaccination) to balance litters and to homogenise the litters. Eventually, ten sows with a total number of piglets in each group equal or higher than the minimum sample size to carry out safety studies established in the European Pharmacopoeia were used. Total number: 80 piglets; 40 piglets for each route: IN and IM (28 vaccinated with the experimental product—dose, repeated dose and overdose-, 8 animals as controls, and 4 as sentinels).

Thirty extra-piglets were also distributed in all groups from T01 to T12 as reserve, to be included in the study only if some group did not reach the minimum number of piglets needed, due to piglet dead or exclusion (Annex II and Annex XIV; Amendment n° 2); raw data of those piglets were recorded in raw data extra-notebooks marked with an (S) (notebooks from number 13 to 24). Eventually, ten sows were used and each of them maintained eleven piglets.

Experimental Hypothesis

This study was designed to demonstrate the safety of the vaccine EU PRRS MLV in 1-day-old pigs (96V198 clone 1) under experimental conditions by comparison with a control group inoculated with the vaccine diluent (negative controls) for all parameters described below, but the temperature was analyzed taking into account the basal temperature of each piglet before vaccination as control value. The vaccine was considered safe if no severe local or systemic reactions were observed of causes attributable to the vaccine and the average temperature increase for all pigs in the vaccinated group did not exceed 1.5° C. compared to the basal average temperature before vaccination and no piglets in the experimental group showed a temperature rise greater than 2° C. in comparison with each piglet basal temperature before vaccination Spread and dissemination of the vaccine strain was evaluated investigating the presence of the vaccine strain in sentinel pigs. Dissemination in vaccinated animals was evaluated investigating the quantity of the virus in blood, nasal, oral and rectal samples and in tissues.

Rectal Temperatures—Intranasal and Intramuscular Routes.

Regarding temperatures, it can be concluded that the vaccine is safe in all the protocols evaluated (route, titer and number of doses) because the results obtained accomplish the European Pharmacopoeia recommendations for vaccines of veterinary use.

Local Reactions

Intranasal route.

No local reactions were observed.

Intramuscular Route.

At necropsy, only two piglets in T12 (maximum titer by IM route) had macroscopic mild lesions. Microscopically, lesions were only observed in four pigs from group T10; lesions were characterized by a very mild focal or multifocal presence of mononuclear inflammatory cell infiltrates.

Systemic Reactions and Adverse Events

Intranasal Route:

The absence of systemic reactions and clinical signs related to vaccination point out that the vaccine is safe.

Intramuscular Route.

Adverse events after the vaccine administration were observed only in 2 out of 8 piglets belonging to the group receiving the highest titer (×10 maximum release titer) by IM route (group T12). These events disappeared before 4 hours and piglets completely recovered. Regarding the clinical daily evaluation, the cases of lameness cannot be considered as phenomena related to the vaccine administration; lameness was observed also in piglets from control groups. The cause beyond the solely death observed during the study was due to crushing; therefore, it should be considered that this death was not related to the vaccine administration. In summary, the vaccine strain 96V198 CLONE 1 by IM route should be considered as completely safe with the exception of the adverse events described for the highest titer (×10).

Body Weight

Intranasal Route.

When means of weight gain were compared, T07 showed lower values than the corresponding control (T02) ($p<0.05$) from day 0 to 14. However, this difference disappeared when weight gains were compared from day 14 to 28 and, especially, when all the study—from day 0 to 28—was taken into account. Therefore, the weight gain of piglets vaccinated by intranasal route was not affected, independently of the dose received.

Intramuscular Route.

In the same way, T11 showed lower values than the corresponding control (T04) ($p<0.05$) from day 0 to 14. This difference disappeared when period from 14 to 28 was analyzed but it appeared again taken all the study—from day 0 to 28—. These differences could be explained because weight gain in three piglets from T11 were the lowest ones including all the piglets necropsied at day 28, independently of the product, titer or route of administration (it means T02, T04, T07 and T11). All the individual weight gains from day 0 to 28 were equal or higher than 5.5 kg, except for the three abovementioned piglets (weight gains 4.08, 2.89 and 3.05 kg for no 199, 202 and 205 piglets, respectively). Interestingly, these piglets suffered lameness for the longest period. In conclusion, it cannot be discriminated if the differences observed between T04 and T11 weight gains were due to the lameness events or to the vaccination.

Dissemination Intranasal and Intramuscular Routes.

Dissemination of the virus was demonstrated by the presence of vaccine strain in almost all the tissues evaluated in vaccinated animals, independently of the route used. The presence of the strain 96V198 CLONE 1 at titers that could be considered as high in lungs, tonsils and tracheobronchial lymph nodes but also in spleen and mesenteric lymph nodes suggest a complete organic dissemination of the vaccine strain.

Spread

Intranasal and Intramuscular Routes.

Although the detection of vaccine strain in oral fluid and rectal swabs were inconstant from vaccinated piglets, it was constant and high in nasal swabs; the frequency distribution of vaccine strain detection decreased along time. These results together with detection of vaccine strain in blood samples from all sentinel pigs, demonstrate that 96V198 CLONE 1 was actively and continuously shed early after vaccination. Also, presence of the vaccine strain in tissues and blood samples from sentinel piglets pointed out that the virus spread from vaccinated piglets was active; it could infect sentinel animals and it could replicate in them; and even one IM sentinel pig from T09 had lung lesions compatible with PRRS plus a positive result for IHC. In conclusion, the abovementioned results indicate that 96V198 CLONE 1 could be consistently transmitted from vaccinated to non-vaccinated piglets, at least during the early period after vaccination.

Lung Lesions Intranasal and Intramuscular Routes.

All nine pigs with macro and microscopic lesions compatible with PRRS (interstitial pneumonia) plus a positive result for PRRSV IHC were from IM groups. Thus, it can be concluded that IN route was safe, whereas IM route could induce lung lesions compatible with PRRSV at least in one pig of each group (from T09 to T12).

Example 7—Safety of the Repeated Administration of a Single Dose of a Modified Live EU PRRSv Vaccine when Administered to PRRSv Seropositive Pregnant Sows The present study was designed to demonstrate the safety of the administration of a repeated single dose of a EU PRRS MLV in seropositive sows at second half of pregnancy (87 days of gestation). No systemic reactions post-vaccination were observed following the first or second administration. In addition, no clinical observations were recorded in any sow throughout the whole observation period.

Regarding rectal temperatures, none of the sows showed fever at any point after vaccination (RT≥40.1° C.). In addition, the mean rectal temperature post-vaccination did not exceed the mean rectal temperature before vaccination plus 1.5° C. and none of the sows exceeded its own rectal temperature before vaccination plus 2° C.

Local reactions at the injection point were observed in 63% and 50% of the sows vaccinated with the test item at $1^{st}$ and $2^{nd}$ administration, respectively. Reactions consisted of palpable and/or visible swelling (from 0.4 to 2.8 cm of diameter) which disappeared between 1 to 6 days. None of the sows showed reddening, increase in local heat or pain at the injection point following any administration.

Regarding the reproductive performance, no abortions or premature farrowings were recorded. In addition, no apparent effect of vaccination was observed on the number stillborns, mummies, low viable piglets and pre-weaning mortality. Vaccination did not induce transplacental infection as seen by the RT-qPCR negative results detected in serum samples collected at birth and at weaning from the piglets. In conclusion, the repeated administration of the vaccine is safe in seropositive sows in the second half of pregnancy.

Abbreviation used herein include: BHK-21, baby Hamster Kidney clone 21; BRP, Batch Release Protocol; CCID50; Cell Culture Infectious Dose 50%; CP, Control Product; D, Day; DRAC, Daily Review Animal Care; ID, Identification; GLP, Good Laboratory Practices; IF, Immunofluorescence; IV, Intravenous; MLV, Modified Live Vaccine; MSV, Master Seed Virus; NA, Not applicable; P, Passage; PBS, phosphate Buffered Saline; PI, Post-inoculation; PRRSV, Porcine Reproductive and Respiratory Syndrome Virus; RT, Rectal Temperatures; RT-qPCR, Quantitative Reverse-Transcription Polymerase Chain Reaction; SOP, Standard Operating Procedure; S/P, Sample to positive; TBD, To Be Determined; TI, Test Item, and VICH, Veterinary International Conference on Harmonization.

Study Objective and Justification

EU PRRSV modified live vaccine (MLV) is intended for active immunization of gilts and sows in a PRRS contaminated environment, to reduce viremia, transplacental infection and abortion caused by infection with European strains of PRRS virus. According to the legislation in force, it is compulsory to demonstrate the safety of a vaccine to get the marketing authorization. This study was designed in accordance to European Pharmacopoeia 7.7:04/2013/50206—Evaluation of safety of veterinary vaccines and immunosera- and VICH GL44—Target animal safety for veterinary live and inactivated vaccines—guidelines. The objective of this study is to evaluate the safety of the repeated administration (1×+1×) of the EU PRRS MLV in seropositive sows at second half of pregnancy. Material tested was 6.6 log 10CCID50/vial of EU PRRSV, strain 96v198c1, (MSV+3), with a dose of 5.2 log 10CCID50 in 2 mL/Intramuscular.RT qPCR Viremia (PRRSV load in serum) was measured by means of a Reverse Transcription (RT) qPCR performed following standard procedures. In brief, the purified viral RNA was used as template, reverse transcribed at 50° C. for 30 minutes, and denatured at 95° C. for 5 minutes. The PCR program of reactions consisted of 40 cycles of denaturation at 95° C. for 20 seconds and annealing at 53° C. for 40 seconds. The qRT-PCR was conducted in a 7500 Real-Time PCR System thermalcycler.

The sequences of primers and probe are the following (SEQ ID NOS 6-8, consecutively):

```
Forward primer (Lelystad F):
5'-GCACCACCTCACCCAGAC-3' (Final concentration
0.5 μM).

Reverse primer (Lelystad R):
5'-CAGTTCCTGCGCCTTGAT-3' (Final concentration
0.5 μM).

Probe (Lelystad S):
5'-6-FAM-CCTCTGCTTGCAATCGATCCAGAC-TAMRA-3'
(Final concentration 0.6 μM).
```

Serology

Sows sera collected pre-vaccination was tested for antibodies to PRRSV using the IDEXX PRRS X3 ELISA, following the manufacturer's instructions. In brief, serum samples were diluted 1:40 in 96-well plate coated with a recombinant PRRSV antigen and incubated 30 minutes at 18-26° C. After washing, an anti-porcine horseradish peroxidase conjugate was added and plates were incubated for another 30 minutes at 18-26° C. Unbound conjugate was washed away and TMB substrate was added to the wells. Color development was measured at 650 nm. S/P values were recorded for each sample. If the S/P ratio was ≥0.4 the sample was classified as positive for PRRS antibodies. If the S/P ratio was <0.4 the sample was classified as negative. ELISA instructions are included in the study file.

Clinical Observations

No abnormal clinical observations were recorded for any sow during the post vaccination periods (from D0 to D28).

Rectal Temperatures

In order to study the rectal temperatures, two criteria were followed:

a) The mean rectal temperature post-vaccination of the whole group should not exceed the mean rectal temperature pre-vaccination plus 1.5° C.

1$^{st}$ vac: Mean rectal temperature post-vaccination (at either D0+4 h, D1, D2, D3 or D4)≤[Mean Rectal temperature Pre-vaccination (Mean D−1/D0)]+1.5° C.

2$^{nd}$ vac: Mean rectal temperature post-vaccination (at either D14+4 h, D15, D16, D17 or D18)≤[Mean Rectal temperature Pre-vaccination (Mean D13/D14)]+1.5° C.

b) The individual post-vaccination rectal temperature of each sow should not exceed the pre-vaccination rectal temperature (Pre-vac) plus 2° C.

1$^{st}$ vac: Individual rectal temperature post-vaccination (at either D0+4 h, D1, D2, D3 or D4)≤[Individual rectal temperature Pre-vaccination (Individual mean D-1/D0)]+2.0° C.

2$^{nd}$ vac: Individual rectal temperature post-vaccination (at either D14+4 h, D15, D16, D17 or D18)≤[Individual rectal temperature Pre-vaccination (Individual mean D13/D14)]+2.0° C.

In both T01 and T02 groups, the mean RT post-vaccination did not exceed the mean pre-vaccination plus 1.5° C. In addition, the RT post-vaccination of each sow did not exceed the same sow pre-vaccination rectal temperature plus 2° C. in any of the sows from T01 or T02 groups. Following the first administration, the maximum increase in RT was 0.81° C. (Day 2) in T01 and 0.7° C. (Day 0+4 h) in T02 group. Following the second administration, the maximum increase was observed at Day 17 in both T01 (0.81° C.) and T02 (0.47° C.) groups. None of the sows from T01 or T02 group showed elevated rectal temperatures (≥40.1° C.) at any time-point after vaccination.

Systemic Reactions Post-Vaccination

No systemic reaction post-vaccination was observed in any of the sows from T01 or T02 group.

Local Reactions at Injection Site

Before vaccination, all sows were inspected for the presence of local reactions in the neck area caused by previous inoculations that might have interfered with the evaluation of local reactions at the injection site. Three sows, two from the T01 group (1802 and 2259) and one from the T02 (1663) showed old reactions in the right neck due to previous inoculations. However, all these reactions were located below and were remote from the respective inoculation point. When the left neck was inspected before second vaccination, old reactions were also observed in four sows, two from the T01 group (316 and 1802) and two from the T02 group (2547 and 2842). As observed for the right neck, these reactions were located below the inoculation point. In all cases (for both right and left neck), old reactions were not considered to potentially interfere with the evaluation of local reactions post-vaccination. None of the sows vaccinated with the CP (T01 group) showed local reaction at the injection site at any time-point post-vaccination. Local reactions observed post-vaccination in the T02 group are summarized in 17.

Following the first vaccination, 63% of the T02 sows (5/8) showed a visible and/or palpable swelling at the injection site in the right neck. The maximum swelling observed was a reaction of 2.8 cm of diameter (corresponding to a score of 3) that lasted for 6 days. None of the sows showed reddening, increase on local heat or pain at the injection point.

Following the second vaccination, visible and palpable swelling (left neck) was observed in 50% of the T02 sows (4/8). All observed reactions were scored as 1 or 2 (maximum 1 cm of diameter), and lasted a maximum of 5 days. As observed following the 1$^{st}$ vaccination, none of the sows showed reddening, increase on local heat or pain at the injection point.

TABLE 18

| Summary of local reactions in T02 group | | | | | | | |
|---|---|---|---|---|---|---|---|
| Neck side | Visible Reddening | Visible swelling | Swelling score range | Duration range (days) | Palpable swelling | Pain reaction | Increase heat |
| Right | 0/8 (0%) | 4/8 (50%) | 1-3 | 1-6 | 3/8 (38%) | 0/8 (0%) | 0/8 (0%) |
| Left | 0/8 (0%) | 4/8 (50%) | 1-2 | 1-5 | 4/8 (50%) | 0/8 (0%) | 0/8 (0%) |

Postmortem Examination of Injection Sites

At the macroscopic examination, it was observed that several sows from both groups had lesions in the neck muscles, mainly consisting of multiple nodules of caseous material, which were spread in the whole neck area. These lesions were attributed to old injections because they were not detected at the injection point.

When the inoculation points of T02 sows were inspected, 1/8 presented visible reaction on the right neck and 3/8 on the left neck. In the T01 group, one sow (1/7) showed also visible reaction at the first inoculation point (right neck). All reactions were described as presence of pale muscular fibers, in most cases clearly following the needle trajectory and not measurable. In addition, multiple nodules were observed in two T02 sows (left inoculation point).

Reproductive Performance

No abortions or premature parturitions were recorded in any treatment group. Gestation length ranged between 114 and 117 days in the T01 group and 114 and 119 in the T02 group. Piglets born healthy for each sow were identified with ear tags and were maintained with the In the present study, the safety of the repeated administration of a single dose of the EU PRRS MLV was evaluated at second half of pregnancy (87 days of gestation) in seropositive sows. Safety parameters included systemic reactions to the vaccination, rectal temperature post-vaccination, clinical observations, local reactions at the injection site, reproductive performance and post-mortem examination of injection sites.

No systemic reactions post-vaccination were observed following first or second administration. In addition, no general clinical observations were recorded in any sow throughout the whole study.

Regarding rectal temperatures, none of the sows showed fever at any point after vaccination (RT≥40.1° C.). In addition, the mean rectal temperature post-vaccination did not exceed the mean rectal temperature before vaccination plus 1.5° C. and none of the sows exceeded its own rectal temperature before vaccination plus 2° C.

Local reactions at the injection point were observed in 63% and 50% of the T02 sows at $1^{st}$ and $2^{nd}$ vaccination, respectively. Following the $1^{st}$ vaccination, the maximum swelling observed was a reaction of 2.8 cm of diameter that lasted a maximum of 6 days. Following the second vaccination, the maximum swelling was 1 cm of diameter and the maximum duration was 5 days. None of the sows showed reddening, increase in local heat or pain at the injection point following any administration.

At the postmortem examination, visible reaction at the inoculation point was observed only in 3/8 vaccinated sows. Two of them (15 and 1663) corresponded to the ones with the highest swelling score (2 and 3, respectively) given at the evaluation of local reactions; macroscopically, the lesions were described as pale muscular fibers following the needle trajectory, which were diagnosed as moderate granulomatous myositis with involvement of muscular fibers. In the case of sow 15, vaccine drops were observed inside the lesion, supporting the fact that this lesion was induced as a result of the administration of the test item. For the other T02 sow (2547) that showed visible reaction, the lesion was also described as pale muscular fibers following the needle trajectory, but in this case also with multiple nodules containing caseous material. At the histopathological analysis, this lesion was diagnosed as severe granulomatous myositis with presence of focal but extensive necrosis. Since the presence of multiple nodules in the neck area, but not specifically in the inoculation point, was observed also in 8/8 T02 and in 5/7 T01 sows, it is possible that the lesion observed in sow 2547 was caused by previous injections rather than by the test item. This would be supported by the fact that, during the in vivo evaluation of local reactions, this sow had only a swelling of <0.5 cm of diameter that lasted 5 days.

PRRSV-associated reproductive disorders are characterized by increase in premature farrowings, late term abortions, stillborn or low viable piglets and mummified foetuses. In the present study, no abortions or premature farrowings were recorded. In addition, no apparent effect of vaccination was observed on the number stillborns, mummies or low viable piglets. PRRSV infection might also increase the pre-weaning mortality. In the present study, the mean % of pre-weaning mortality was 6.0 and 5.3 in T01 and T02 groups, respectively, indicating no impact of vaccination on piglet survival.

Finally, all serum samples collected at birth or at weaning from piglets born from both T01 and T02 sows were PRRSV negative by RT-qPCR, indicating the lack of transplacental infection following vaccination.

Thus, the administration of a repeated single dose of the EU PRRSV MLV to PRRSV seropositve sows at 87 days of pregnancy: did not induce abnormal systemic reactions (anaphylactic shock, vomiting); did not induce any clinical observation during the 14 days post-vaccination; did not induce abnormal rectal temperatures post-vaccination; caused local reactions at the injection site in 63% and 50% of sows after the $1^{st}$ and $2^{nd}$ vaccination, respectively wherein such reactions consisted of palpable and/or visible swelling (from 0.4 to 2.8 cm of diameter) which disappeared between 1 to 6 days; had no impact on the reproductive parameters; and did not cause transplacental infection.

The invention claimed is:

1. A vaccine for protecting a porcine animal against infection by a PRRS virus, which vaccine comprises: (a) a European PRRS virus encoded by the polynucleotide molecule of SEQ ID NO: 5 or any polynucleotide that is at least 90% identical to SEQ ID NO: 5; (b) said encoding polynucleotide molecule; (c) said polynucleotide molecule in the form of a plasmid; or (d) a viral vector comprising said polynucleotide molecule;

in an amount effective to produce immunoprotection against infection, and a carrier suitable for veterinary use, and wherein said vaccine provides early and safe vaccination as early as when the piglet is one day old or less, and wherein said vaccine provides a duration of immunity for up to 6 months.

2. The vaccine according to claim 1, wherein said vaccine provides protection against infection when administered to a piglet that is about 8-12 hours old.

3. The vaccine of claim 1 wherein onset of immunity is provided beginning at two weeks after vaccination.

4. The vaccine of claim 1 wherein onset of immunity is provided beginning at 24-28 days after vaccination.

5. A method for vaccinating a porcine animal against infection by a European PRRS virus, comprising administering said vaccine between about 12 hours after birth and 3 weeks of age, prior to weaning of said animal, wherein said vaccine comprises (a) an isolated polynucleotide molecule comprising a DNA sequence encoding an infectious RNA molecule encoding a European PRRS virus, said DNA sequence comprising SEQ ID NO: 5 or any polynucleotide that is at least 90% identical to SEQ ID NO: 5, (b) an infectious RNA molecule encoding a European PRRS virus, wherein said infectious RNA molecule is encoded by the DNA sequence of (a);

(c) said polynucleotide molecule (a) in the form of a plasmid, (d) a viral vector comprising an infectious RNA molecule (b), or (e) a European PRRS virus encoded by an infectious RNA molecule, said infectious RNA molecule encoded by the isolated polynucleotide molecule according to (a), and wherein said vaccine virus was adapted to grow in porcine cells, or non-porcine mammalian cells that express a porcine CD163 receptor, prior to administration of said vaccine virus to porcine animal.

6. The method of claim 5 wherein protective immunity arises no later than about 28 days after vaccination.

7. The method of claim 5 wherein the duration of protective immunity provided is up to 6 months.

* * * * *